US007932434B2

(12) United States Patent
Halterman et al.

(10) Patent No.: US 7,932,434 B2
(45) Date of Patent: Apr. 26, 2011

(54) LATE BLIGHT RESISTANCE GENE FROM WILD POTATO

(75) Inventors: Dennis A. Halterman, Middleton, WI (US); Zhenyu Liu, Madison, WI (US)

(73) Assignees: Wisconsin Alumni Research Foundation, Madison, WI (US); The United States of America as represented by the Secretary of Agriculture, Washington, DC (US)

( * ) Notice: Subject to any disclaimer, the term of this patent is extended or adjusted under 35 U.S.C. 154(b) by 195 days.

(21) Appl. No.: 12/191,540

(22) Filed: Aug. 14, 2008

(65) Prior Publication Data

US 2009/0151019 A1 Jun. 11, 2009

Related U.S. Application Data

(60) Provisional application No. 60/956,037, filed on Aug. 15, 2007.

(51) Int. Cl.
*A01H 5/00* (2006.01)
*C12N 15/09* (2006.01)
*C12N 15/29* (2006.01)
*C12N 15/82* (2006.01)

(52) U.S. Cl. ........ 800/279; 800/278; 800/298; 800/295; 800/317; 536/23.6; 435/69.1; 435/320.1; 435/468; 435/419; 530/370

(58) Field of Classification Search .................. None
See application file for complete search history.

(56) References Cited

U.S. PATENT DOCUMENTS

| 4,743,548 | A | 5/1988 | Crossway et al. | |
|---|---|---|---|---|
| 5,880,333 | A | 3/1999 | Goff et al. | |
| 6,002,072 | A | 12/1999 | McMaster et al. | |
| 2003/0221215 | A1* | 11/2003 | Allefs et al. | 800/279 |
| 2005/0204419 | A1* | 9/2005 | Helgeson et al. | 800/279 |
| 2006/0248610 | A1 | 11/2006 | Van Der Vossen et al. | |

FOREIGN PATENT DOCUMENTS

| WO | WO 90/02189 | 3/1990 |
|---|---|---|
| WO | WO 93/01283 | 1/1993 |
| WO | WO 99/09151 | 2/1999 |
| WO | WO 00/26388 | 5/2000 |
| WO | WO 03/066675 | 8/2003 |

OTHER PUBLICATIONS

Abler, M.L. et al., "Isolation and characterization of a genomic sequence encoding the maize Cat3 catalase gene," Plant Mol. Biol. (1993) 22:1031-1038.
Adams, S.P. et al., "Hindered dialkylamino nucleoside phosphite reagents in the synthesis of two DNA 51-mers," J. Am. Chem. Soc. (1983) 105:661-663.
Ainley, W.M. et al., "Development of a heat shock inducible expression cassestte for plants: characterization of parameters for its use in transient expression assays," Plant Mol. Biol. (1990) 14:949-967.
Altschul, S.F. et al., "Gapped BLAST and PSI-BLAST: a new generation of protein database search programs," Nucl. Acids Res. (1997) 25(17):3389-3402.
An, G. et al., "Both TATA box and upstream regions are required for the nopaline synthases promoter activity in transformed tobacco cells," Mol. Gen. Genet. (1986) 203:245-250.
Anderson, P.A. et al., "Inactivation of the flax rust resistance gene M associated with loss of a repeated unit within the leucine-rich repeat coding region," The Plant Cell (1997) 9:641-651.
Aoyama, T. et al., "A glucocorticoid-mediated transcriptional induction system in transgenic plants," The Plant Journal (1997) 11(3):605-612.
Ausubel et al., Current Protocols in Molecular Biology, John Wiley & Sons, Inc., Hoboken, NJ (1993) vols. 1-3; cover and table of contents.
Baima, S. et al., "The *Arabidopsis* ATHB-8 HD-zip protein acts as the differentiation-promoting transcription factor of the vascular meristems," Plant Physiol. (2001) 126:643-655.
Ballvora, A. et al., "The R1 gene for potato resistance to late blight (*Phytophthora infestans*) belongs to the leucine zipper/NBS/LRR class of plant resistant genes," The Plant Journal (2002) 30(3):361-371.
Bartlett, J.M.S. et al., PCR Protocols, Humana Press, Totowa, NJ (2003) cover and table of contents.
Bezerra, I.C. et al., "A corm-specific gene encodes tarin, a major globulin of taro (*Colocasia esculenta* L. Schott)," Plant Mol. Biol. (1995) 28:137-144.
Birch, R.G., "Plant transformation: problems and strategies for practical application," Annu. Rev. Plant Physiol. Plant Mol. Biol. (1997) 48:297-326.
Bossinger, G. et al., "Initiation patterns of flower and floral organ develoopment in *Arabidopsis thaliana*," Dev. (1996) 122:1093-1102.
Boutilier, K. et al., "Ectopic expression of Baby Boom triggers a conversion from vegetative to embryonic growth," The Plant Cell (2002) 14:1737-1749.
Brandstatter, I. et al., "Two genes with similarity to bacterial response regulation are rapidly and specifically induced by cytokinin in *Arabidopsis*," The Plant Cell (1998) 10:1009-1019.
Broothaerts, W. et al., "Gene transfer to plants by diverse species of bacteria," Nature (2005) 433:629-633.
Busk, P.K. et al., "Regulatory elements in vivo in the promoter of the abscisic acid responsive gene rab17 from maize," The Plant Journal (1997) 11(6):1285-1295.
Casal, J.J. et al., "Different phototransduction kinetics of phytochrome A and phytochrome b in *Arabidopsis thaliana*," Plant Physiol. (1998) 116:1533-1538.
Caten, C.E. et al., "Spontaneous variability of single isolates of *Phytophthora infestans*. I. Cultural variation," Canadian J. Botany (1968) 46:329-347.
Cearley, J.A. et al., "Regeneration of *Slanum tuberosum* CV. Katandin from leaf explants in vitro," Am. Potato J. (1997) 74:125-129.
Chen, W. et al., "The promoter of a H2O2-inducible, *Arabidopsis* glutathione S-transferase gene contains closely linked OBF- and OBP1-binding sites," The Plant J. (1996) 10(6):955-966.

(Continued)

*Primary Examiner* — Medina A Ibrahim

(74) *Attorney, Agent, or Firm* — Michael Best & Friedrich LLP

(57) ABSTRACT

A novel resistance gene and its encoded protein isolated from the wild potato, *Solanum verrucosum*, are disclosed. The gene and protein are useful for conferring disease resistance to plants, particularly resistance to potato late blight disease in solanaceous species such as potato, tomato, and tobacco. Compositions and methods that use the genes and proteins of this invention to enhance plant disease resistance are also disclosed, as are transgenic plants that comprise the novel resistance genes and proteins.

24 Claims, 6 Drawing Sheets

OTHER PUBLICATIONS

Chittoor, J.M. et al., "Differential induction of a peroxidase gene family during infection of rice by *Xanthomonas oryzae* pv. *oryzae*," Mol. Plant-Microbe Interactions (1997) 10:861-871.

Choi, Y. et al., "Tissue-specific and developmental regulation of a gene encoding a low molecular weight sulfur-rich protein in soybean seeds," Mol. Gen. Genet. (1995) 246:266-268.

Colton, L.M. et al., "Marker-assisted selection for the broad-spectrum potato late blight resistance conferred by gene RB derived from a wild potato species," Crop Sci. (2006) 46:589-594.

Crispeels, M.J. et al., Plants, Genes and Crop Biotechnology, James and Bartlett Publishers, Sudbury, MA (2003) Second Edition, cover and table of contents.

Dagless, E.M. et al., "A CaMV 35S promoter driven cDNA clone of tobacco mosaic virus can infect host plant tissue despite being uninfectious when manually inoculated onto leaves," Arch. Virol. (1997) 142:183-191.

Dasgupta, S. et al., "Cloning and sequencing of 5' flanking sequence from the gene encoding 2S storage protein, from two *Brassica* species," Gene (1993) 133:301-302.

De Castro, L.A.B. et al., "Spatial and temporal gene expression patterns occur during corm development," The Plant Cell (1992) 4:1549-1559.

De Veylder, L. et al., "Herbicide safener-inducible gene expression in *Arabidopsis thaliana*," Plant Cell Physiol. (1997) 38(5):568-577.

Di Laurenzio, L. et al., "The Scarecrow gene regulates an asymmetric cell division that is essential for generating the radial organization of the *Arabidopsis* root," Cell (1996) 86:423-433.

Drews, G.N. et al., "Negative regulation of the *Arabidopsis* homeotic gene AGAMOUS by the APETALA2 product," Cell (1991) 65:991-1002.

Elge, S. et al., "An *Arabidopsis* inositol p hospholipid kinase strongly expressed in procambial cells,: synthesis of PtdIns(4,5)P2 and PtdIns(3,4,5)P3 in insect cells by 5-phosphorylation of precursors," The Plant Journal (2001) 26(6):561-571.

Enjuto, M. et al., "Expressin of the *Arabidopsis* HMG2 gene, encoding 3-hydroxy-3-methylglutaryl coenzyme A reductase, is restricted to meristematic and floral tissues," The Plant Cell (1995) 7:517-527.

Ficker, M. et al., "A promoter directing high level expression in pistils of transgenic plants," Plant Mol. Biol. (1997) 35:425-431.

Flanagan, C.A. et al., "Specific expression of the AGL1 MADS-box gene suggests regulatory functions in *Arabidopsis gynoecium* and ovule development," The Plant Journal (1996) 10(2):343-353.

Fromm, M. et al., "Expression of genes transferred into monocot and dicot plant cells by electroporation," Proc. Natl. Acad. Sci. (1985) 82:5824-5828.

Fry, W.E. et al., "Re-emergence of potato and tomato late blight in the United States," Plant Dis. (1997) 81:1349-1357.

Fu, B-Y. et al, "Construction of the physical map of Pi-2(5), a blast resistance gene in rice," Yi Chuan Xue Bao (2000) 27:787-791.

Galweiler, L. et al., "Regulation of polar auxin transport by AtPIN1 in *Arabidopsis* vascular tissue," Science (1998) 282:2226-2230.

Gan, S. et al., "Inhibition of leaf senescence by autoregulated production of cytokinin," Science (1995) 270:1986-1988.

Gelvin, S.B., "*Agrobacterium*-mediated plant transformation: the biology behind the 'gene-jockeying' tool," Microbiol. Mol. Biol. Rev. (2003) 67(1):16-37.

Granger, C.L. et al., "Isolation of an *Arabidopsis* homologue of the maize homeobox knotted-1 gene," Plant Mol. Biol. (1996) 31:373-378.

Groom, Q.J. et al., "rbohA, a rice homologue of the mammalian gp91phox respiratory burst oxidase gene," The Plant J. (1996) 10(3):515-522.

Guerrero, F.D. et al., "Promoter sequences from a maize pollen-specific gene direct tissue-specific transcription in tobacco," Mol. Gen. Genet. (1990) 224:161-168.

Gustafson-Brown, C. et al., "Regulation of the *Arabidopsis* floral homeotic gene APETALA1," Cell (1994) 76:131-143.

Haberlach, G.T. et al., "Isolation, culture and regeneration of protoplasts from potato and several related solanum species," Plant Sci. (1985) 39:67-74.

Halterman, D.A. et al., "Performance of transgenic potato containing the late blight resistance gene RB," Plant Disease (2008) 92:339-343.

Hammond-Kosack, K.E. et al., "Functional expression of a fungal avirulence gene from a modified potato virus X genome," Mol. Plant-Microbe Interact. (1995) 8:181-185.

Hansen, G. et al., "Wound-inducible and organ-specific expression of ORF13 from *Agrobacterium rhizogenes* 8196 T-DNA in transgenic tobacco plants," Mol. Gen. Genet. (1997) 254:337-343.

Hecht, V. et al., "The *Arabidopsis* somatic embryogenesis receptor kinase 1 gene is expressed in developing ovules and embryos and enhances embryogenic competence in culture," Plant Phys. (2001) 127:803-816.

Heck, G.R. et al., "AGL15, a MADS domain protein expressed in developing embryos," The Plant Cell (1995) 7:1271-1282.

Helgeson, J.P. et al., "Somatic hybrids between *Solanum bulbocastanum* and potato: a new source of resistance to late blight," Theor. Appl. Genet. (1998) 96:738-742.

Holtorf, S. et al., "Comparison of different constitutive and inducible promoters for the overexpression of transgenes in *Arabidopsis thaliana*," Plant Mol. Biol. (1995) 29:637-646.

Horsch, et al., "Inheritance of functional foreign genes in plants," Science (1984) 223:496-498.

Huang, S. et al., "The *Arabidopsis* ACT11 actin gene is strongly expressed in tissues of the emerging inflorescence, pollen, and developing ovules," Plant Mol. Biol. (1997) 33:125-139.

Hwang, I. et al., "Two-component circuitry in arabidopsis cytokinin signal transduction," Nature (2001) 413:125-139.

Igarashi, M. et al., "Expression of the zinnia TED3 promoter in developing tracheary elements of transgenic *Arabidopsis*," Plant Mol. Biol. (1998) 36:917-927.

Ito, T. et al., "Overexpression of a gene encoding a cytochrome P450, CYP78A9, induces large and seedless fruit in *Arabidopsis*," The Plant Cell (2000) 12:1541-1550.

Jansky, S., "Breeding for disease resistance in potato," Plant Breeding Reviews (2000) 19:69-155.

Jordano, J. et al., "A sunflower helianthinin gene upstream sequence ensemble contains an enhancer and sites of nuclear protein interaction," The Plant Cell (1989) 1:855-866.

Kamoun, S., "Nonhost resistance to phytophthora: novel prospects for a classical problem," Curr. Opin. Plant Biol. (2001) 4:295-300.

Karlin, S. et al., "Methods for assessing the statistical significance of molecular sequence features by using general scoring schemes," Proc. Natl. Acad. Sci. USA (1990) 87:2264-2268.

Kerstetter, R. et al., "Sequence analysis and expression patterns divide the maize knotted1-like homeobox genes into two classes," The Plant Cell (1994) 6:1877-1887.

Kirch, H-H. et al., "Structural organization, expressiona dn promoter activity of a cold-stress-inducible gene of potato (*Solanum tuberosum* L.)," Plant Mol. Biol. (1997) 33:897-909.

Klee, H. et al., "*Agrobacterium*-mediated plant transformation and its further applications to plant biology," Ann. Rev. Plant Physiol. (1987) 38:467-486.

Klein, T.M. et al., "High-velocity microprojectiles for delivering nucleic acids into living cells," Nature (1987) 327:70-73.

Kriegler, M., Gene Transfer and Expression: A Laboratory Manual, Stockton Press, New York, NY (1990) cover and table of contents.

Kuhl, J.C. et al., "Characterization and mapping of Rpi1, a late-blight resistance locus from diploid (1EBN) Mexican *Solanum pinnatisectum*," Mol. Genet. Genomics (2001) 265:977-985.

Kumagai, M.H. et al., "Cytoplasmic inhibition of carotenoid biosynthesis with virus-derived RNA," Proc. Natl. Acad. Sci. USA (1995) 92:1679-1683.

Lee, K. et al., "Genes enclding oleosins in maize kernel of inbreds Mo17 and B73," Plant Mol. Biol. (1994) 26:1981-1987.

Li, S.F. et al., "A novel myb-related gene from *Arabidopsis thaliana*," FEBS Letts. (1996) 379:117-121.

Lincoln, C. et al., "A knotted1-like homeobox gene in *Arabidopsis* is expressed in the vegetative meristem and dramatically alters leaf morphology when overexpressed in transgenic plants," The Plant Cell (1994) 6:1859-1876.

Liu, Z. et al., "Patterns of diversifying selection in the phytotoxin-like scr74 gene family of *Phytophthora infestans*," Mol. Biol. Evol. (2005) 22(3):659-672.

Liu, Z.-B. et al., "A G-box-binding protein from soybean binds o the E1 auxin-response element in the soybean GH3 promoter and contnains a proline-rich repression domain," Plant Physiol. (1997) 115:397-407.

Long, J.A. et al., "A member of the Knotted class of homeodomain proteins encoded by the STM gene of *Arabidopsis*," Nature (1996) 379:66-69.

Lotan, T. et al., "*Arabidopsis* Leafy Cotyledon1 is sufficient to induce embryo development in vegetative cells," Cell (1998) 93:1195-1205.

Luerssen, H. et al., "FUSCA3 encodes a protein with a conserved VP1/AB13-like B3 domain which is of functional importance for the regulation of seed maturation in *Arabidopsis thaliana*," The Plant Journal (1998) 15(6):755-764.

Maiti, I.B. et al., "Promoter/leader deletion analysis and plant expression vectors with the figwort mosaic virus (FMV) full length transcript (FLt) promoter containing single or double enhancer domains," Transgenic Res. (1997) 6:143-156.

Malcolmson, J.F. et al., "New R genes in *Solanum demissum* lindl and their complementary races of *Phytophthora infestans* (Mont.) de bary," Euphytica (1966) 15:199-203.

Mandel, M.A. et al., "The *Arabidopsis* AGL8 MADS box gene is expressed in inflorescence meristems and is negatively regulated by APETALA1," The Plant Cell (1995) 7:1763-1771.

Manjunath, S. et al., "Molecular characterization and promoter analysis of the maize cytosolic glyceraldehyde 3-phosphate dehydrogenase gene family and its expression during anoxia," Plant Mol. Biol. (1997) 33:97-112.

Martin, T. et al., "Identification of mutants in metabolically regulated gene expression," The Plant Journal (1997) 11(1):53-62.

Martinez, P. et al., "Structure, evolution and anaerobic regulation of a nuclear gene encoding cytosolic glyceraldehyde-3-phosphate dehydrogenase from maize," J. Mol. Biol. (1989) 208:551-565.

Masgrau, C. et al., "Inducible overexpression of oat arginine decarboxylase in transgenic tobacco plants," The Plant Journal (1997) 11(3):465-473.

Meier, I. et al., "Elicitor-inducible and constitutive in vivo DNA footprints indicate novel cis-acting elements in the promoter of a parsley gene encoding pathogenesis-related protein 1," The Plant Cell (1991) 3:309-315.

Meier, I. et al., "The tomato RBCS3A promoter requires integration into the chromatin for correct organ-specific regulation," FEBS Lett. (1997) 415:91-95.

Millar, A.A. et al., "The alcohol dehydrogenase genes of cotton," Plant Mol. Biol. (1996) 31:897-904.

Naess, S.K. et al., "Resistance to late blight in *Solanum bulbocastanum* is mapped to chromosome 8," Theor. Appl. Genet. (2000) 101:697-704.

Nei, M. et al., "Simple methods for estimating the numbers of synonymous and nonsynonymous nucleotide substitutions," Mol. Biol. Evol. (1986) 3(5):418-426.

Nelson, A.J. et al., "Isolation of a monocot 3-hydroxy-3-methylglutaryl coenzyme A reductase gene that is elicitor-inducible," Plant Mol. Biol. (1994) 25:401-412.

Nielsen, R. et al., "Likelihood models for detecting positively selected amino acid sites and applications to the HIV-1 envelope gene," Genetics (1998) 148:929-936.

O'Grady, K. et al., "Site-directed mutagenesis of the enhancer region of the 780 gene promoter of T-DNA," Plant Mol. Biol. (1995) 29:99-108.

Parker, J.E. et al., "The *Arabidopsis* downy mildew resistance gene RPP5 shares similarity to the toll and interleukin-1 receptors with N and L6," The Plant Cell (1997) 9:879-894.

Paszkowski, J. et al., "Direct gene transfer to plants," The EMBO J. (1984) 3(12):2717-2722.

Pearson, W.R. et al., "Improved tools for biological sequence comparison," Proc. Natl. Acad. Sci. USA (1988) 85:2444-2448.

Peng, Y-L. et al., "A novel lipoxygenase from rice," J. Biol. Chem. (1994) 269(5):3755-3761.

Perbal, B., A Practical Guide to Molecular Cloning, John Wiley & Sons, New York, NY (1988) 2nd Edition, cover and table of contents.

Quattrocchio, F. et al., "Regulatory genes controlling anthocyanin pigmentation are functionally conserved among plant species and have distinct sets of target genes," The Plant Cell (1993) 5:1497-1512.

Ray, A. et al., "*Arabidopsis* floral homeotic gene BELL (BEL1) controls ovule development through negative regulation of AGAMOUS gene (AG)," Proc. Natl. Acad. Sci. USA (1994) 91:5761-5765.

Reiser, L. et al., "The BELL1 gene encodes a homeodomain protein involved in pattern formation in the *Arabidopsis* ovule primordium," Cell (1995) 83:735-742.

Sakai, T. et al., "Analysis of the promoter of the auxin-inducible gene, parC, of tobacco," Plant Cell Physiol. (1996) 37(7):906-913.

Sambrook et al., Molecular Cloning—A Laboratory Manual, Cold Spring Harbor Laboratory, Cold Spring Harbor, NY (1989) cover and table of contents.

Sheen, J., "Ca2+-dependent protein kinases and stress signal transduction in plants," Science (1996) 274:1900-1902.

Sheridan, W.F. et al., "The mac1 gene: controlling the commitment to the meiotic pathway in maize," Genetics (1996) 142:1009-1020.

Sjodahl, S. et al., "Deletion analysis of the *Brassica napus* cruciferin gene cru 1 promoter in transformed tobacco: promoter activity during early and late stages of embryogenesis is influenced by cis-acting elements in partially separate regions," Planta (1995) 197:264-271.

Slocombe, S.P. et al., "Temporal and tissue-specific regulation of a brassica napus stearoyl-acyl carrier protein desaturase gene," Plant Physiol. (1994) 104:1167-1176.

Solano, R. et al., "Nuclear events in ethylene signaling: a transcriptional cascade mediated by ethylene-insensitive3 and ethylene-response-factor1," Genes & Dev. (1998) 12:3703-3714.

Song, J. et al., "Gene RB cloned from *Solanum bulbocastanum* confers broad spectrum resistance to potato late blight," Proc. Natl. Acad. Sci. USA (2003) 100(16):9128-9133.

Stange, C. et al., "Phosphorylation of nuclear proteins directs binding to salicylic acid-responsive elements," The Plant Journal (1997) 11(6):1315-1324.

Stone, S.L. et al., "Leafy cotyledon2 encodes a B3 domain transcription factor that induces embryo development," Proc. Natl. Acad. Sci. USA (2001) 98(20):11806-11811.

Streit, W.R. et al., "A biotin-regulated locus, bioS, in a possible survival operon of *Rhizobium meliloti*," Mol. Plant Microbe Interact. (1997) 10(7):933-937.

Suzuki, M. et al., "Viviparous1 alters global gene expression patterns through regulation of abscisic acid signaling," Plant Phys. (2003) 132:1664-1677.

Thompson, J.D. et al., "The CLUSTAL_X windows interface: flexible strategies for multiple sequence alignment aided by quality analysis tools," Nucl. Acids Res. (1997) 25(24):4876-4882.

Urao, T. et al., "Molecular cloning and characterization of a gene that encodes a MYC-related protein in *Arabidopsis*," Plant Mol. Biol. (1996) 32:571-576.

Verdaguer, B. et al., "Isolation and expression in transgenic tobacco and rice plants, of the cassava vein mosaic virus (CVMV) promoter," Plant Mol. Biol. (1996) 31:1129-1139.

Wan, L. et al., "Early stages of seed development in *Brassica napus*: a seed coat-specific cysteine proteinase associated with programmed cell death of the inner integument," The Plant Journal (2002) 30(1):1-10.

Watson, J.D. et al., Recombinant DNA, Freeman & Co, New York, NY (1992) Second Edition, cover and table of contents.

Weising, K. et al., "Foreign genes in plants: transfer, structure, expression and applications," Annu. Rev. Genet. (1988) 22:421-477.

Wulff, B.B.H. et al., "Domain swapping and gene shuffling identify sequences required for induction of an Avr-dependent hypersensitive response by the tomato Cf-4 and Cf-9 proteins," The Plant Cell (2001) 13:255-272.

Yamada, T. et al., "Functional analysis of the promoters of phenylalanine ammonia-lyase genes in pea," Plant Cell Physiol. (1994) 35(6):917-926.

Yamamoto, Y.T. et al., "Characterization of cis-acting sequences regulating root-specific gene expression in tobacco," The Plant Cell (1991) 3:371-382.

Yang, Z. et al., "Statistical methods for detecting molecular adaptation," Tree (2000) 15(12):496-503.

Yang, Z., "PAML: a program package for phylogenetic analysis by maximum likelihood," Comput. Appl. Biosci. (1997) 13:555-556.

Zhang, J.Z. et al., "DNA sequences that activate isocitrate lyase gene expression during late embryogenesis and during postgerminative growth," Plant Physiol. (1996) 110:1069-1079.

Zhong, H.H. et al., "The circadian clock gates expression of two arabidopsis catalase genes to distinct and opposite circadian phases," Mol. Gen. Genet. (1996) 251:196-203.

Zhu, Q. et al., "Isolation and characterization of a rice gene encoding a basic chitinase," Mol. Gen. Genet. (1991) 226:289-296.

Zuo, J. et al., "An estrogen receptor-based transactivator XVE mediates highly inducible gene expression in transgenic plants," The Plant Journal (2000) 24(2):265-273.

* cited by examiner

FIGURE 1

```
                 1                                                    50
SEQ ID NO:15     MAEAFIQVLLDNLTSVLKGELVLLFGFQDEFQRLSSIFSTIQAVLEDAQE
                 KQLNDKP☒ENWLQKLNAATYEVDDILDEYKT☒ATRFLQSEYGRYHPKAIP
                 FRHKVGKRMDQVMKKLNAIAEERKNFHLQEKIIERQAATRETGSVLTEPQ
                                                      Kinase 1a/P-loop
                 VYGRDKENDEIVKILINNASDAQKL☒VLPI☒GMGGLGKTTLSQMVFNDQR
                 VTEHFYPKLWICVSNDFDEKRLIKAIVESIEGKSLSDMDLAPLQKKLQEL
                       Kinase 2a                         Kinase 3a
                 ☒NGKRYLLVLDDVWNEDQQKWANLRAVLKVGASGSFVLTTTRLEKVGSIM
                 GTLQPYELSNLSPEDCWLFIQRAFGHQEEINPNLVDIGKEIMKKSGGVP
                 LAAKTLGGILRFKREEREWEHVRDSPIWNLPQDESSILPALRLSYHHLPL
                 DLRQCFVYCAVFPKDTKMAKENLIAFWMAHGFLLSKGNLELEDVGNEVWN
                 ELYLRSFFQEIEVK☒GKTYFKMHDLIHDLATSLFSANTSSSNIREIY☒NY
                                     520
                 DGYMMSIG☒AEVVSSYSPSL
```

LRR

| | | |
|---|---|---|
| SEQ ID NO:16 | 1 | LQKFVSLRVLNLRNSDLNQLPSS |
| SEQ ID NO:17 | 2 | IGDLVHLRYLDLSDNIRIRSLPKR |
| SEQ ID NO:18 | 3 | LCKLQNLQTLDL☒NCYSLSCLPKQ |
| SEQ ID NO:19 | 4 | TSKLGSLRNLLLDGCSLTSTPPRIGL |
| SEQ ID NO:20 | 5 | LTCLKSLS☒FVIGKRK |
| SEQ ID NO:21 | 6 | GY☒LGELKNLNLYG |
| SEQ ID NO:22 | 7 | SISITKLERVKKGRDAKEAN |
| SEQ ID NO:23 | 8 | ISVKANLHSLSLSWDFDGTHRYE |
| SEQ ID NO:24 | 9 | SEVLEALKPHSNLK |
| SEQ ID NO:25 | 10 | YLEIIGFRGIRLPDWMN |
| SEQ ID NO:26 | 11 | QSVLKNVVSITIRGCENCSCLPP |
| SEQ ID NO:27 | 12 | FGELPSLESLELHTG |
| SEQ ID NO:28 | 13 | SAEVEYVEENAH |
| SEQ ID NO:29 | 14 | PGRFPSLRKLVICDFGNLKGLLKKEG |
| SEQ ID NO:30 | 15 | EEQFPVLEEMTIHGCPMFV |
| SEQ ID NO:31 | 16 | IPTLSSVKTLKVD-VTDATVLRS |
| SEQ ID NO:32 | 17 | ISNLRALTSLDISSNYEATSLPEEM |
| SEQ ID NO:33 | 18 | FKNLADLKDLTISDFKNLKELPTC |
| SEQ ID NO:34 | 19 | LASLNALNSLQIEYCDALESLPEEG |
| SEQ ID NO:35 | 20 | VKSLTSLTELSVSNCMTLKCLPEG |
| SEQ ID NO:36 | 21 | LQHLTALTTLII☒QCPIVIKRCEKE |

LATE BLIGHT RESISTANCE GENE FROM WILD POTATO

CROSS-REFERENCE TO RELATED APPLICATIONS

This invention claims priority to U.S. Provisional Patent Application Ser. No. 60/956,037, filed Aug. 15, 2007, which is herein incorporated by reference.

GOVERNMENT INTERESTS

This invention was made with United States government support under grant No. T-6-3655-120 awarded by the USDA. The United States government has certain rights in this invention.

TECHNICAL FIELD

This invention relates to the fields of plant physiology, genetics, and molecular biology. In particular, the invention provides biological protection of plants against microbial infections using novel genes, proteins, and methods of enhancing disease resistance in plants.

BACKGROUND

Potato (*Solanum tuberosum* L.) is the world's fourth most valuable crop. In the United States of America, the value of the crop exceeds two billion dollars each year. Worldwide production of the cultivated potato exceeds that of all other dicot food crops. Potato is also host to more than sixty pathogens of economic significance, causing costly diseases in terms of crop loss. The expenses associated with application of chemicals, and the environmental impact of pesticide use, are significant. Such costs could be minimized or avoided if resistant potato varieties were available. However, adequate resistance for many diseases has not been incorporated into potato cultivars, partly because of the lack of resistance genes that breeders can use to develop resistant cultivars.

Among the most devastating potato diseases is late blight, a foliar and tuber disease caused by the oomycete pathogen *Phytophthora infestans* (*P. infestans*), the causative agent of the legendary Great Irish Potato Famine of 1845. The late blight fungus is also a devastating pathogen on crops other than potato; it infects tomatoes, eggplants, and other solanaceous species. To combat the disease caused by *P. infestans*, growers use a combination of practices, such as sanitary measures, resistant cultivars, and fungicides. The fungicide approach has repeatedly failed due to the remarkable ability of *P. infestans* to acquire resistance. The attempted breeding of disease resistant strains of *Solanum tuberosum* (*S. tuberosum*), the cultivated species of potato, has also failed over time.

Possible sources of resistance to many potato pathogens exist in the approximately 225 wild *Solanum* species. Several *Solanum* species have been crossed with the cultivated potato in an effort to introgress disease-resistance genes, including genes that confer resistance to late blight disease (Jansky, 2000, *Plant Breed. Rev.* 19: 69-155). Among wild potato species with late blight resistance is the hexaploid *Solanum demissum*. Resistance from this species has been incorporated into potato via sexual crosses. Eleven race-specific resistance genes conferring late blight resistance have been described in *Solanum demissum* (Malcolmson and Black, 1966, *Euphytica* 15:199-203), and introgressed into cultivated potato varieties using classical breeding. These genes are characterized by pathogen race specificity and a hypersensitive phenotype. Unfortunately, virulent races of *P. infestans* have rapidly overcome the majority of these 11 late blight resistance genes in most potato growing regions (Fry and Goodwin, 1997, *Plant Disease* 81: 1349-1357).

Because *P. infestans* is capable of acquiring resistance, efforts have been directed toward the identification of additional late blight resistance genes in wild potato species that are naturally resistant to *P. infestans*. For example, Rpi1, a late blight resistance gene from *Solanum pinnatisectum*, was described and mapped by Kuhl et al., 2001, *Mol. Genet. Genomics* 265: 977-985. Rpi1 has never been deployed for potato protection and the durability potential of Rpi1 remains unexplored. In addition, to confer late blight resistance, somatic hybrids between cultivated potato and the wild Mexican diploid *Solanum bulbocastanum* (*S. bulbocastanum*) have also been generated. Such somatic hybrids retained the late blight resistance of the wild species, and could be backcrossed to cultivated potato (Helgeson et al., 1998, *Theor. Appl. Genet.* 96: 738-742). Mapping experiments revealed a single locus on *Solanum bulbocastanum* chromosome 8 that imparted the late blight resistance phenotype (Naess et al., 2000, *Theor. Appl. Genet.* 101: 697-704). This region was dubbed RB (resistance region from *S. bulbocastanum*), and a gene from *S. bulbocastanum* that confers late blight resistance is referred to as $RB^{blb}$.

The global food shortage crisis has highlighted the importance of the ongoing quest for materials and methods for conferring disease resistance in plants, for example as disclosed in International Patent Application Publication No. WO/1999/009151, and in particular the quest for potato genes for resistance to late blight, as disclosed in U.S. Patent Application No. 2005/0204419 A1. However, despite decades of active breeding effort to control late blight, this disease still causes the loss of billions of revenue dollars for growers each year (Kamoun, 2001, *Curr. Opin. Plant Biol.* 4: 295-300). Accordingly, a source of resistance to *Phytophthora* species that could be introduced into the cultivated species by molecular genetic techniques would be of great value. As a result, there is an ongoing need to identify genes that might confer late blight disease resistance. If such genes can be identified and isolated, they can be introduced by molecular genetic techniques into domestic potato and species other than potato to confer resistance to one or more plant pathogens. The products of such research are in demand by potato growers, who keep looking for novel varieties containing genes and other factors that promote resistance to *P. infestans* and related pathogens. The present invention addresses these and other related needs.

BRIEF SUMMARY

Isolated polynucleotides are provided, which encode polypeptides comprising amino acid sequences that are at least 95% identical to SEQ ID NO:2. These polypeptides confer disease resistance in solanaceous plants. The isolated polynucleotides may include nucleic acid sequences that are at least 95% identical to SEQ ID NO:1. The isolated polynucleotides may encode the amino acid sequence of SEQ ID NO:2. The polynucleotides may be isolated from *Solanum verrucosum* (*S. verrucosum*). The isolated polynucleotides may encode polypeptides that confer disease resistance to oomycete pathogens, such as, for example, *Phytophthora infestans*. The isolated polynucleotides may encode polypeptides that confer disease resistance in plants selected from the group consisting of potato, tomato, and eggplant.

Vectors are provided, which include the isolated polynucleotides of the present invention. The vectors may comprise recombinant expression cassettes that include promoter sequences operably linked to polynucleotides encoding: (a) polypeptides comprising amino acid sequences that are at least 95% identical to SEQ ID NO:2; or (b) polynucleotides encoding polypeptides that comprise at least 912 amino acids of SEQ ID NO:2. These polypeptides confer disease resistance in solanaceous plants. Also provided are host cells transformed with these vectors.

Isolated polypeptides are provided, which include amino acid sequences that are at least 95% identical to SEQ ID NO:2, where the polypeptides confer disease resistance in solanaceous plants. The isolated polypeptides may include the amino acid sequence of SEQ ID NO:2. The isolated polypeptides may confer disease resistance to oomycete pathogens, such as, for example, Phytophthora infestans. Also provided are antibodies immunologically specific for the polypeptides of the present invention.

Transgenic plants are provided, which include isolated polynucleotides that encode polypeptides comprising amino acid sequences that are at least 95% identical to SEQ ID NO:2. These polypeptides confer disease resistance in the transgenic plants. The transgenic plants may be, for example, transgenic potato, tomato, or tobacco. The transgenic plants are preferably resistant to Phytophthora infestans.

Transgenic plants are also provided, which include recombinant expression cassettes comprising promoter sequences operably linked to polynucleotides, which encode polypeptides that include amino acid sequences at least 95% identical to SEQ ID NO:2. These transgenic plants express polypeptides that are encoded by the polynucleotides of the present invention. The transgenic plants of the present invention may include transgenic potato, tomato, or tobacco. The transgenic plants are preferably resistant to Phytophthora infestans.

Methods of enhancing disease resistance in solanaceous plants are provided. The methods include introducing into the solanaceous plants recombinant expression cassettes that include promoters operably linked to polynucleotides encoding polypeptides that comprise amino acid sequences that are at least 95% identical to SEQ ID NO:2. The methods may be used to enhance disease resistance in solanaceous plants such as potato, tomato, or tobacco. The methods may be used to enhance disease resistance to oomycete pathogens, such as, for example, Phytophthora infestans.

BRIEF DESCRIPTION OF THE DRAWINGS

FIG. 1 illustrates parts of the predicted $RB^{ver}$ protein sequence from Solanum verrucosum ortholog PI 275260 (SEQ ID NO: 15) and the sequences of 21 leucine-rich repeats (LRR; SEQ ID Nos: 16-36) that are repeated elements in the second part of the protein.

FIG. 2 is a multiple sequence alignment of the LRR regions of $RB^{blb}$ from Solanum bulbocastanum (SEQ ID NO: 37) and eight $RB^{ver}$ orthologs from Solanum verrucosum (PI 558485, PI 275258, PI 310966, PI 116173, PI 275256, PI 570643, PI 275260, and PI 365404; (SEQ ID NOs: 38-45 respectively ).

DETAILED DESCRIPTION OF THE PRESENTLY PREFERRED EMBODIMENTS

Figure 3:
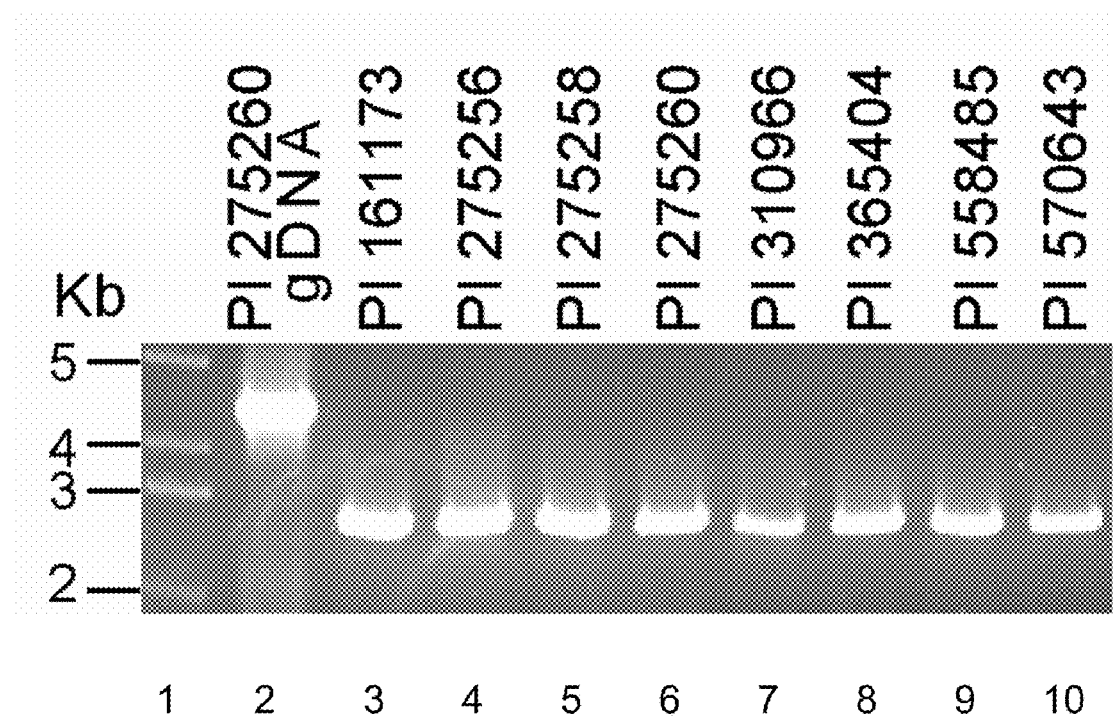
FIG. 3 is an image of an electrophoretogram showing reverse transcription-PCR (RT-PCR) products of $RB^{ver}$ orthologs, which were obtained using a pair of gene-specific primers.

The present invention is directed toward the isolation and identification of a late blight resistance gene from Solanum verrucosum, the protein that it encodes, its use for the control of plant diseases, and as a source for making transgenic plants with resistance to phytopathogenic microorganisms, in particular Phytophthora infestans. A late blight resistance gene ("RB gene"), which encodes a late blight resistance protein ("RB protein" or "RB polypeptide"), has been identified and cloned from the wild potato species Solanum verrucosum. A gene from S. verrucosum that confers late blight resistance is also herein referred to as $RB^{ver}$. For use in the present invention, the terms "RB" or "$RB^{ver}$" also refer to polymorphic variants, mutants, alleles, and interspecies homologs of the late blight resistance RB gene and protein cloned from Solanum verrucosum (i.e., $RB^{ver}$). RB genes and proteins of the present invention modulate disease resistance in plants. The RB genes and proteins of the present invention confer disease resistance in plants; in particular, they confer late blight disease resistance in solanaceous plants, including in plant species of the genus Solanum.

Generally, the nomenclature used herein and the laboratory procedures utilized in the present invention include molecular, biochemical, microbiological and recombinant DNA techniques that are well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Such techniques are thoroughly explained in the literature and are generally performed according to Sambrook et al., 1989, *Molecular Cloning—A Laboratory Manual*, Cold Spring Harbor Laboratory, Cold Spring Harbor, New York, N.Y.; Ausubel et al., 1993, *Current Protocols in Molecular Biology*, Volumes 1-3, John Wiley & Sons, Inc., Hoboken, N.J.; and Kriegler, 1990, *Gene Transfer and Expression: A Laboratory Manual*, Stockton Press, New York, N.Y.; Perbal, 1988, *A Practical Guide to Molecular Cloning*, 2nd edition, John Wiley & Sons, New York, N.Y.; Watson et al., 1992, *Recombinant DNA*, 2nd edition, Freeman & Co., New York, N.Y.; Bartlett and Stirling, 2003, *PCR Protocols*, 2nd edition, Humana Press, Totowa, N.J.; all of which are incorporated herein by reference.

It has been discovered that the wild potato species Solanum verrucosum contains in its genetic material a region with novel disease resistance genes. One or more of these genes impart resistance to pathogens, including resistance to Phytophthora infestans. Using as a starting point the RB gene sequence from Solanum bulbocastanum ($RB^{blb}$) described by Naess et al., 2000, Theor. App. Genet. 101: 697-701, the inventors isolated and identified an RB-like gene in S. verrucosum. This RB (i.e., $RB^{ver}$) late blight resistance gene from S. verrucosum is 84% identical to the S. bulbocastanum RB gene at the nucleotide level, and encodes a putative amino acid (RB polypeptide) that is 77% similar at the amino acid level to that encoded by the $RB^{blb}$ gene. The isolated and identified sequence of the $RB^{ver}$ gene from S. verrucosum has been deposited on Dec. 29, 2006 in the GenBank under accession number EF202329. The nucleic acid sequence of the late blight resistance gene RB$^{ver}$ from *S. verrucosum* is shown as SEQ ID NO:1. The amino acid sequence of the late blight resistance protein RB$^{ver}$ from *S. verrucosum*, encoded by the RB$^{ver}$ gene, is 960 amino acids long, and is shown as SEQ ID NO:2. The coding region of the late blight resistance gene RB$^{ver}$ from *S. verrucosum* is shown as SEQ ID NO:3

An "RB (also RB$^{ver}$) polynucleotide" of the present invention: (1) comprises a nucleic acid sequence that includes a coding region of from about 50 to about 10,000 nucleotides, sometimes from about 100 to about 6,000 nucleotides, and preferably from about 500 to about 4,000 nucleotides, which hybridizes to SEQ ID NO:1 or the complement thereof under stringent conditions (as defined below), and also includes conservatively modified variants thereof; (2) has substantial identity to the polynucleotide sequence of SEQ ID NO:1; and (3) encodes an RB (also RB$^{ver}$) polypeptide.

The phrase "nucleic acid" or "polynucleotide sequence" refers to a single-stranded or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

A "coding sequence" or "coding region" refers to a nucleic acid molecule having sequence information necessary to produce a gene product, when the sequence is expressed. The phrase "nucleic acid sequence encoding" refers to a nucleic acid which directs the expression of a specific protein or polypeptide. The nucleic acid sequences of this invention include both the DNA strand sequence that is transcribed into RNA and the RNA sequence that is translated into protein. The nucleic acid sequences include both the full length nucleic acid sequences as well as non-full length sequences derived from the full length sequences. It should be understood that the sequences include the degenerate codons of the native sequence or sequences which may be introduced to provide codon preference in a specific host cell.

The terms "isolated," "purified," or "biologically pure" refer to material that is substantially or essentially free from components that normally accompany it as found in its native state. Purity and homogeneity are typically determined using molecular biology and analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

In one embodiment of the present invention, provided are eight late blight resistance gene orthologs, and late blight resistance phenotypes of eight accessions of *S. verrucosum*: PI 558485, PI 275258, PI 310966, PI 116173, PI 275256, PI 570643, PI 275260, and PI 365404. "Orthologs" or "orthologous genes" are any genes in different species, which are similar to each other and originated from a common ancestor. Orthologs are typically separated by an evolutionary speciation event: if a gene exists in a species, and that species diverges into two species, then the divergent copies of this gene in the resulting species are orthologous. An "ortholog gene" may also refer to a gene with a similar function in different species. "Accession" refers to a plant or group of similar plants received from a single source at a single time.

Each accession is assigned a unique accession number (PI numbers herein). As described below, transcribed orthologs of the RB gene from eight *S. verrucosum* accessions were cloned using a homology-based PCR approach. Sequence analysis revealed that the isolated RB$^{ver}$ orthologs share up to 83.5% nucleotide identity with RB$^{blb}$ from *Solanum bulbocastanum*.

In another embodiment of the present invention, provided are isolated nucleic acids that encode polypeptides which, when produced in plants, confer disease resistance in the plants, particularly solanaceous plants, and most particularly plants from the genus *Solanum*. For example, isolated nucleic acids comprising polynucleotides at least 80% identical to a sequence as shown in SEQ ID NO:1 are provided. The present invention also provides isolated nucleic acids comprising polynucleotides at least 90% identical to a sequence as shown in SEQ ID NO:1. Yet in other examples, isolated nucleic acids comprising polynucleotides that are at least 95% identical to a sequence as shown in SEQ ID NO:1 are provided.

Also provided are isolated nucleic acids, which include polynucleotide sequences that hybridize under stringent conditions to a sequence as shown in SEQ ID NO:1 or the complement thereof, where the nucleic acids encode polypeptides that confer late blight resistance. SEQ ID NO:1 is an example of such polynucleotide sequences of the present invention. In some embodiments, the nucleic acids of the present invention encode polypeptide sequences that are at least 80% identical to the polypeptide sequence as shown in SEQ ID NO:2. In other embodiments, the nucleic acids of the present invention encode polypeptide sequences that are at least 90% identical to the polypeptide sequence as shown in SEQ ID NO:2. In yet other embodiments, the nucleic acids of the present invention encode polypeptide sequences that are at least 95% identical to the polypeptide sequence as shown in SEQ ID NO:2. The polypeptides of the present invention confer disease resistance to microbial pathogens. These microbial pathogens may include, for example, an oomycete fungus, such as *Phytophthora infestans*.

The polynucleotides of the present invention encode polypeptides useful for conferring disease resistance in plants, e.g., resistance to late blight. Methods of determining whether a polypeptide is useful for conferring disease resistance in a plant are described below.

An "RB polypeptide" of the present invention has substantial identity to the amino acid sequence of SEQ ID NO:2 and/or binds to antibodies raised against an immunogen comprising an amino acid sequence of SEQ ID NO:2. Preferred polypeptides of the present invention confer disease resistance in a plant, and in particular, confer resistance to *Phytophthora* disease-causing agents, for example *Phytophthora infestans*. SEQ ID NO:2 is an example of the polypeptides of the present invention. In addition, the polypeptides of the present invention include polymorphic variants, mutants, and interspecies homologs of SEQ ID NO:2. Polypeptides of the present invention also include functional equivalents or fragments of SEQ ID NO:2. In one embodiment, an RB polypeptide of the present invention has substantial identity to an amino acid sequence of SEQ ID NO:2 and/or is encoded by a polynucleotide that hybridizes under stringent conditions to SEQ ID NO:1 or the complement thereof, and comprises one or more of the following domains or motifs: kinase 1a or P-loop domain, kinase 2 domain, kinase 3a domain, QLPL domain, CFAY domain, MHD domain, five-heptad leucine zipper motif, four-heptad repeat motif, and 21 LRRs (leucine-rich repeats). Some of these domains or motifs are shown in the examples section below.

A functional fragment or functional equivalent or functional homolog of a polypeptide of the present invention is a polypeptide that is homologous to the specified polypeptide but has one or more amino acid differences from the specified polypeptide. A functional fragment or equivalent of a polypeptide retains at least some, if not all, of the activity of the specified polypeptide.

In general, an RB polypeptide functional homolog that preserves RB polypeptide-like function includes any homolog in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. The amino acid substitution may be a conservative substitution. Conservative substitutions whereby an amino acid of one class is replaced with another amino acid of the same type fall within the scope of the invention so long as the substitution does not materially alter the biological activity of the compound. For example, a functional equivalent of SEQ ID NO:2 shares the same amino acid sequence as SEQ ID NO:2 except for a few amino acid differences, e.g., substitutions, insertions, or deletions. When expressed in a plant, for example a plant from the Solanaceae family, both SEQ ID NO:2 and its functional homolog confer disease resistance to late blight.

Provided are promoters, as segments of an isolated nucleic acid molecule for regulating expression of genes in transformed cells, and particularly in transformed plant cells. In one example, the segments may comprise a portion of a gene that confers resistance to *Phytophthora*. These segments typically commence at a location about 2,500, and preferably about 2,000, bases upstream from a transcription initiation site of the gene that confers resistance to *Phytophthora*, and end at locations about 250 bases downstream from the transcription initiation site. These segments are capable of increasing promoter activity of homologous or heterologous promoters in plant species. In one example, the segment may include a 3' untranslated region commencing at a stop codon for the gene's coding sequence, and ending at a location about 5,000 bases downstream from the gene's transcription initiation site.

DNA segments for effecting expression of coding sequences operably linked to the segments are provided as well. These DNA segments are typically isolated from a gene whose coding region hybridizes under stringent conditions with a coding region defined by SEQ ID NO:1. The DNA segment may comprise a promoter and a transcription initiation site, and it may include a polyadenylation signal. The DNA segment may be isolated from a *S. verrucosum* RB gene.

In one embodiment of the present invention, provided are recombinant expression cassettes that include a promoter sequence operably linked to a nucleic acid of the present invention. The nucleic acid may include a polynucleotide sequence at least 80% identical to a polynucleotide sequence as shown in SEQ ID NO:1. The nucleic acid may be operably linked to the promoter in a sense or antisense orientation.

In another embodiment, provided are recombinant expression cassettes that include a promoter sequence operably linked to a nucleic acid comprising a polynucleotide sequence which hybridizes under stringent conditions to a sequence as shown in SEQ ID NO:1 or the complement thereof, where the nucleic acid encodes an RB polypeptide. The term "recombinant" when used with reference, e.g., to a cell, nucleic acid, protein, expression cassette, or vector, indicates that the cell, nucleic acid, protein, expression cassette, or vector, has been modified by the introduction of a heterologous nucleic acid or protein, or it indicates the alteration of a native nucleic acid or protein, or that the cell is derived from a cell so modified. Thus, for example, recombinant cells express genes that are not found within the native (non-recombinant) form of the cell or express native genes that are otherwise abnormally expressed, are underexpressed, or are not expressed at all.

An "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived. Preferably the recombinant expression cassette allows expression at an early stage of infection and/or it allows expression in substantially all cells of an organism, such as a plant. Examples of expression cassettes suitable for transformation of plants can be found in U.S. Pat. Nos. 5,880, 333 and 6,002,072; International Patent Publications Nos. WO/1990/002189 and WO/2000/026388; Ainley and Key, 1990, *Plant Mol. Biol.* 14: 949-967; and Birch, 1997, *Annu. Rev. Plant Physiol. Plant Mol. Biol.* 48: 297-326, all of which are herein incorporated by reference.

The term "host cell" refers to a cell from any organism. Preferred host cells are derived from plants, bacteria, yeast, fungi, insects, or other animals. The term "recombinant host cell" (or simply "host cell") refers to a cell into which a recombinant expression vector has been introduced. It should be understood that the term "host cell" is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Methods for introducing polynucleotide sequences into various types of host cells are well known in the art. Provided are host cells or progeny of host cells transformed with the recombinant expression cassettes of the present invention. The host cells may be plant cells. Preferably, the plant cells are potato cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "nucleic acid construct" or "DNA construct" is sometimes used to refer to a coding sequence or sequences operably linked to appropriate regulatory sequences and inserted into an expression cassette for transforming a cell. This term may be used interchangeably with the term "transforming DNA" or "transgene". Such a nucleic acid construct may contain a coding sequence for a gene product of interest, along with a selectable marker gene and/or a reporter gene. The term "selectable marker gene" refers to a gene encoding a product that, when expressed, confers a selectable phenotype such as antibiotic resistance on a transformed cell. The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. When the heterologous region encodes a plant gene, the gene will usually be flanked by DNA that does not flank the plant genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct" is also used to refer to a heterologous region, particularly one constructed for use in transformation of a cell.

The term "vector" is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Antisense polynucleotides are also provided. For example, the invention provides antisense oligonucleotides complementary to SEQ ID NO:1 or a fragment thereof. In one embodiment, the antisense polynucleotides are less than about 200 bases in length.

In one embodiment of the present invention, provided are transgenic plants having enhanced resistance to plant pathogens and other disease-causing agents, such as an oomycete fungus. In particular, transgenic plants having enhanced resistance to the *Phytophthora* species, e.g., *Phytophthora infestans*, are provided. Transgenic plants of the present invention may include recombinant expression cassettes comprising a promoter operably linked to a nucleic acid of the present invention. The nucleic acid can be operably linked to a promoter sequence in a sense or antisense orientation. These transgenic plants having enhanced resistance to plant pathogens may be selected from the Solanaceae family. The plant may be selected from the *Solanum* genus, and in particular the plant species may be *Solanum tuberosum*. For example, stable introduction of the RB ortholog PI 275260 from late blight resistant *S. verrucosum* into susceptible *S. tuberosum* confers resistance to *P. infestans* in *S. tuberosum*. Notably, this functional $RB^{ver}$ ortholog (PI 275260) contains an insertion of a complete leucine rich repeat when compared to $RB^{blb}$, and differs from a non-functional ortholog at only four amino acid residues.

The term "plant" includes whole plants, shoot vegetative organs/structures (e.g., leaves, stems, and tubers), roots, flowers, and floral organs/structures (e.g., bracts, sepals, petals, stamens, carpels, anthers, and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid, and hemizygous.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. The practice of the present invention contemplates a wide variety of stably transformed plant cells.

Methods are provided for enhancing disease resistance in plants. The methods include introducing a construct comprising a promoter operably linked to a nucleic acid of the present invention, and optionally, selecting for a plant with a phenotype associated with enhanced disease resistance. In some embodiments, a plant with enhanced disease resistance will be healthier and it may live longer than a wild type plant when exposed to a disease-causing agent. Enhanced disease resistance can be measured according to any method known in the art. For example, a disease symptom in a test plant can be compared to a disease symptom in a control plant following contact with a pathogen, for example *Phytophthora infestans*.

Kits are also provided for enhancing disease resistance in plants. An example of a kit according to the present invention includes a construct comprising a promoter operably linked to a nucleic acid of the present invention and instructions for producing a transgenic plant cell using the construct.

Methods of detecting RB polynucleotides in a sample are provided as well. This may be achieved by first contacting the sample with an RB polynucleotide of the present invention or a complement thereof, or contacting the sample with a polynucleotide that comprises a sequence of at least 12 nucleotides and is complementary to a contiguous sequence of an RB polynucleotide of the present invention. Then, it is determined whether a hybridization complex has been formed. In one example, the at least 12 nucleotide sequence will comprise a domain conserved among resistance (RB) genes.

Expression regulatory elements are also provided, and in particular a native promoter or variant of a native promoter from *Solanum verrucosum* that can be used to express the genes and proteins of the present invention, e.g., SEQ ID NO:1 or SEQ ID NO:1 homologs. In one embodiment, the promoter is a native promoter from *S. verrucosum* that controls expression of the RB gene.

A "nucleic acid probe" or "oligonucleotide" is defined as a nucleic acid capable of binding to a target nucleic acid of complementary sequence through one or more types of chemical bonds, usually through complementary base pairing, usually through hydrogen bond formation. As used herein, a probe may include natural bases (i.e., A, G, C, or T) or modified bases (7-deazaguanosine, inosine, etc.). In addition, the bases in a probe may be joined by a linkage other than a phosphodiester bond, so long as it does not interfere with hybridization. For example, probes may be peptide nucleic acids (PNAs) in which the constituent bases are joined by peptide bonds rather than phosphodiester linkages. It will be understood that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence (sequence fragment).

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, microinjection, in planta transformation techniques, and the like.

"Increased or enhanced expression or activity of a polypeptide of the present invention," or "increased or enhanced expression or activity of a polynucleotide encoding a polypeptide of the present invention," refers to an augmented change in activity of the polypeptide or protein. Examples of such increased expression or activity include the following: (1) activity of the protein or expression of the gene encoding the protein is increased above the level of that in wild-type, non-transgenic control plants; (2) activity of the protein or expression of the gene encoding the protein is in an organ, tissue or cell where it is not normally detected in wild-type, non-transgenic control plants (i.e., spatial distribution of the protein or expression of the gene encoding the protein is altered); (3) activity of the protein or expression of the gene encoding the protein is increased when activity of the protein or expression of the gene encoding the protein is present in an organ, tissue or cell for a longer period than in a wild-type, non-transgenic controls (i.e., duration of activity of the protein or expression of the gene encoding the protein is increased).

"Decreased expression or activity of a protein or polypeptide of the present invention," or "decreased expression or activity of a nucleic acid or polynucleotide encoding a protein of the present invention," refers to a decrease in activity of the protein. An example of such decreased activity or expression includes the decrease in activity of the protein or expression of the gene encoding the protein below the level of that in wild-type, non-transgenic control plants.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence. In the case of both expression of transgenes and inhibition of endogenous genes (e.g., by antisense or sense suppression) the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, because of codon degeneracy, a number of polynucleotide sequences will encode the same polypeptide. These variants are specifically covered by the term "polynucleotide sequence from" a particular gene. In addition, the term specifically includes sequences (e.g., full length sequences) that are substantially identical (determined as described below) with a gene sequence encoding a protein of the present invention and that encode proteins or functional fragments that retain the function of a protein of the present invention, e.g., resistance to disease-causing agents such as *Phytophthora infestans.*

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Optimal alignment of sequences for comparison may be conducted by methods commonly known in the art, for example by the search for similarity method described by Pearson and Lipman 1988, *Proc. Natl. Acad. Sci. USA* 85: 2444-2448, by computerized implementations of algorithms such as GAP, BESTFIT, BLAST, FASTA, and TFASTA in the Wisconsin Genetics Software Package, Genetics Computer Group (GCG), Madison, Wis., or by inspection. In a preferred embodiment, protein and nucleic acid sequence identities are evaluated using the Basic Local Alignment Search Tool ("BLAST"), which is well known in the art (Karlin and Altschul, 1990, *Proc. Natl. Acad. Sci. USA* 87: 2267-2268; Altschul et al., 1997, *Nucl. Acids Res.* 25: 3389-3402), the disclosures of which are incorporated by reference in their entireties. The BLAST programs identify homologous sequences by identifying similar segments, which are referred to herein as "high-scoring segment pairs," between a query amino or nucleic acid sequence and a test sequence which is preferably obtained from a protein or nucleic acid sequence database. Preferably, the statistical significance of a high-scoring segment pair is evaluated using the statistical significance formula (Karlin and Altschul, 1990). The BLAST programs can be used with the default parameters or with modified parameters provided by the user.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like. Accordingly, polynucleotides of the present invention encoding a protein of the present invention include nucleic acid sequences that have substantial identity to the nucleic acid sequence of SEQ ID NO:1.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polypeptides or proteins of the present invention include amino acid sequences that have substantial identity to the amino acid sequence of SEQ ID NO:2.

The invention also relates to nucleic acids that selectively hybridize to the exemplified sequences, including hybridizing to the exact complements of these sequences. The specificity of single-stranded DNA to hybridize complementary fragments is determined by the "stringency" of the reaction conditions (Sambrook et al, 1989). Hybridization stringency increases as the propensity to form DNA duplexes decreases. In nucleic acid hybridization reactions, the stringency can be chosen to favor specific hybridizations (high stringency), which can be used to identify, for example, full-length clones from a library. Less-specific hybridizations (low stringency) can be used to identify related, but not exact (homologous, but not identical), DNA molecules or segments.

DNA duplexes are stabilized by: (1) the number of complementary base pairs; (2) the type of base pairs; (3) salt concentration (ionic strength) of the reaction mixture; (4) the temperature of the reaction; and (5) the presence of certain organic solvents, such as formamide, which decrease DNA duplex stability. In general, the longer the probe, the higher the temperature required for proper annealing. A common approach is to vary the temperature; higher relative temperatures result in more stringent reaction conditions.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" are conditions that enable a probe, primer, or oligonucleotide to hybridize only to its target sequence (e.g., SEQ ID NO:1). Stringent conditions are sequence-dependent and will differ. Stringent conditions comprise: (1) low ionic strength and high temperature washes, for example 15 mM sodium chloride, 1.5 mM sodium citrate, 0.1% sodium dodecyl sulfate, at 50° C.; (2) a denaturing agent during hybridization, e.g. 50% (v/v) formamide, 0.1% bovine serum albumin, 0.1% Ficoll, 0.1% polyvinylpyrrolidone, 50 mM sodium phosphate buffer (750 mM sodium chloride, 75 mM sodium citrate; pH 6.5), at 42° C.; or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with a wash at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives, or analogs of the target sequence (e.g., SEQ ID NO:1). One example comprises hybridization in 6×SSC, 5×Denhardt's solution, 0.5% SDS and 100 µg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions have been described (Ausubel et al., 1993; Kriegler, 1990).

"Low stringent conditions" use washing solutions and hybridization conditions that are less stringent than those for moderate stringency, such that a polynucleotide will hybridize to the entire, fragments, derivatives, or analogs of the target sequence (e.g., SEQ ID NO:1). A nonlimiting example of low stringency hybridization conditions includes hybridization in 35% formamide, 5×SSC, 50 mM Tris HCl (pH 7.5), 5 mM EDTA, 0.02% PVP, 0.02% Ficoll, 0.2% BSA, 100 µg/ml denatured salmon sperm DNA, 10% (wt/vol) dextran sulfate at 40° C., followed by one or more washes in 2×SSC, 25 mM Tris HCl (pH 7.4), 5 mM EDTA, and 0.1% SDS at 50° C. Other conditions of low stringency, such as those for cross-species hybridizations, are well-described (Ausubel et al., 1993; Kriegler, 1990).

When expressed in a plant, the proteins of the present invention confer disease resistance in the plant. The term "disease resistance" refers to any indicia of success in the resistance of disease. A disease resistance response refers to a change in metabolism, biosynthetic activity, or gene expression, which enhances a plant's ability to suppress the replication and spread of a microbial pathogen, i.e., to resist the microbial pathogen. Examples of plant disease defense responses include, but are not limited to, production of low molecular weight compounds with antimicrobial activity (such as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase.

Agents that induce disease defense responses in plants (which are also referred to herein as "disease-causing agents") include, but are not limited to, microbial pathogens such as fungi, bacteria, and viruses. The phrase "useful for conferring disease resistance" refers to the ability to initiate a disease resistance response in a plant and subsequently confer disease resistance in the plant. Transgenic plants of the present invention having enhanced disease resistance have the ability to mount a disease resistance response to disease-causing agents, in particular to oomycete fungi, such as *Phytophthora infestans*.

The term "disease resistance genes" or "disease resistance proteins" refers to genes or their encoded proteins whose expression or synthesis confers disease resistance. In particular, disease resistance is meant to include late blight resistance.

The nucleic acids and proteins of the present invention may be isolated using methods known in the art. The genes or nucleic acid sequences encoding proteins of the present invention include genes and gene products identified and characterized by analysis using the nucleic acid sequences (including SEQ ID NO:1, SEQ ID NO:3), and protein sequences (including SEQ ID NO:2). Sequences encoding proteins of the present invention include nucleic acid sequences having substantial identity to SEQ ID NO:1. Polypeptides of the present invention include polypeptides having substantial identity to SEQ ID NO:2.

Preferred nucleic acids of the present invention encode proteins involved in disease resistance. Plant disease resistance genes frequently share a leucine-rich repeat (LRR) pattern with or without a nucleotide binding site (NBS). Such NBS-LRR genes may be similar to the Toll interleukin receptor (TIR), or they may lack significant TIR homology (non-TIR) (Ballvora et al., 2002, *Plant J.* 30: 361-371). Preferred disease resistance genes of the present invention encode polypeptides having 21 LRRs and a NBS domain.

The isolation of gene sequences that can be used in the practice of the present invention may be accomplished by a number of techniques. For instance, oligonucleotide probes based on the sequences disclosed herein can be used to identify the desired gene in a cDNA or genomic DNA library from a desired plant species. To construct genomic libraries, large segments of genomic DNA are generated by random fragmentation, for example using restriction endonucleases, and are ligated with vector DNA to form concatemers that can be packaged into the appropriate vector. The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries, or from cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Appropriate primers and probes for identifying genes encoding a protein of the present invention may be generated from comparisons of the sequences provided herein. For a general overview of PCR see *PCR Protocols*, 2003, Bartlett and Stirling, eds., $2^{nd}$ edition, Humana Press, which is herein incorporated by reference. For examples of primers used see examples section below.

Polynucleotides may also be synthesized by other well-known techniques as described in the literature (Adams et al., 1983, *J. Am. Chem. Soc.* 105: 661-663). Double-stranded DNA fragments may be obtained either by synthesizing the complementary strand and annealing the strands together under appropriate conditions, or by adding the complementary strand using DNA polymerase with an appropriate primer sequence.

One useful method to produce the nucleic acids of the present invention is to isolate and modify the nucleic acid sequences of the present invention. This can be done using methods of sequence-specific mutagenesis of a nucleic acid, for example oligonucleotide-directed mutagenesis as well as directed mutagenesis of nucleic acids using PCR. Such methods are useful to insert specific codon changes in the nucleic acids of the invention.

Once a nucleic acid is isolated using the methods described above, standard methods can be used to determine if the nucleic acid is a preferred nucleic acid of the present invention and therefore encodes a preferred protein of the present invention, by using structural and functional assays known in the art. For example, the sequence of a putative nucleic acid sequence thought to encode a preferred protein of the present invention can be compared to a nucleic acid sequence encoding a preferred protein of the present invention to determine if the putative nucleic acid is a preferred polynucleotide of the present invention.

Methods of enhancing disease resistance in plants are provided. This can be achieved by, for example, enhancing the expression of polynucleotides of the present invention in transgenic plants. In one embodiment of the invention, disease resistance is enhanced by increasing expression of a gene of the present invention in a plant. Methods of enhancing disease resistance in a plant are provided, which can be practiced by increasing or enhancing expression of the polynucleotide of SEQ ID NO:1 in a plant. A plant with enhanced disease resistance has phenotypic characteristics that are recognizable to the skilled practitioner, e.g., it has normal developmental patterns after exposure to a pathogen or has reduced symptoms following exposure to a pathogen.

Using standard methods, functional assays can be performed to determine if expression or synthesis of the putative genes or proteins confers disease resistance in a plant. For example, the methods of Naess et al., 2000, *Theor. App. Genet.* 101: 697-701, can be used to screen a transgenic plant containing a putative disease resistance gene of the present invention for late blight resistance. After transformation of a plant cell with a putative polynucleotide of the present invention and subsequent cultivation of the cell to produce a transgenic plant, the resultant transgenic plant and a control plant are sprayed to run-off with a fine mist of *P. infestans* sporangial suspension or are otherwise inoculated with the pathogen using methods known in the art. A blight scale, with 0 indicating a dead plant and 9 indicating no visible infection, is used to visually rate relative disease severity 4-5, 7, 10-11, and 14-15 days following exposure to *P. infestans*. The ratings and the ranges of percentage infections associated with the rating value are as follows: 9 equals no visible infection; 8 equals less than 10% infection; 7 equals 11-25% infection; 6 equals 26-40% infection; 5 equals 41-60% infection; 4 equals 61-70% infection; 3 equals 71-80% infection; 2 equals 81-90% infection; 1 equals greater than 90% infection; 0 equals 100% death. A transgenic plant successfully expressing a preferred gene of the present invention will have a higher score on the blight scale than a wild type plant. Such resistant transgenic plant should contain a preferred polynucleotide of the present invention.

A transgenic plant having enhanced or increased expression of a gene identical or substantially identical to a preferred polynucleotide of the present invention, e.g., SEQ ID NO:1, will typically display a phenotype associated with increased disease resistance to a disease-causing agent, such as *P. infestans*. Phenotypes associated with enhanced disease resistance to disease-causing agents can include, for example, plants with extended photosynthetic life cycles, plants with leaves that stay green for a longer duration of time, plants with an increased yield of fruit or vegetative part (e.g., tuber), plants with larger fruit, flowers, leaves, or stems, plants with improved storage ability of the tuber or other agriculturally or horticulturally significant part, and/or plants substantially lacking in disease symptoms, such as discoloration or lesions on leaves, stems, or tubers, as compared to a wild type plant, following exposure to a disease-causing agent.

Using specific promoters, the expression of a gene of the present invention can be temporally and/or spatially directed, and various types of plants with enhanced resistance to *Phytophthora infestans* can be created. For example, in some embodiments of the present invention, a tissue-specific promoter can be used to create a transgenic plant with increased resistance to *Phytophthora infestans*. The targeted tissue may be potato tuber and the tuber-specific promoter may be preferentially driving expression of the transgene in the potato tuber. Similarly, it is possible to choose from a variety of known promoters, whether constitutive, inducible, developmentally-regulated, tissue-specific, and the like, to drive expression of the polynucleotides of the present invention, thereby enhancing disease resistance in plants. Examples of useful promoters are described below. The sequences described herein can be used to prepare expression cassettes that enhance or increase endogenous or exogenous gene expression.

Any phenotypic characteristic caused by an alteration of disease resistance in a plant, for example enhanced resistance, can be selected for in the present invention. In one embodiment, after introducing a polynucleotide of the present invention operably linked to a desirable promoter (e.g., constitutive, tissue-specific, or inducible) in a plant and regenerating the plant by standard procedures, standard methods can be used to determine if the transgenic plant is a transgenic plant of the present invention, e.g., by comparing the transgenic plant to a wild type plant after exposure to a plant pathogen and looking for phenotypes associated with an alteration of disease resistance, e.g., reduced number and/or reduced size of lesions on the affected plant part.

Enhancing or increasing expression of a gene of the present invention in a plant may modulate disease resistance processes by a variety of pathways. The particular pathway used to modulate disease resistance is not critical to the present invention.

Any number of means well known in the art can be used to increase activity of a gene of the present invention in a plant. Any organ can be targeted for overexpression of a protein of the present invention, such as shoot vegetative organs/structures (e.g., leaves, stems, and tubers), roots, flowers, and floral or reproductive organs/structures (e.g., bracts, sepals, petals, stamens, carpels, anthers and ovules), seed (including embryo, endosperm, and seed coat), and fruit. Vascular or provascular tissues may be targeted. Alternatively, one or several genes described in the present invention may be expressed constitutively (e.g., using the CaMV 35S promoter).

The polypeptides encoded by the genes of the invention, like other proteins, have different domains which perform different functions. Thus, the gene sequences need not be full length, so long as the desired functional domain of the protein is expressed. If proper polypeptide expression is desired, a polyadenylation region at the 3'-end of the coding region may be included. The polyadenylation region can be derived from the natural gene, from a variety of other plant genes, or from T-DNA.

Vectors useful for practicing the present invention can be prepared using methods known in the art. Typical vectors contain transcription and translation terminators, transcription and translation initiation sequences, and promoters useful for regulation of the expression of the particular nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors may be suitable for replication and integration in prokaryotes, eukaryotes, or preferably both. Numerous vectors, bacteria, and bacteriophages that are useful for cloning may be obtained from the American Type Culture Collection (ATCC), Manassas, Va. Additional procedures for sequencing, cloning and other aspects of molecular biology and underlying theoretical considerations are also found in Watson et al., 1992, *Recombinant DNA*, Second Edition, W.H. Freeman & Co., New York, N.Y., which is herein incorporated by reference.

To use isolated sequences in the above techniques, recombinant DNA vectors suitable for transformation of plant cells are prepared. Techniques for transforming a wide variety of higher plant species are well known and described in the scientific literature, for example in Weising et al., 1988, *Annu. Rev. Genet.* 22: 421-477; and in Chrispeels et al., 2003, *Plants, Genes, and Crop Biotechnology, Second Ed.*, James and Bartlett Publishers, Sudbury, Mass., both of which are incorporated herein by reference. A DNA sequence coding for the desired polypeptide, for example a cDNA sequence encoding a full length protein, will preferably be combined with transcriptional and translational initiation regulatory sequences that will direct the transcription of the sequence from the gene in the intended tissues of the transformed plant.

Alternatively, the plant promoter may direct expression of the polynucleotide of the invention in a specific tissue (tissue-specific promoters), organ (organ-specific promoters), may be regulated during various developmental stages (developmentally-regulated promoters), or may be otherwise under more precise environmental control (inducible promoters). The above categories are not exclusive, as promoters may have various modes of temporal, spatial, and developmental regulation (e.g., both tissue specificity and developmental control). A tissue-specific promoter may drive expression of operably linked sequences in tissues other than the target tissue. Thus, a tissue-specific promoter is one that drives expression preferentially in the target tissue, but may also lead to some expression in other tissues as well. Examples of tissue-specific promoters under developmental control include promoters that initiate transcription at certain times only in certain tissues, such as fruit, seeds, flowers, pistils, or anthers. Examples of environmental conditions that may affect transcription by inducible promoters include anaerobic conditions, elevated temperature, or the presence of light.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta. Alternatively, materials and methods for producing transgenic plants containing only desired foreign genes and which are free of unwanted or irrelevant selection genes are disclosed in International Patent Application Publication No. WO/1993/001283.

Nucleic acid sequences of the present invention can be expressed recombinantly in plant cells to enhance and increase levels of endogenous plant transcription factors. A variety of different expression constructs, such as expression cassettes and vectors suitable for transformation of plant cells, can be prepared. A DNA sequence coding for a polypeptide described in the present invention can be combined, for example, with cis-acting (promoter and enhancer) transcriptional regulatory sequences to direct the timing, tissue type and levels of transcription in the intended tissues of the transformed plant. Translational control elements can also be used.

The invention provides a nucleic acid operably linked to a promoter which, in some embodiments, is capable of driving the transcription of the coding sequence in plants. The promoter can be typically derived from plant or viral sources. In construction of recombinant expression cassettes, vectors, transgenics, of the invention, different promoters can be chosen and employed to differentially direct gene expression, e.g., in some or all tissues. Typically, desired promoters are identified by analyzing the 5' sequences of a genomic clone corresponding to the genes described.

In one embodiment, a promoter or promoter fragment can be employed which will direct expression of a nucleic acid of the present invention in all transformed cells or tissues, for example as those of a regenerated plant. Such promoters are referred to herein as "constitutive" promoters and are active under most environmental conditions and states of development or cell differentiation. Examples of constitutive promoters include those from viruses which infect plants, such as the cauliflower mosaic virus (CaMV) 35S transcription initiation region (Dagless, 1997, *Arch. Virol.* 142: 183-191); the 1'- or 2'-promoter derived from T-DNA of *Agrobacterium tumefaciens* (O'Grady, 1995, *Plant Mol. Biol.* 29: 99-108); the promoter of the tobacco mosaic virus; the promoter of Figwort mosaic virus (Maiti, 1997, *Transgenic Res.* 6: 143-156); actin promoters, such as the *Arabidopsis* actin gene promoter (Huang, 1997, *Plant Mol. Biol.* 33: 125-139); alcohol dehydrogenase (Adh) gene promoters (Millar, 1996, *Plant Mol. Biol.* 31: 897-904); ACT11 from *Arabidopsis* (Huang et al., 1996, *Plant Mol. Biol.* 33: 125-139), Cat3 from *Arabidopsis* (Zhong et al., 1996, *Mol. Gen. Genet.* 251: 196-203), the gene encoding stearoyl-acyl carrier protein desaturase from *Brassica napus* (Solocombe et al., 1994, *Plant Physiol.* 104: 1167-1176), GPc1 from maize (Martinez et al., 1989, *J. Mol. Biol.* 208: 551-565), Gpc2 from maize (Manjunath et al., 1997, *Plant Mol. Biol.* 33: 97-112), and other transcription initiation regions from various plant genes (Holtorf, 1995, *Plant Mol. Biol.* 29: 637-646).

A plant promoter can direct expression of the nucleic acids described in the present invention under the influence of changing developmental conditions. Examples of developmental conditions that may affect transcription by inducible promoters include senescence and embryogenesis. Such promoters are referred to herein as "developmentally-regulated" promoters. For example, the invention incorporates the senescence-inducible promoter SAG 12 of *Arabidopsis* (Gan and Amasino, 1995, *Science* 270: 1986-1988) and the embryogenesis-related promoters of LEC1 (Lotan et al., 1998, *Cell* 93: 1195-1205), LEC2 (Stone et al., 2001, *Proc. Natl. Acad. Sci. USA* 98: 11806-11811), FUS3 (Luerssen, 1998, *Plant J.* 15: 755-764), AtSERK1 (Hecht et al., 2001, *Plant Physiol.* 127: 803-816), AGL15 (Heck et al., 1995, *Plant Cell* 7: 1271-1282), and BBM (BABYBOOM) (Boutilier et al., 2002, *Plant Cell* 14: 1737-1749).

A plant promoter can direct expression of the nucleic acids described in the present invention under the influence of changing environmental conditions. Examples of environmental conditions that may effect transcription by inducible promoters include anaerobic conditions, elevated temperature, drought, or the presence of light. Such promoters are referred to herein as "inducible" promoters, as it is possible to induce and/or increase gene transcription by manipulating the environmental conditions. For example, the invention incorporates the drought-inducible promoter of maize (Busk, 1997, *Plant J.* 11: 1285-1295); and the cold-, drought-, and high salt-inducible promoter from potato (Kirch, 1997, *Plant Mol. Biol.* 33: 897-909); in such cases, by creating drought and/or cold or high salt conditions, it is possible to express the nucleic acids of this invention. Alternatively, plant promoters which are inducible upon exposure to plant hormones, such as auxins or cytokinins, can be used to express the nucleic acids of this invention. The invention can use the auxin response elements E1 promoter fragment (AuxREs) from soybean (Liu, 1997, *Plant Physiol.* 115: 397-407); the auxin-responsive *Arabidopsis* GST6 promoter (also responsive to salicylic acid and hydrogen peroxide) (Chen, 1996, *Plant J.* 10: 955-966); the auxin-inducible parC promoter from tobacco (Sakai, 1996, 37: 906-913); a plant biotin response element (Streit, 1997, *Mol. Plant Microbe Interact.* 10: 933-937); and the promoter responsive to the stress hormone abscisic acid (Sheen, 1996, *Science* 274: 1900-1902). The invention can also use the cytokinin-inducible promoters of ARR5 and ARR6 (Brandstatter and Kieber, 1998, *Plant Cell* 10: 1009-1019), ARR2 (Hwang and Sheen, 2001, *Nature* 413: 383-389), the ethylene-responsive promoter of ERF1 (Solano et al., 1998, *Genes Dev.* 12: 3703-3714), and the β-estradiol-inducible promoter of XVE (Zuo et al., 2000, *Plant J.* 24: 265-273).

Plant promoters which are inducible upon exposure to chemical reagents that can be applied to the plant, such as herbicides or antibiotics, are also used to express the nucleic acids of the invention. For example, the maize In2-2 promoter, activated by benzenesulfonamide herbicide safeners, can be used (De Veylder, 1997, *Plant Cell Physiol.* 38: 568-577) as well as the promoter of the glucocorticoid receptor protein fusion inducible by dexamethasone application (Aoyama, 1997, *Plant J.* 11: 605-612); application of different herbicide safeners induces distinct gene expression patterns, including expression in the root, hydathodes, and the shoot apical meristem. The coding sequence of the described nucleic acids can be under the control of a tetracycline-inducible promoter, for example as described with transgenic tobacco plants containing the *Avena sativa* L. (oat) arginine decarboxylase gene (Masgrau, 1997, *Plant J.* 11: 465-473); or it can also be under the control of a salicylic acid-responsive element (Stange, 1997, *Plant J.* 11: 1315-1324).

Alternatively, inducible promoters include the tetracycline repressor/operator controlled promoter, the heat shock gene promoters, stress (e.g., wounding)-inducible promoters, defense responsive gene promoters (e.g., phenylalanine ammonia lyase genes), wound induced gene promoters (e.g., hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene). Pathogen-inducible and wound-inducible promoters include, but are not limited, to promoters of genes encoding lipoxygenases (Peng et al., 1994, *J. Biol. Chem.* 269: 3755-3761); promoters of genes encoding peroxidases (Chittoor et al., 1997, *Mol. Plant-Microbe Interactions* 10: 861-871); promoters of genes encoding hydroxymethylglutaryl-CoA reductase (Nelson et al., 1994, *Plant Mol. Biol.* 25: 401-412); promoters of genes encoding phenylalanine ammonia lyase (Yamada et al., 1994, *Plant Cell Physiol.* 35: 917-926); promoters of genes encoding glutathione-S-transferase; promoters from genes encoding chitinases (Zhu and Lamb, 1991, *Mol. Gen. Genet.* 226: 289-296); promoters from plant viral genes, either contained on a bacterial plasmid or on a plant viral vector (Hammond-Kosack et al., 1994, *Mol. Plant-Microbe Interactions* 8: 181-185); promoters from genes involved in the plant respiratory burst (Groom et al., 1996, *Plant J.* 10: 515-522); and promoters from plant anthocyanin pathway genes (Quattrochio et al., 1993, *Plant Cell* 5: 1497-1512).

The plant promoter can direct expression of the polynucleotide of the invention in a specific tissue. Such promoters are referred to herein as "tissue-specific promoters". The tissue-specific promoters are transcriptional control elements that are only active in particular cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue-specific promoters can be, e.g., ovule-specific, embryo-specific, endosperm-specific, integument-specific, seed and seed coat-specific, pollen-specific, petal-specific, sepal-specific, or some combination thereof.

Suitable seed-specific promoters may be derived from the following genes: MAC1 from maize (Sheridan, 1996, *Genetics* 142: 1009-1020); Cat3 from maize (Abler, 1993, *Plant Mol. Biol.* 22: 10131-1038); viviparous-1 from *Arabidopsis* (Suzuki et al., 2003, *Plant Physiology* 132: 1664-1667); atmyci from *Arabidopsis* (Urao, 1996, *Plant Mol. Biol.* 32: 571-57); napA and BnCysP1 from *Brassica napus* (Wan et al., 2002, *Plant J.* 30:1-10); and the napin gene family from *Brassica napus* (Sjodahl, 1995, *Planta* 197: 264-271). Fruit-specific promoters include the promoter from the CYP78A9 gene (Ito and Meyerowitz, 2000, *Plant Cell* 12: 1541-1550).

The ovule-specific BELL gene described in Reiser, 1995, *Cell* 83: 735-742, GenBank No. U39944, can also be used (Ray, 1994, *Proc. Natl. Acad. Sci. USA* 91: 5761-5765). The egg and central cell specific FIE1 promoter is also a useful reproductive tissue-specific promoter.

Sepal and petal specific promoters can also used be to express nucleic acids in a reproductive tissue-specific manner. For example, the *Arabidopsis* floral homeotic gene APETALA1 (AP1) encodes a putative transcription factor that is expressed in young flower primordia, and later becomes localized to sepals and petals (Gustafson-Brown, 1994, *Cell* 76: 131-143). A related promoter, for AP2, a floral homeotic gene that is necessary for the normal development of sepals and petals in floral whorls, is also useful (Drews, 1991, *Cell* 65: 991-1002). Another useful promoter is that controlling the expression of the unusual floral organs (ufo) gene of *Arabidopsis*, whose expression is restricted to the junction between sepal and petal primordia (Bossinger, 1996, *Development* 122: 1093-1102). A pollen-specific promoter that has been identified in maize (Guerrero, 1990, *Mol. Gen. Genet.* 224: 161-168) can also be used.

Promoters specific for pistil and silique valves, inflorescence meristems, cauline leaves, and the vasculature of stem and floral pedicels include promoters from the FUL gene (Mandel and Yanofsky, 1995, *Plant Cell* 7: 1763-1771). Promoters specific for developing carpels, placenta, septum, and ovules, may also used to express nucleic acids of the present invention in a tissue-specific manner. They include promoters from the SHP1 and SHP2 genes (Flanagan et al., 1996, *Plant J.* 10: 343-353). The pistil specific promoter in the potato (*Solanum tuberosum*) SK2 gene, encoding a pistil specific basic endochitinase (Ficker, 1997, *Plant Mol. Biol.* 35: 425-431), can also be used.

Other suitable promoters include those from genes encoding embryonic storage proteins. For example, the gene encoding the 2S storage protein from *Brassica napus* (Dasgupta, 1993, *Gene* 133: 301-302); the gene encoding oleosin 20 kD from *Brassica napus* (GenBank No. M63985); the genes encoding oleosin A (GenBank No. U09118) and oleosin B (GenBank No. U09119) from soybean; the gene encoding oleosin from *Arabidopsis* (GenBank No. Z17657); the gene encoding oleosin 18 kD from maize (Lee, 1994, *Plant Mol. Biol.* 26: 1981-1987); and the gene encoding low molecular weight sulphur rich protein from soybean (Choi, 1995, *Mol Gen. Genet.* 246: 266-268), can be used. The tissue-specific E8 promoter from tomato is particularly useful for directing gene expression so that a desired gene product is located in fruits. Suitable promoters may also include those from genes expressed in vascular tissue, such as the ATHB-8, AtPIN1, AtP5K1, or TED3 genes (Baima et al., 2001, *Plant Physiol.* 126: 643-655; Galaweiler et al., 1998, *Science* 282: 2226-2230); Elge et al., 2001, *Plant J.* 26: 561-571; Igarashi et al., 1998, *Plant Mol. Biol.* 36: 917-927).

A variety of promoters specifically active in vegetative tissues, such as leaves, stems, roots and tubers, can also be used to express the nucleic acids used in the methods of the invention. For example, promoters controlling patatin, the major storage protein of the potato tuber (Martin, 1997, *Plant J.* 11: 53-62), can be used. The ORF13 promoter from *Agrobacterium rhizogenes* which exhibits high activity in roots can also be used (Hansen, 1997, *Mol. Gen. Genet.* 254: 337-343). Other useful vegetative tissue-specific promoters include: the tarin promoter of the gene encoding a globulin from a major taro (*Colocasia esculenta* L. Schott) corn protein family, tarin (Bezerra, 1995, *Plant Mol. Biol.* 28: 137-144); the curculin promoter active during taro corm development (de Castro, 1992, *Plant Cell* 4: 1549-1559), and the promoter for the tobacco root specific gene TobRB7, whose expression is localized to root meristem and immature central cylinder regions (Yamamoto, 1991, *Plant Cell* 3: 371-382).

Leaf-specific promoters, such as the ribulose biphosphate carboxylase/oxygenase small subunit ("RuBisCO") promoter, can be used. For example, the tomato RuBisCO RBCS1, RBCS2 and RBCS3A genes are expressed in leaves and light grown seedlings, only RBCS1 and RBCS2 are expressed in developing tomato fruits (Meier et al., 1997, *FEBS Lett.* 415: 91-95). Another leaf-specific promoter is the light harvesting chlorophyll a/b binding protein gene promoter (Casal, 1998, *Plant Physiol.* 116: 1533-1538). The *Arabidopsis thaliana* myb-related gene promoter (Atmyb5) described by Li et al., 1996, *FEBS Lett.* 379: 117-121, is leaf-specific, and is expressed in developing leaf trichomes, stipules, and epidermal cells on the margins of young rosette and cauline leaves, and in immature seeds. A leaf promoter identified in maize by Busk et al., 1997, *Plant J.* 11: 1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, can be used (Di Laurenzio et al., 1996, *Cell* 86: 423-433; Long et al., 1996, *Nature* 379: 66-69). Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (Enjuto, 1995, *Plant Cell* 7: 517-527). Also useful are kn1-related genes from maize and other species which show meristem-specific expression (Granger, 1996, *Plant Mol. Biol.* 31: 373-378; Kerstetter, 1994, *Plant Cell* 6: 1877-1887). Similarly, the KNAT1 promoter from *Arabidopsis thaliana*, whose transcript is localized primarily to the shoot apical meristem and to the inflorescence stem cortex, can be used (Lincoln, 1994, *Plant Cell* 6: 1859-1876).

The invention also provides for use of tissue-specific promoters derived from viruses, which can include, for example, the tobamovirus subgenomic promoter (Kumagai, 1995, *Proc. Natl. Acad. Sci. USA* 92: 1679-1683), the rice tungro bacilliform virus (RTBV), which drives strong phloem-specific reporter gene expression; the cassaya vein mosaic virus (CVMV) promoter, with highest activity in vascular elements, in leaf mesophyll cells, and in root tips (Verdaguer, 1996, *Plant Mol. Biol.* 31: 1129-1139).

In another embodiment, a nucleic acid described in the present invention is expressed through a transposable element. This allows for constitutive, yet periodic and infrequent expression of the desired polypeptide.

Native promoters from *Solanum verrucosum* are provided. In particular, disease resistance promoters from *Solanum verrucosum* are provided, which are capable of controlling expression of the genes of the present invention. A disease resistance promoter from *Solanum verrucosum* is a promoter derived from a *Solanum verrucosum* disease resistance gene, for example by cloning, isolating, or modifying a native promoter from a disease resistance gene. The provided promoters can be used to initiate gene expression in a plant cell.

Preferred promoters of the present invention can control expression of the $RB^{ver}$ gene. Accordingly, the preferred promoters can control expression of genes comprising coding regions that have substantial identity to the coding region of SEQ ID NO:1, for example genes that have at least 70%, 80%, 90%, 95%, 95%, 97%, 98%, 99%, or 100% identity to the coding regions of SEQ ID NO:1.

A promoter sequence of the present invention can be identified, for example, by analyzing the 5', or in some instances 3', region of a genomic clone corresponding to the disease resistance genes described herein. Sequence characteristic of promoter sequences can be used to identify the promoter. Sequences controlling eukaryotic gene expression have been extensively studied. For instance, promoter sequence elements include the TATA box consensus sequence, which is upstream of the transcription start site. In most instances the TATA box is required for accurate transcription initiation. In plants, further upstream from the TATA box, there may also be a CCAAT box, and/or additional promoter elements that are required for full promoter activity. A number of methods are known for identifying and characterizing promoter regions in plant genomic DNA (An et al., 1986, *Mol. Gen. Genetics* 203: 245-250; Jordano et al., 1989, *Plant Cell* 1: 855-866; Meier et al., 1991, *Plant Cell* 3: 309-316; Zhang et al., 1996, *Plant Physiology* 110: 1069-1079).

Transgenic plants comprising expression cassettes or vectors, which include a *Solanum verrucosum* promoter operably linked to a nucleic acid of the present invention, are also provided. The promoters and nucleic acids can be operably linked using standard recombinant techniques. The promoter may be homologous or heterologous to the nucleic acid. Preferably, expression of the nucleic acids of the present invention under the control of the promoter will increase survival of the plant in response to infection with a microbial pathogen, and in particular, in response to *P. infestans*. Promoter activity can be measured, for example, by measuring the difference upon contact or infection with a pathogen such as *P. infestans* in mRNA transcribed by genes under the control of the promoter, in comparison to untransformed control plants.

Transgenic plants of the present invention can be prepared using methods known in the art. DNA constructs of the invention may be introduced into the genome of a desired plant host by a variety of conventional techniques. For example, the DNA construct may be introduced directly into the genomic DNA of the plant cell using techniques such as microinjection and electroporation of plant cell protoplasts, or the DNA constructs can be introduced directly into plant tissue using biolistic methods, such as DNA particle bombardment. Plant cell microinjection techniques are known in the art and well described in the scientific and patent literature, for example in U.S. Pat. No. 4,743,548. The introduction of DNA constructs using polyethylene glycol precipitation is described in Paszkowski et al., 1984, *EMBO J.* 3: 2717-2722. Electroporation techniques are described in Fromm et al., 1985, *Proc. Natl. Acad. Sci. USA* 82: 5824-5828. Biolistic transformation techniques are described in Klein et al., 1987, *Nature* 327: 70-73. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature (Horsch et al, 1984, *Science* 233: 496-498; Gelvin, 2003, *Microb. Mol. Biol. Reviews* 67:16-37). Other species of bacteria outside the *Agrobacterium* genus can also be used for gene transfer into plants (Broothaerts et al., 2005, *Nature* 433: 629-633).

Transformed plant cells which are derived by any of the above transformation techniques can be cultured to regenerate a whole plant which possesses the transformed genotype and thus the desired phenotype. Regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Binding, 1985, *Regeneration of Plants, Plant Protoplasts*, pp. 21-73, CRC Press, Boca Raton, Fla., which is herein incorporated by reference. Regeneration can also be obtained from plant callus, explants, organs, or parts thereof. Such regeneration techniques are described generally in Klee et al., 1987, *Annu. Rev. Plant Physiol.* 38: 467-486.

The nucleic acids of the invention can be used to confer desired traits, i.e., to confer disease resistance, on essentially any plant. Thus, the invention has use over a broad range of plants, monocots and dicots, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and *Zea*. Examples include tobacco and *Arabidopsis*, cereal crops such as maize, wheat, rice, soybean barley, rye, oats, sorghum, alfalfa, clover and the like, oil-producing plants such as canola, safflower, sunflower, peanut and the like, vegetable crops such as tomato tomatillo, potato, pepper, eggplant, sugar beet, carrot, cucumber, lettuce, pea and the like, horticultural plants such as aster, begonia, chrysanthemum, delphinium, zinnia, lawn and turfgrasses and the like.

The disease resistance genes and proteins of the present invention are particularly useful for conferring disease resistance in solanaceous plants, such as plants of the Solanaceae family, in particular in the genus *Solanum*, and further in particular in the cultivated variety of potato, *Solanum tuberosum*. Additional examples of solanaceous plants include eggplant, potato, tomato, and the like. In some embodiments, the disease resistance genes and proteins of the present invention are useful for conferring disease resistance in any plant infected by a *Phytophthora* species including, but not limited to, grape plants, avocado plants, and fruit and nut tree varieties. In particular, the transgenic plants expressing the genes and proteins of the present invention exhibit enhanced disease resistance to *Phytophthora infestans*.

In one example, after introduction of the expression cassette into a plant, the plants are screened for the presence of the transgene and crossed to an inbred or hybrid line. Progeny plants are then screened for the presence of the transgene and self-pollinated. Progeny from the self-pollinated plants are grown. The resultant transgenic plants can be examined for any of the phenotypic characteristics associated with altered disease resistance characteristics, for example healthier leaves following exposure to a pathogen. Using the methods of the present invention, overexpression of the nucleic acids and/or proteins described in the present invention is used to enhance disease resistance. Standard methods can be used to determine if a plant possesses the characteristics associated with enhanced disease resistance. For example, a late blight scoring system can be used to determine if a plant has enhanced resistance to *Phytophthora infestans*. In a preferred embodiment, the transgenic plants have enhanced disease resistance to late blight. Transgenic plants transformed with the RB gene can be tested, recording foliage blight scores 69, 92, 116, and 163 hours after inoculation. The average resistant score for transgenic plants with the RB gene is then determined, and is compared to the average resistant score of untransformed control plants.

Using known procedures, screens for plants of the invention can be performed by detecting increased or decreased levels of the claimed gene and claimed protein in a plant and detecting the desired phenotype. Means for detecting and quantifying mRNA or proteins are well known in the art, such as Northern blots, RT-PCR, DNA microarrays, Western blots, or protein activity assays. Gene amplification and/or expression can be measured in a sample directly, for example, by conventional Southern blotting, Northern blotting to quantitate the transcription of mRNA, dot blotting (DNA analysis), DNA microarrays, or in situ hybridization, using an appropriately labeled probe, based on the sequences provided herein. Various labels can be employed, most commonly radioisotopes, particularly $^{32}$P. However, other techniques can also be employed, such as using biotin-modified nucleotides for introduction into a polynucleotide. The biotin then serves as the site for binding to avidin or antibodies, which can be labeled with a wide variety of labels, such as radionuclides, fluorescers, enzymes, or the like. Alternatively, antibodies can be employed that can recognize specific duplexes, including DNA duplexes, RNA duplexes, and DNA-RNA hybrid duplexes, or DNA-protein duplexes. The antibodies in turn can be labeled and the assay can be carried out where the duplex is bound to a surface, so that upon the formation of duplex on the surface, the presence of antibody bound to the duplex can be detected. Gene expression, alternatively, can be measured by immunological methods, such as immunohistochemical staining. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. Gene expression can also be measured using DNA microarrays, commonly known as gene chips.

Provided are antibodies immunologically specific for all or part, e.g., an amino-terminal portion, of polypeptides of the present invention. The term "antibodies" as used herein includes polyclonal and monoclonal antibodies, chimeric, and single chain antibodies, as well as Fab fragments, including the products of a Fab or other immunoglobulin expression library. With respect to antibodies, the term "immunologically specific" refers to antibodies that bind to one or more epitopes of a protein of interest, but which do not substantially recognize and bind other molecules in a sample containing a mixed population of antigenic biological molecules. Antibodies immunologically specific for part or all of the polypeptides of the present invention, e.g., SEQ ID NO:2 or a fragment thereof, are provided as well. For example, the antibodies may be immunologically specific for polypeptides that are at least 80% identical to a sequence as shown in SEQ ID NO:2, or they may be immunologically specific for polypeptides that are at least 90% identical to a sequence as shown in SEQ ID NO:2. The antibodies may be immunologically specific for all or part, e.g., an amino-terminal portion, of an RB polypeptide encoded by an isolated nucleic acid that hybridizes under stringent conditions to a sequence as shown in SEQ ID NO:1 or the complement thereof. Accordingly, isolated antibodies or antibody compositions that specifically bind to a polypeptide having the amino acid sequence as shown in SEQ ID NO:2 are provided. In some embodiments, the antibodies may be monoclonal. Alternatively, the antibodies may be polyclonal. The antibodies of the present invention may be labeled using methods known in the art. A "label" is a composition detectable by various means, for example by spectroscopic, photochemical, biochemical, immunochemical, or chemical means. Useful labels include $^{32}$P, fluorescent dyes, electron-dense reagents, enzymes (e.g., as commonly used in an ELISA), biotin, digoxigenin, or proteins for which antisera or monoclonal antibodies are available.

Also provided are methods of detecting RB polypeptides in a sample, by way of contacting the sample with an anti-RB antibody of the present invention, and subsequently determining whether a hybridization complex has been formed between the antibody and the polypeptide.

The polypeptides of the present invention may be used alone or in combination with other proteins or agents to enhance disease resistance. Other agents to enhance disease resistance include, for example, fungicides.

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

EXAMPLES

*Phytophthora infestans* Strains and Culture Conditions

*Phytophthora infestans* isolate US 940480 (A2 mating type, race 0.1.2.3.4.5.6.7.10.11) was obtained from Barbara Baker (USDA/ARS, Albany, Calif.). *P. infestans* isolates were routinely cultured at 15° C. on rye A agar medium supplemented with 2% sucrose (Caten and Jinks, 1968, *Can. J. Bot.* 46: 329-347). Washes using sterile distilled water were combined to obtain a sporangia count of the desired concentration. Sporangial suspensions were placed at 12° C. for 1.5 to 3 hours to induce zoospore hatching.

Plant Growth Conditions

Seeds for *S. verrucosum* accessions (PI numbers 161173, 275256, 275258, 275260, 310966, 365404, 558485, and 570643) were obtained from the National Research Support Program-6 (NRSP-6) potato genebank in Sturgeon Bay, Wisconsin. Seedlings were grown under greenhouse conditions (23° C. day/15° C. night temperatures with 14 hours of light) and watered as needed.

Preparation of Genomic DNA and RNA

Potato genomic DNA was isolated from leaves of the eight *S. verrucosum* accessions described herein according to Dellaporta et al., 1983, *Mol. Biol. Rep.* 1: 19-21. DNA samples were checked for purity and integrity using spectrophotometry and gel electrophoresis. Total RNA was extracted from young leaves of the eight *S. verrucosum* accessions using the GenElute™ Total RNA Purification Kit (Sigma-Aldrich, St. Louis, Mo.). Contaminating DNA was removed from the RNA preparations using TURBO DNA-Free™ (Applied Biosystems/Ambion, Austin, Tex.). The concentration and quality of RNA samples were determined using an Experion™ RNA HighSens Analysis Kit (Bio-Rad Laboratories, Hercules, Calif.).

Primer Design, PCR Amplification, and Reverse Transcription-PCR Analyses

Total genomic DNA was extracted from eight *S. verrucosum* accessions: PI161173; PI 275256; PI 275258; PI 275260; PI 310966; PI 365404; PI 558485; PI 570643. DNA samples were checked for purity and integrity using spectrophotometry.

A pair of oligonucleotide primers—F1, which is 5'-CTT CCC ATT TCA TTC CAA CTA GCC-3' (SEQ ID NO:4) and R14, which is 5'-CCT TCT CAC ACC GCT TGA TCA G-3' (SEQ ID NO:5)—were designed for the amplification of a 3624 nt fragment of the *S. bulbocastanum* RB gene. PCR amplification was performed on total genomic DNA from the eight *S. verrucosum* accessions using Platinum® PCR SuperMix High Fidelity (Invitrogen, Carlsbad, Calif.). The PCR conditions were: 1 min at 94° C. followed by 40 cycles of 15 sec at 94° C., 30 sec at 52° C., 5 min at 68° C., and 15 min at 68° C. The PCR products were purified using the Wizard® SV Gel and PCR Clean-Up System (Promega, Madison, Wis.) and ligated into the pGEM®-T Easy Vector (Promega) before cloning and sequence analysis. The PCR product amplified from *S. verrucosum* accession PI 275260 was digested with NotI and ligated into the NotI site of the pBluescript KS+ vector. It was then cut with BamHI and SacI and ligated into BamHI and SacI digested binary vector pBI121 (Clontech, Mountain View, Calif.).

Reverse transcription (RT) PCR was carried out using the SuperScript™ III First-Strand Synthesis System for RT-PCR (Invitrogen) followed by PCR amplification of the first-strand cDNA product using primer pairs: F3, which is 5'-TCA AGC CGT CCT TGA AGA TGC TCA G-3' (SEQ ID NO:6); and R3, which is 5'-GGC GAA ACC AAT GGA CAT CAT ATG-3' (SEQ ID NO:7). The PCR products were purified using Wizard® SV Gel and PCR Clean-Up System (Promega).

Full Length RB-Orthologous Gene Construction

In one example, a fragment amplified from *S. verrucosum* did not encode the complete C-terminal of the polypeptide. Therefore, a complete open reading frame of RB$^{ver}$ from accession PI 275260 was constructed using splicing by overlap extension (SOE) of the *S. verrucosum* and *S. bulbocastanum* RB genes. One 3962 bp intermediate fragment was amplified from *S. verrucosum* accession PI 275260 in pBI121 using the primers 35S for, which is 5'-GTA AGG GAT GAC GCA CAA TC-3' (SEQ ID NO:8) and RBver-SOErev, which is 5'-GCC AGT CTT CTC CTA TTC CCT TCT CAC ACC GCT TGA TCA-3' (SEQ ID NO:9), and Platinum® PCR SuperMix High Fidelity (Invitrogen). The other 397 bp intermediate fragment was amplified from *S. bulbocastanum* RB cDNA in pBI121 using the primers RB-SOEfor, which is 5'-TAA TTA CTC AAT GTC CAA TAG TGA TCA AGC GGT GTG AGA AGG-3' (SEQ ID NO:10) and nosrev, which is 5'-CGT CAT GCA TTA CAT GTT AA-3' (SEQ ID NO:11).

SOE was performed by mixing the PCR products of the two intermediate fragments at a ratio of 1:10 (RB$^{ver}$:RB$^{blb}$), followed by PCR using primers 35Sfor (SEQ ID NO:8) and nosrev (SEQ ID NO:11). The PCR conditions were: 1 min at 94° C. followed by 40 cycles of 15 sec at 94° C., 30 sec at 52° C., 5 min at 68° C., and 15 min at 68° C. for both intermediate amplification and overlap extension. The PCR product of the complete *S. verrucosum* RB-like SOE fragment was cloned into a pGEM®—T Easy Vector and digested with BamHI and XmnI for cloning into pBI121.

Sequence and Clustering Analysis

Double-strand sequencing of DNA was carried out at the University of Wisconsin-Madison Biotechnology Center sequencing facility. Sequence analyses were performed as follows: ambiguous calls were checked against chromatograms using the program ContigExpress (Invitrogen); similarity searches were implemented locally on a Mac OSX workstation using BLAST; open reading frames of the eight RB$^{ver}$ orthologs were translated into amino acid sequences using the program Vector NTI Explorer (Invitrogen); multiple sequence alignments of the eight RB$^{ver}$ orthologous proteins with other RB proteins were conducted using the program CLUSTAL-X (Thompson et al., 1997, Nucl. Acids Res. 2524: 4876-4882); PAUP v4.0b10 (Sinauer Associates, Sunderland, Mass.) was used to reconstruct a phylogenetic tree using the neighbor-joining method with 1,000 bootstrap replications; alternative topology was viewed with the program TreeView PPC 1.6.6, obtained from the University of Glasgow, UK.

Sequences of the eight isolated RB orthologs from S. verrucosum have been deposited in the GenBank under the following accession numbers: EF202326 (PI 116173); EF202327 (PI 275256); EF202328 (PI 275258); EF202329 (PI 275260); EF202330 (PI 310966); EF202331 (PI 365404); EF202332 (PI 558485); and EF202333 (PI 570643).

Diversifying Selection Analysis

The rate of nonsynonymous nucleotide substitutions per nonsynonymous site ($d_N$) and the rate of synonymous nucleotide substitutions per synonymous site ($d_S$) across all the amino acid sites in pairwise comparisons between nucleotide sequences were estimated using the approximate method of Nei and Gojobori, 1986, Mol. Biol. Evol. 35: 418-426, which was implemented in the YN00 program of the PAML software package (Yang, 1997, Comput. Appl. Biosci. 13: 555-556). In addition, maximum likelihood models of codon substitution were used, which allowed for heterogeneous selection pressures among sites along the protein to identify which amino acids were affected by diversifying selection. Detailed analysis was conducted as described by Liu et al., 2005, Mol. Biol. Evol. 223: 659-672.

Complementation Analysis

Transformation of potato plants with the isolated RB polynucleotide or its fragments was performed. Potato (cv. Katahdin) transformation with a polynucleotide fragment corresponding to the RB gene (RB-like SOE fragment) in the binary vector pBI121 was performed by the Biotechnology Center, University of Wisconsin-Madison. This polynucleotide fragment was mobilized into Agrobacterium tumefaciens LBA4404 for plant transformation. Internodes were taken from three- to four-week-old in vitro grown potato plants cv. Katahdin maintained on PROP medium (Haberlach et al., 1985, Plant Sci. Lett. 39: 67-74). Explants are placed in a suspension of Agrobacterium (4-6×10$^8$ cells/ml) for 30 min, blotted and transferred to ZIG medium (Clearly, 1997, Am. Pot. Journal 74: 125-129) for a 4 day cocultivation. Internodes were then moved to ZIG medium containing 50 mg/L kanamycin to select for transformants and 250 ml/L cefataxine to suppress growth of Agrobacterium. Putative transgenic plantlets were removed from explant pieces 10 to 16 weeks later and rooted on PROP medium.

In one example, Agrobacterium-mediated potato (Solanum tuberosum cv. Katahdin) transformation of the RB$^{ver}$ gene (from accession PI 275260) in pBI121 was performed by the Plant Biotechnology Center at the University of Wisconsin-Madison. To confirm Kanamycin-resistant transgenic plants, PCR amplification with the transgene-specific primers was performed, using: KanFor1, which is 5'-CGC TTG GGT GGA GAG GCT ATT C-3' (SEQ ID NO:12) and KanRev1, which is 5'-AGG AAG CGG TCA GCC CAT TC-3' (SEQ ID NO:13). Six-week old plants with confirmed insertions of RB$^{ver}$ were screened and scored for late blight resistance under greenhouse conditions.

Screening for Late Blight Disease Resistance

Whole-plant disease resistance assays were initiated on five different days. Eight-week-old seedlings were placed in a misting chamber (100% humidity, 18° C., 14 hours of light) and were sprayed to run-off with a fine mist of Phytophthora infestans sporangial suspension prepared from US-8, Type A2, Cornell standard ME 93-A2 (WEF#US930287) cultures maintained on rye A medium in a greenhouse facility. The suspension contained approximately 75,000 sporangia/ml and was pre-chilled for 4 h at 10° C. before use. Relative humidity in the greenhouse was maintained at or above 90%. The temperature was maintained at 23° C. during daylight hours (15 h) and dropped to 15° C. at night (9 h).

Foliage blight scores were recorded 69, 92, 116, and 163 hours after inoculation. A blight scale, with 0 indicating a dead plant and 9 no visible infection, was used to visually rate disease severity. All the plants were tested in three repetitions. The ratings and the ranges of percentage infections associated with the rating value are as follows: 9, no visible infection; 8, less than 10% infection; 7, 11-25% infection; 6, 26-40% infection; 5, 41 to 60% infection; 4, 61-70% infection; 3, 71-80% infection; 2, 81-90% infection; 1, greater than 90% infection; 0, all dead (scale according to Colton et al., 2006, Crop Sci. 462: 589-594).

Plants with scores of 8 or above were scored as resistant to late blight and plants with scores of 6.9 or below were scored as susceptible to late blight. Plants with scores between 6.9 and 8 were scored as intermediate resistant.

S. verrucosum Accessions Vary in their Resistance to P. infestans

Late blight resistance levels of eight S. verrucosum accessions were examined using greenhouse inoculations of whole plants. Whole plant inoculations of the eight S. verrucosum accessions were carried out in an environmentally controlled greenhouse, which maintained the relative humidity at or above 90%. Each accession was spray-inoculated with a suspension containing 75,000 sporangia/ml of P. infestans and repeated on five separate dates.

In Table 1, six-week old seedlings were placed in a misting chamber (approximately 100% humidity, 18° C.) and spray inoculated with sporangia from the US 940480 strain of P. infestans. Plants were scored 10 days after inoculation. The late blight resistance score was calculated based on observation of diseased leaf tissue: 0=100% diseased tissue, 8=<10% diseased tissue.

TABLE 1

Testing of S. verrucosum accessions for resistance to late blight

| Accession | Late blight score |
|---|---|
| PI 161173 | 6.6 ± 1.1 |
| PI 275256 | 7.0 ± 0.7 |
| PI 275258 | 6.8 ± 0.8 |
| PI 275260 | 7.4 ± 0.5 |
| PI 310966 | 6.2 ± 1.1 |
| PI 365404 | 6.6 ± 0.5 |
| PI 558485 | 6.6 ± 1.1 |
| PI 570643 | 3.2 ± 1.6 |

Most accessions of S. verrucosum displayed high levels of resistance (Table 1). Accession PI 275260 consistently exhibited the strongest resistance to P. infestans with an average resistance score of 7.4±0.5 (0=100% infection, 8=<10% infection). Only PI 570643 exhibited moderate susceptibility to late blight, with a resistance score averaging 3.2±1.6. This accession consistently displayed spreading lesions with water-soaked areas on its lower and upper leaves. Any disease progression on other *S. verrucosum* accessions was limited to the lower leaves, with little chlorosis and leaf senescence observed.

*S. verrucosum* Accessions Contain Transcribed RB Orthologous Genes

With primers specific for the *S. bulbocastanum* RB gene, PCR was performed using genomic DNA from all eight tested *S. verrucosum* accessions. Unique products, ranging between 3902 and 3916 nt, were amplified and cloned from each accession. Sequencing analysis revealed the presence of only one PCR product from each accession. These products were highly similar to the corresponding $RB^{blb}$ sequence, suggesting the presence of an RB-like gene in each of these accessions. Sequence analysis also revealed that the amplified products contained 94 nt of the 5' transcript leader region as well as the AUG start codon. However, no 3' primer suitable for amplification of the entire open reading frame was identified. Therefore, each PCR product lacked 50 nt at the 3' end of the coding region. RB orthologs from *S. verrucosum* accessions PI 116173, PI 275256, PI 275258, PI 310966, and PI 558485 contained a 7-bp frame-shift deletion located 1011 nt downstream of the AUG start codon. Accession PI 365404 contained a 1-bp frame-shift deletion 868 nt downstream of the AUG. Each of these frame-shift mutations results in predicted protein sequences that are truncated with respect to $RB^{blb}$. Based on sequence similarity to the $RB^{blb}$ gene, both accessions PI 275260 and PI 570643 encode potentially full-length CC-NBARC-LRR proteins of 960 amino acids. Complementation analysis demonstrated that the RB ortholog from *S. verrucosum* PI 275260 is a functional RB gene that confers late blight resistance to *P. infestans*.

FIG. 1 illustrates the RB orthologous protein sequence from *S. verrucosum* PI 275260. The three predicted kinase motifs of the NBS domain (kinase 1a/P-loop; kinase 2a; and kinase 3a) are shown above the sequence. Amino acid residues under diversifying selection are shaded in grey.

The bottom part of FIG. 1 illustrates the LRR domains of the predicted RB protein sequence from *Solanum verrucosum* ($RB^{ver}$) ortholog PI 275260. The residues involved in the extra LRR region from *S. verrucosum* are underlined in LRR 16 and LRR 17. The LRR regions were aligned based on the consensus sequence LXXLXXLXXLXLXXN/CXXLXX-LXX (SEQ ID NO:14), where X represents any amino acid.

Nucleotide sequences of the $RB^{ver}$ orthologs are up to 83.4% identical to $RB^{blb}$ and have conserved intron-exon structures. The predicted proteins from *S. verrucosum* contain several insertions or deletions (indels) and share between 82% and 82.6% amino acid identity with the $RB^{blb}$ protein sequence (Table 2). In Table 2, nucleotide identity percentages are shown above the diagonal line. Amino acid identity percentages are shown below the diagonal line. Only the exon sequences were used.

Figure 2A:
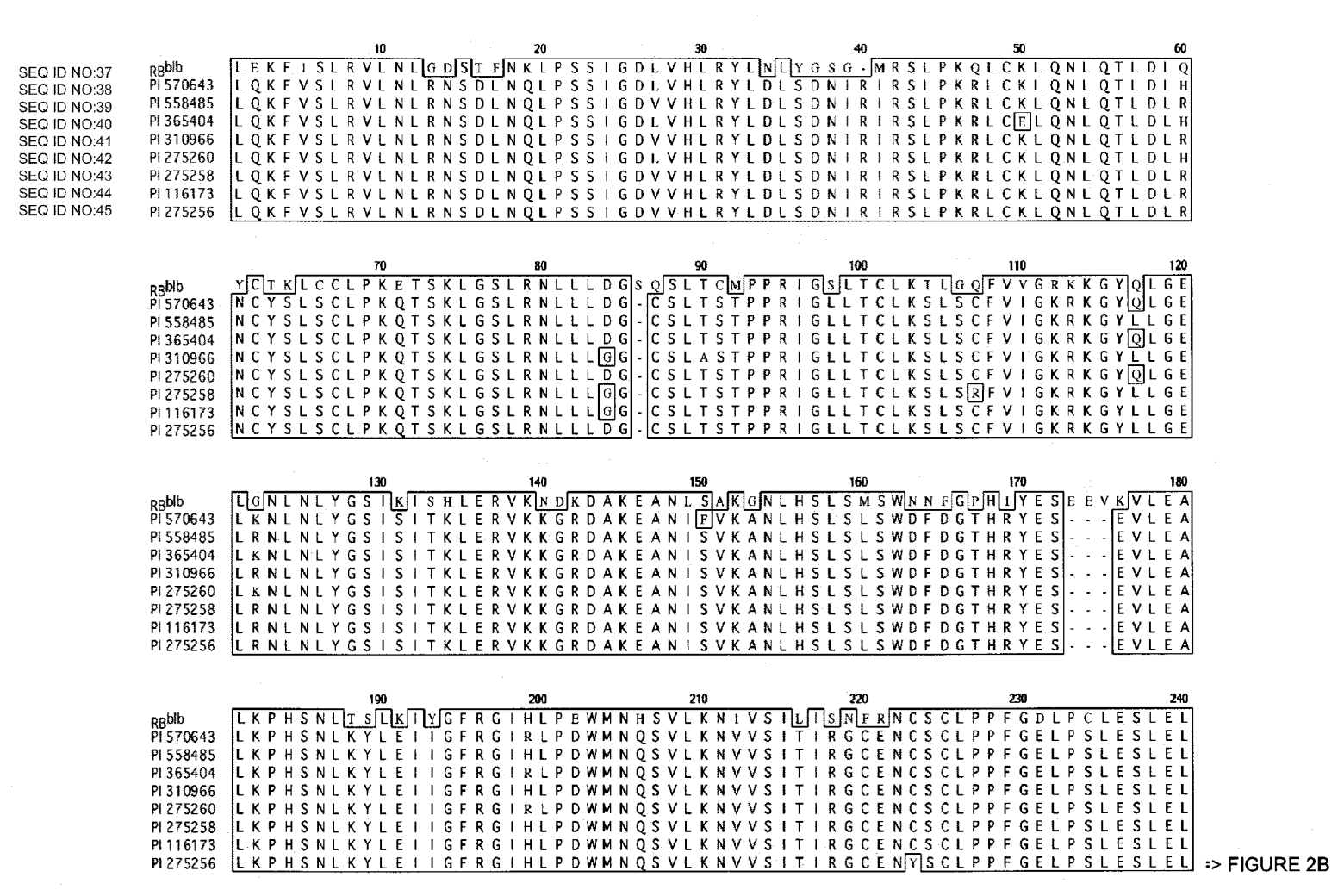
Figure 2B:
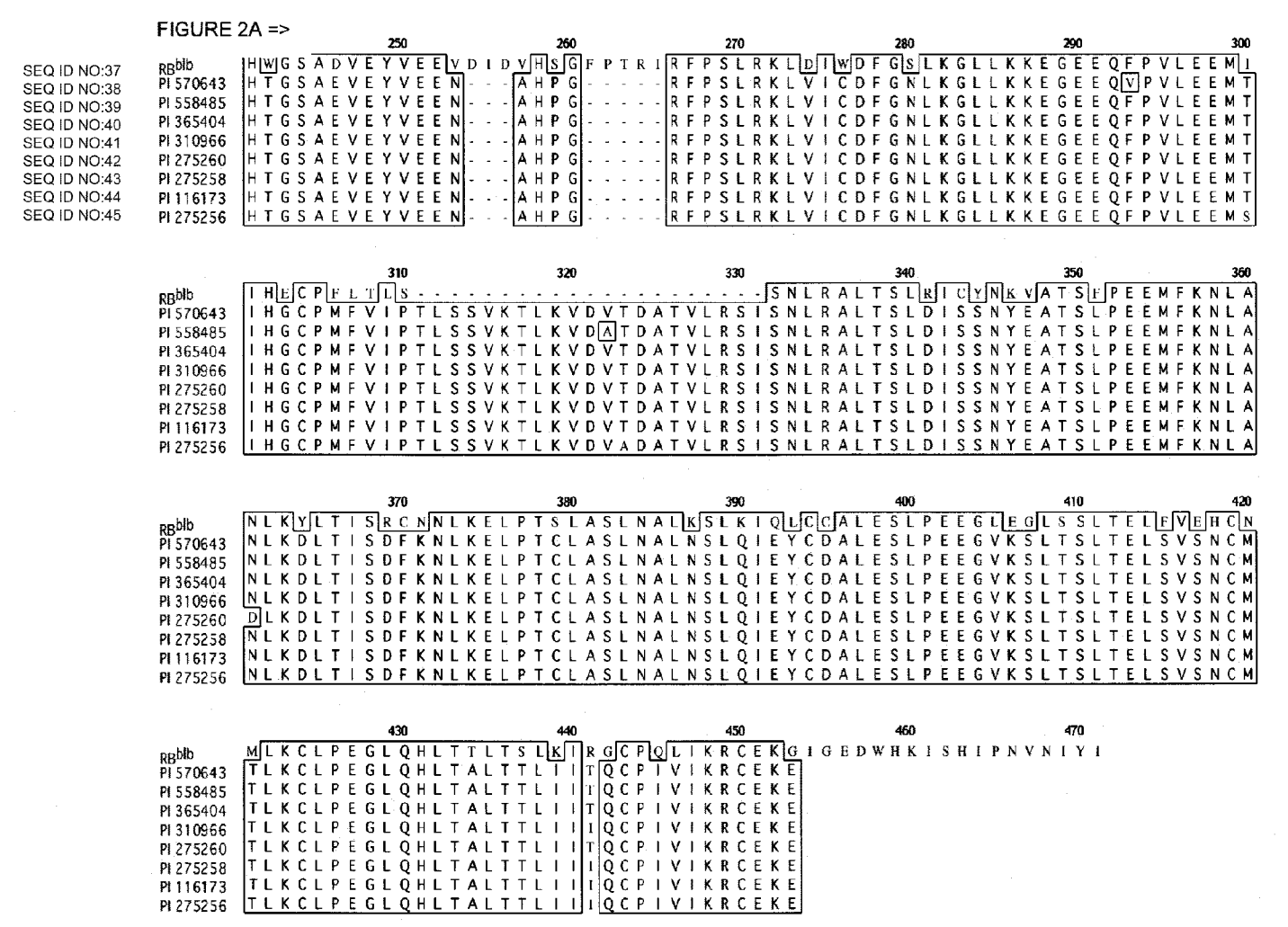

The predicted protein from *P. infestans* resistant accession PI 272560 is 82.4% identical to $RB^{blb}$. Interestingly, as shown in FIG. 2, the comparison of the leucine rich repeat regions between $RB^{blb}$ and $RB^{ver}$ orthologs identified an insertion of a 21 amino acid complete LRR, but no frame-shift. FIG. 2 illustrates multiple sequence alignment of the LRR regions of the eight $RB^{ver}$ orthologs from *S. verrucosum* and $RB^{blb}$. Single-letter amino acid codes were used. The sequence alignment shown in FIG. 2B represents continuation of the sequence alignment shown in FIG. 2A.

TABLE 2

Pairwise comparison of nucleotide and amino acid identities among $RB^{ver}$ and $RB^{blb}$ genes

| | $RB^{blb}$ | PI 161173 | PI 275256 | PI 275258 | PI 275260 | PI 310966 | PI 365404 | PI 558485 | PI 570643 |
|---|---|---|---|---|---|---|---|---|---|
| $RB^{blb}$ | | 88.9 | 88.9 | 88.9 | 88.8 | 88.7 | 88.8 | 88.9 | 88.8 |
| PI 161173 | 82.2 | | 99.7 | 99.9 | 98.3 | 99.7 | 98.3 | 99.5 | 98.3 |
| PI 275256 | 82.2 | 99.4 | | 99.6 | 98.2 | 99.4 | 98.2 | 99.3 | 98.2 |
| PI 275258 | 82.1 | 99.4 | 98.9 | | 98.2 | 99.6 | 98.2 | 99.3 | 98.2 |
| PI 275260 | 82.4 | 97.3 | 97.0 | 97.1 | | 98.1 | 99.8 | 98.6 | 99.7 |
| PI 310966 | 82.0 | 99.4 | 98.9 | 99.2 | 97.1 | | 98.0 | 99.2 | 98.0 |
| PI 365404 | 82.3 | 97.2 | 96.9 | 97.0 | 99.7 | 97.0 | | 98.5 | 99.7 |
| PI 558485 | 82.6 | 99.1 | 98.8 | 98.9 | 97.8 | 98.9 | 97.7 | | 98.5 |
| PI 570643 | 82.4 | 97.3 | 97.0 | 97.1 | 99.6 | 97.1 | 99.5 | 97.8 | |

To examine whether the $RB^{ver}$ genes are transcribed, gene-specific RT-PCR was performed on the first-strand cDNA products synthesized from total RNA extracted from the eight *S. verrucosum* accessions. As shown in FIG. 3, all the eight examined $RB^{ver}$ genes were transcribed in the absence of pathogen challenge. Specifically, FIG. 3 is an image showing reverse transcription PCR of the $RB^{ver}$ orthologs using a pair of gene-specific primers. Lane 1: DNA ladder. Lane 2: a genomic DNA copy (gDNA) of the $RB^{ver}$ gene from PI 275260, including the 928 nt intron, was used as a template. Lanes 3-10: total RNA from the indicated accessions was used as a template for cDNA production and subsequent PCR reactions (lane 3, PI 161173; lane 4, PI 275256; lane 5, PI 275258; lane 6, PI 275260; lane 7, PI 310966; lane 8, PI 365404; lane 9, PI 558485; lane 10, PI 570643).

Phylogenetic Analysis of RB Orthologs

Figure 4:
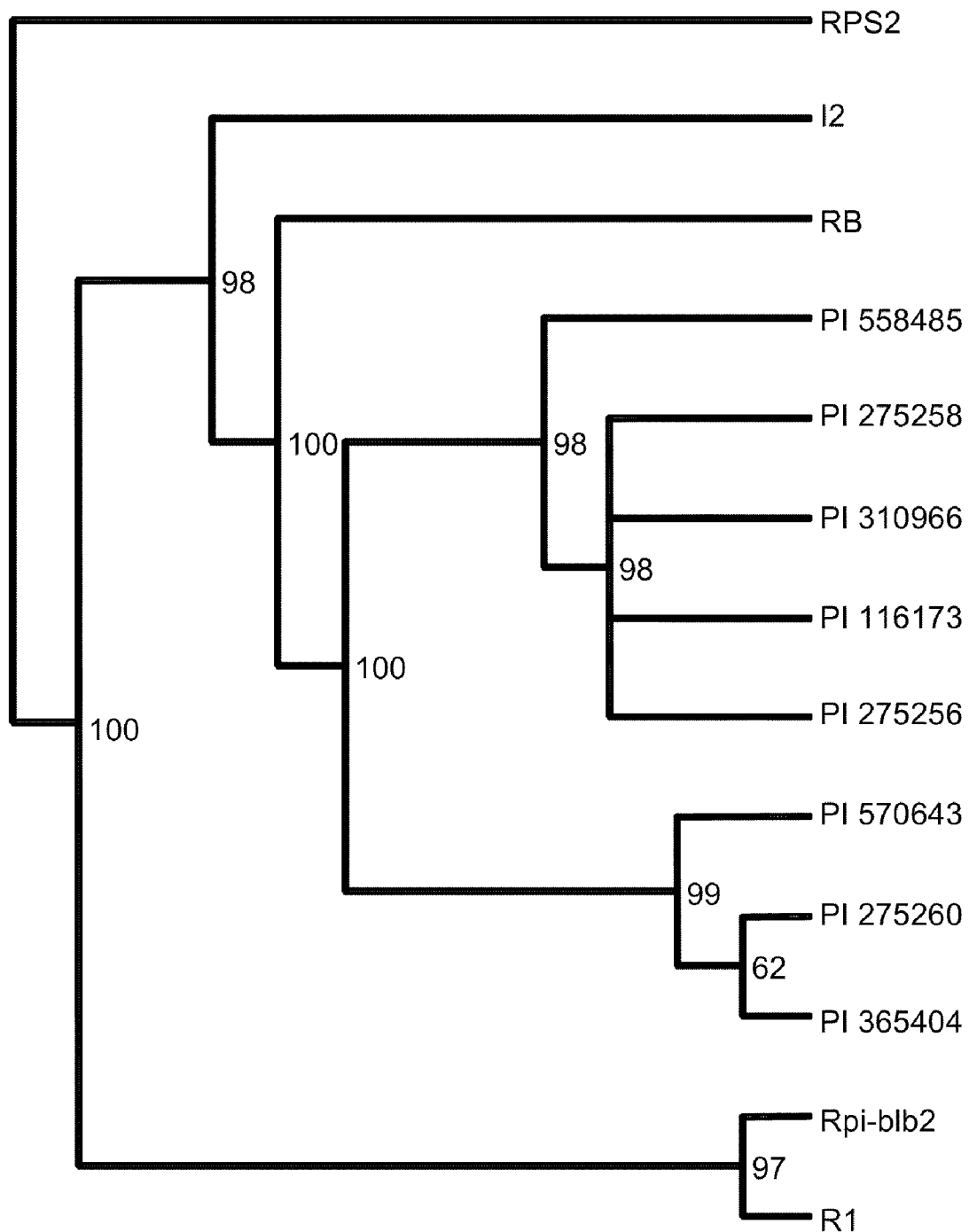
FIG. 4 is a dendrogram illustrating clustering analysis of open reading frames of $RB^{blb}$ and eight $RB^{ver}$ orthologs (PI 558485, PI 275258, PI 310966, PI 116173, PI 275256, PI 570643, PI 275260, and PI 365404).

To investigate the protein sequence relationships among the eight $RB^{ver}$ orthologs, $RB^{blb}$, Rpi-blb2, potato late blight resistance protein R1 from *S. demissum*, and tomato I2 resistance protein, cluster analysis using the neighbor-joining method was performed. The results of this analysis are shown in FIG. 4, which is a dendrogram illustrating clustering analysis of open reading frames of the eight $RB^{ver}$ orthologs and $RB^{blb}$. The phylogenetic tree was constructed using the neighbor joining distance matrix method, based on the conserved overlapping portions of the $RB^{blb}$ and $RB^{ver}$ orthologs. Bootstrap values from 1,000 replications >90 are shown at the nodes. The length of the branches reflects weighted amino acid substitutions. RPS2 from *Arabidopsis thaliana* was included as an outgroup.

Since some predicted $RB^{ver}$ orthologous proteins contain frame shifts due to deletions, these deletions were replaced with gaps in those protein sequences for further analysis. A total of 1,000 bootstrap replications were conducted to determine the statistical significance of the obtained branches. Two main branches were observed. RB$^{blb}$ and tomato 12 clustered with all eight *S. verrucosum* orthologs. The R1 protein was most closely related to Rpi-blb2. Interestingly, RB$^{ver}$ orthologs from resistant accessions did not necessarily cluster more closely to RB than proteins from susceptible accessions.

The isolated RB$^{ver}$ gene encodes a RB$^{ver}$ protein that contains 21 LRRs, one more leucine-rich repeat than the RB$^{blb}$ protein. Not wanting to be bound by the following theory, the variation of LRRs may play a role in determining recognition specificity of the RB protein. It has been demonstrated that expansion and contraction of LRRs are responsible for loss of function or recognition specificities of plant disease resistance genes. In flax, inactivation of the rust resistance gene M was associated with the loss of a single repeated unit within the LRR coding region (Anderson et al., 1997, *Plant Cell* 9: 641-651). Sequence analysis of mutant RPP5 alleles identified four duplicated LRRs in comparison to the wild-type RPP5 gene (Parker et al., 1997, *Plant Cell* 9: 879-894). Domain swapping and gene shuffling of tomato Cf-4 and Cf-9 protein also demonstrated that variation in LRR copy number plays a major role in determining recognition specificity in these proteins (Wulff et al., 2001, *Plant Cell* 13: 255-272). It is possible that a similar mechanism exists with the recognition specificity relative to *Phytophthora* infections.

Not wanting to be bound by the following theory, based on the protein sequence (SEQ ID NO:2), the RB$^{ver}$ protein may belong to the NBS-LRR class of RB proteins. Its putative NBS domain consists of three motifs: kinase 1a or P-loop, kinase 2, and kinase 3a (FIG. 1). Downstream of the kinase motifs is a domain conserved among resistance genes, which contains QLPL, CFAY, and MHD motifs. The RB protein contains one putative five-heptad leucine zipper motif near the N terminus. Another region containing four heptad repeats can be observed within the LRR domain. As indicated above, the LRR domain consists of 21 leucine-rich repeats.

The RB$^{Ver}$ Proteins are Under Diversifying Selection

The gene RB has a similar evolutionary pattern to Type II resistance genes (Song et al., 2003, *Proc. Natl. Acad. Sci. USA* 10016: 9128-9133). Type II resistance genes are predicted to evolve slowly and show striking allelic/orthologous relationships in different genotypes or closely related species. Therefore, little diversifying selection would be expected when comparing the RB$^{blb}$ and RB$^{ver}$ sequences. To test this hypothesis, the average ratios of the numbers of nonsynonymous nucleotide substitutions per nonsynonymous site ($d_N$) and synonymous nucleotide substitutions per synonymous site ($d_S$) among the eight RB$^{ver}$ orthologous sequences and RB$^{blb}$ were calculated, using the approximate method of Nei and Gojobori in PAML (Nei and Gojobori, 1986, *Mol. Biol. Evol.* 35: 418-426).

Using this method, no diversifying selection was detected. In most proteins, a high proportion of amino acid sites is expected to be highly conserved as a result of functional constraints, and neutral and purifying selection are thought to be major forces in molecular evolution. Under these circumstances, the approximate method should not be sensitive enough to detect diversifying selection because it averages the ω ratios over all sites of the protein. Subsequently, a more sensitive Maximum Likelihood (ML) method was applied (Nielsen and Yang, 1998, *Genetics* 1483: 929-936; Fu et al., 2000, *Yi Chuan Xue Bao* 279: 787-791; Yang and Bielawski, 2000, *Trends Ecol. Evol.* 15: 496-503). One pair of ML models of codon substitution, M3/M0, was used. The discrete model M3 suggested that 22% of the amino acid sites are under diversifying selection ($\omega_1=1.2$) and 3% of the amino acid sites are under strong diversifying selection ($\omega_2=8.5$). A likelihood ratio test (LRT) indicated that the discrete model M3 fit the data significantly better than the neutral model M0, which did not allow for the presence of diversifying selection sites with ω>1 (P<0.001). Twelve amino acid sites (those with posterior probability values over 0.9) were implicated as being under significant diversifying selection under the discrete model M3 using the empirical Bayes theorem (FIG. 5) (Nielsen and Yang, 1998, *Genetics* 1483: 929-936; Fu et al., 2000, *Yi Chuan Xue Bao* 279: 787-791; Yang and Bielawski, 2000, *Trends Ecol. Evol.* 15: 496-503).

Figure 5:
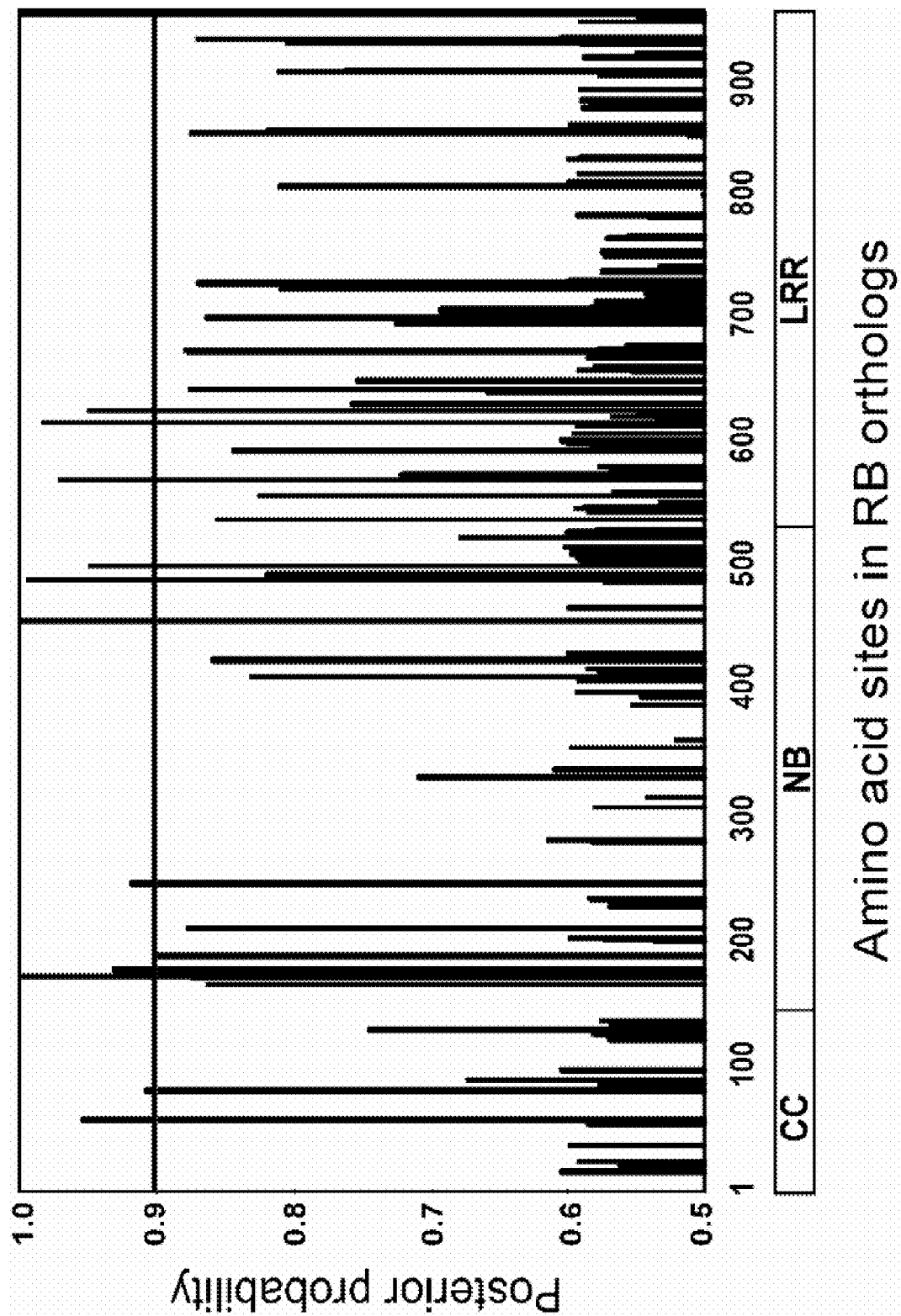
FIG. 5 is a graph that illustrates posterior probabilities for site classes ($\omega>1$) estimated under the discrete model M3 in the PAML software package along the $RB^{ver}$ orthologous protein sequence.

FIG. 5 illustrates posterior probabilities for site classes (ω>1) estimated under the discrete model M3 in PAML along the RB$^{ver}$ orthologous protein sequence. The X-axis denotes the position in the amino acid alignment. An amino acid site with a posterior probability >0.9 (indicated with a horizontal line) is considered to be under significant diversifying selection. As shown in FIG. 5, twelve such amino acid sites were identified. As is also shown in FIG. 1, these residues are: lys58, glu82, arg176, lue181, gln251, asp465, val498, phe509, his580, cys626, gln636, thr949. Eight of the twelve amino acid sites are located outside the LRRs while four lie within the LRR repeats. Not wanting to be bound by the following theory, the sites under diversifying selection identify amino acids that may have a role in pathogen recognition. Thus, using the sequence data in FIG. 1 and the information on amino acid sites that are under significant diversifying selection, shown in FIG. 5, it may be possible to identify and/or generate additional orthologs or variants useful for practicing the present invention.

Complementation Analysis of an RB Ortholog from *S. verrucosum* PI 275260

In order to test whether the RB$^{ver}$ ortholog from resistant accession PI 275260 could complement the *P. infestans* susceptible phenotype in cultivated potato, *S. tuberosum* cv. Katahdin was transformed with a full-length open reading frame of this gene under control of the 35S cauliflower mosaic virus promoter and the nopaline synthase terminator (nos). Forty-nine transgenic RB$^{ver}$ Katahdin plants were screened for resistance to *P. infestans* isolate US 940480. PCR using transgene-specific primers confirmed the presence of the gene in 36 out of these 49 transgenic Katahdin plants. Surprisingly, only four out of the 36 plants, each from independently isolated explants, consistently displayed increased resistance to *P. infestans* (Table 3). Six-week-old seedlings were placed in a misting chamber (100% humidity, 18° C.) and spray inoculated with sporangia from the US 940480 strain of *P. infestans*. Plants were scored 10 days after inoculation. The late blight resistance score shown in Table 3 was calculated based on observation of diseased leaf tissue: 0=100% diseased tissue, 8=<10% diseased tissue. For complementation analysis of a putative RB$^{ver}$ orthologous gene for late blight resistance, disease symptoms were recorded 10 days after inoculation. Susceptible *S. tuberosum* cv. Katahdin and resistant RB$^{blb}$-transgenic plants SP951 were provided by Sandra Austin-Phillips, University of Wisconsin-Madison Biotechnology Center, and were used as controls (Halterman et al., 2008, *Plant Dis.* 92: 339-343).

The relatively low number of functional transformants suggests that proper expression of RB might be critical for plant viability or expression of the resistance phenotype. Among the four plants exhibiting the resistance phenotype, only some chlorosis was observed on the lower leaves, confirming the functionality of the RB ortholog from *S. verrucosum* PI 275260 in potato. Similar to the RB$^{blb}$ transgenics, these RB$^{ver}$ transgenic lines exhibit rate-limiting resistance to *P.*

*infestans* suggesting the presence of other major genes required for complete resistance.

TABLE 3

Testing of RB$^{ver}$ transgenics for resistance to late blight

| Plants | Late blight score |
|---|---|
| Katahdin | 4 ± 1.0 |
| SP951 | 8 ± 0.0 |
| SP2808 | 6 ± 2.7 |
| SP2824 | 6.5 ± 0.5 |
| SP2829 | 4.7 ± 2.1 |
| SP2906 | 7 ± 1.0 |

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters normally encountered in plant physiology, plant molecular biology, and plant pathology, and obvious to those skilled in the art, are within the scope of this invention. All publications, patents, and patent applications cited herein are incorporated by reference in their entirety for all purposes.

What is claimed is:

1. An isolated polynucleotide encoding a polypeptide comprising an amino acid sequence that is at least 95% identical to SEQ ID NO:2, wherein the polypeptide confers disease resistance in a solanaceous plant.

2. The isolated polynucleotide of claim 1, which is at least 95% identical to SEQ ID NO:1.

3. The isolated polynucleotide of claim 1, which encodes the amino acid sequence of SEQ ID NO:2.

4. The isolated polynucleotide of claim 1, which is isolated from *Solanum verrucosum*.

5. The isolated polynucleotide of claim 1, which encodes a polypeptide that confers disease resistance to an oomycete pathogen.

6. The isolated polynucleotide of claim 5 wherein the oomycete pathogen is *Phytophthora infestans*.

7. The isolated polynucleotide of claim 1 wherein the solanaceous plant is selected from the group consisting of potato, tomato, and eggplant.

8. A vector comprising the polynucleotide of claim 1.

9. The vector of claim 8 further comprising a recombinant expression cassette, which comprises a promoter sequence operably linked to the polynucleotide.

10. A host cell transformed with a vector comprising the polynucleotide of claim 1.

11. A transgenic plant comprising an isolated polynucleotide encoding a polypeptide comprising an amino acid sequence that is at least 95% identical to SEQ ID NO:2, wherein the polypeptide confers disease resistance in the transgenic plant.

12. The transgenic plant according to claim 11 wherein the plant is potato, tomato, or tobacco.

13. The transgenic plant according to claim 11 wherein the plant is resistant to *Phytophthora infestans*.

14. A transgenic plant comprising a recombinant expression cassette that comprises a promoter sequence operably linked to a polynucleotide encoding a polypeptide, wherein the polypeptide comprises an amino acid sequence that is at least 95% identical to SEQ ID NO:2.

15. The transgenic plant according to claim 14 wherein the plant is potato, tomato, or tobacco.

16. The transgenic plant according to claim 14 wherein the plant is resistant to *Phytophthora infestans*.

17. A method of enhancing disease resistance in a solanaceous plant, the method comprising introducing into the solanaceous plant a recombinant expression cassette comprising a promoter operably linked to a polynucleotide encoding a polypeptide, wherein the polypeptide comprises an amino acid sequence that is at least 95% identical to SEQ ID NO:2.

18. The method according to claim 17 wherein the solanaceous plant is potato, tomato, or tobacco.

19. The method according to claim 17 wherein the method enhances disease resistance to an oomycete pathogen.

20. The method according to claim 19 wherein the oomycete pathogen is *Phytophthora infestans*.

21. An isolated polypeptide comprising an amino acid sequence that is at least 95% identical to SEQ ID NO:2 wherein the polypeptide confers disease resistance in a solanaceous plant.

22. The isolated polypeptide of claim 21, which comprises the amino acid sequence of SEQ ID NO:2.

23. The isolated polypeptide of claim 21, which encodes a polypeptide that confers disease resistance to an oomycete pathogen.

24. The isolated polypeptide of claim 23, wherein the oomycete pathogen is Phytophthora infestans.

* * * * *

SEQUENCE LISTING

```
<160> NUMBER OF SEQ ID NOS: 45

<210> SEQ ID NO 1
<211> LENGTH: 3903
<212> TYPE: DNA
<213> ORGANISM: Solanum verrucosum

<400> SEQUENCE: 1
cttcccattt cattccaact agcccatctt ggcttcaaaa ttacacattc attcatagtc      60
acagatctaa tattcttaat agtgatttcc acatatggct gaagctttca ttcaagttct     120
gctagacaat ctcacttctg tcctcaaagg agaacttgta ttgcttttcg gttttcaaga     180
tgagttccaa aggctttcaa gcatcttctc tacaatccaa gctgtccttg aagatgctca     240
ggagaagcaa ctcaacgaca agccactaga aaattggttg caaaaactca atgctgctac     300
atatgaagtc gatgacatct tggatgaata taaaactgag gccacaagat tcttgcagtc     360
tgaatatggc cgttatcatc caaaggcaat ccctttccgt cacaaggttg ggaaaaggat     420
ggaccaagtg atgaaaaaac tgaatgcaat tgctgaggaa agaaagaatt tccatttgca     480
agaaaagatt atagagagac aagctgctac acgggaaaca ggtactcatc ttaaattagt     540
agtattacaa cttagtttat attcattcat ttgttttggg caatgatcaa attatgtaaa     600
ggtcaaatat actcatgtac tattggaaat agtttaaata tacctctagt tatactttca     660
gtgcaaacat actcctccca tatagaagac tacatccgtt ttgcttttct taacgaagca     720
gctcagagaa aagaggtttt cttctgttct gtttctctat gggctgcatt ggggtcttaa     780
tccaataaga aacaataaac ataacaggca tatttaacaa attaatatta cgttctcgat     840
gacggtggtc tttctagaca tgaactgagt gtaaattttg gtaaattttg tctcaaggaa     900 gaaaagaaa tgattaggct ggatttcttt cagagtggaa tataggggga taaagttgga     960
gcatagagtt ccatcgttta tttcttacat aaaagtaaca agttcaacaa aatgatatca    1020
aggtacttta atggaaaatt atcagacacg tctaaactac aaaaatggaa tagaaactta    1080
aatcatcctc taacaaagct accaaattta aatcatgata cagagaagca accaaaaaca    1140
ttatgggtga attgtttgat ttgatgcttg tcacatgtct tcccgtcaag attaaaggaa    1200
aaattgcgcc gaagtataaa tggtgcagta tatttggact aatagtataa cgacaagtat    1260
atttgatcat tttatgtatc aaattcatgt ggttttgggg gagaagggaa gtttcaaagt    1320
tttcaacctg ctcctcatct catccatatc tcttattgt gcaaaaccct tttctattta    1380
actattttct gccgactcct aatgagcttg aatgtaacaa tattctcatc tggacattgc    1440
ttgcaccagg ttctgtgtta actgaaccac aagtttatgg aagggacaaa gaaaatgatg    1500
```

```
agatagtgaa atcctaata aacaatgcta gtgatgccca aaaactcaga gtcctcccaa    1560
tacttggtat gggggggacta ggaaagacaa ctctttccca aatggtcttc aatgatcaga    1620
gagtaactga acatttctat cccaaactgt ggatttgtgt ctccaatgat tttgatgaga    1680
agaggttgat aaaggcaata gtagaatcta ttgaagggaa gtcactcagt gacatggact    1740
tggctccact tcaaaagaag cttcaagagt tgcagaatgg aaaaagatac ttgcttgtct    1800
tagatgatgt ttggaatgaa gatcaacaga agtgggctaa tttaagagca gtgttgaagg    1860
ttggagcaag tggttcattt gttctaacta ctactcgtct tgaaaaggtt ggatcaatta    1920
tgggaacatt gcaaccatat gaattgtcaa atctgtctcc agaggattgt tggttttgt    1980 tcatacagcg tgcatttgga caccaagaag aaataaatcc aaaccttgtg gatatcggaa    2040
aggagattat gaaaaaaagt ggtggtgtgc ctctagcagc caagactctt ggaggtattt    2100
tgcgcttcaa gagagaagaa agagaatggg aacatgtgag agacagtccg atttggaatt    2160
tgcctcaaga tgaaagttct attctgcctg ccctgaggct tagttaccat caccttccac    2220
ttgatttgag acaatgcttt gtgtattgtg cggtattccc gaaggacacc aaaatggcaa    2280
aggaaaatct aatcgctttc tggatggcac acggttttct tttatcgaaa ggaaatttgg    2340
agctagagga tgtaggtaat gaagtatgga tgaattata cttgaggtct ttcttccaag    2400
agattgaagt taaagatggt aaaacttatt caagatgca tgatctcatc catgatttgg    2460
ctacatctct gttttcagca aacacatcaa gcagcaacat tcgtgaaata tatgttaatt    2520
atgatggata tatgatgtcg attggttcg ctgaagtggg gtcttcttac tctccttcac    2580
tcttgcaaaa gtttgtctca ttaagagtgc ttaatctaag aaactcggac ctaaatcaat    2640
taccatcctc cattggagat ctagtacatt taagatacct ggacttgtct gacaatatta    2700
gaattcgtag tcttccaaag agattatgca agcttcaaaa tctgcagact cttgatctac    2760
ataattgcta ctctctttct tgtttgccaa aacaaacaag taaacttggt agtctccgaa    2820
atcttttact tgatggctgt tcattgacgt caacgccacc aaggatagga ttgttgacat    2880
gccttaagtc tctaagttgc tttgttattg gcaagagaaa aggttatcaa cttggtgaac    2940
taaaaaacct aaatctctat ggctcaattt caatcacaaa acttgagaga gtgaagaaag    3000
gaagggatgc aaaagaagct aatatatctg ttaaagcaaa tctgcactct ttaagcctga    3060
gttgggattt tgatggaaca catagatatg aatcagaagt tcttgaagcc ctcaaaccac    3120
actccaatct gaaatattta gaaatcattg gcttcagagg aatccgtctc ccagactgga    3180
tgaatcaatc agttttgaaa aatgttgtct ctattacaat tagaggttgt gaaaactgct    3240
cgtgcttacc acccttggt gagctgccta gtctagaaag tctagagtta cacacgggt    3300 ctgcggaggt ggagtatgtt gaagagaatg ctcatcctgg aaggtttcca tccttgagga    3360
aacttgttat ttgcgacttt ggtaatctga aaggattgct gaaaaaggaa ggagaagagc    3420
aatttcctgt gcttgaagag atgacaattc acgggtgccc tatgtttgtt attccgaccc    3480
tttcttctgt caagacattg aaagttgatg tgacagatgc aacagttttg aggtccatat    3540
ctaatcttag ggctcttact tcgctcgaca ttagcagtaa ctatgaagct acttcactcc    3600
cagaagagat gttcaaaaac cttgcagatc tcaaagactt gactatctct gacttcaaga    3660
atctcaaaga gctgcctacc tgcctggcta gtctcaatgc tttgaatagt ctacaaattg    3720
aatattgtga cgcactagag agtctcccag aggaagggt aaaagtttta acttcactca    3780
ccgagttgtc tgtcagtaat tgtatgacgc taaaatgttt accggaggga ttgcagcacc    3840
taacagccct aacaacttta ataattactc aatgtccaat agtgatcaag cggtgtgaga    3900
```

```
agg                                                                 3903

<210> SEQ ID NO 2
<211> LENGTH: 960
<212> TYPE: PRT
<213> ORGANISM: Solanum verrucosum

<400> SEQUENCE: 2

Met Ala Glu Ala Phe Ile Gln Val Leu Leu Asp Asn Leu Thr Ser Val
1               5                   10                  15

Leu Lys Gly Glu Leu Val Leu Leu Phe Gly Phe Gln Asp Glu Phe Gln
            20                  25                  30

Arg Leu Ser Ser Ile Phe Ser Thr Ile Gln Ala Val Leu Glu Asp Ala
        35                  40                  45

Gln Glu Lys Gln Leu Asn Asp Lys Pro Leu Glu Asn Trp Leu Gln Lys
    50                  55                  60

Leu Asn Ala Ala Thr Tyr Glu Val Asp Asp Ile Leu Asp Glu Tyr Lys
65                  70                  75                  80

Thr Glu Ala Thr Arg Phe Leu Gln Ser Glu Tyr Gly Arg Tyr His Pro
                85                  90                  95

Lys Ala Ile Pro Phe Arg His Lys Val Gly Lys Arg Met Asp Gln Val
            100                 105                 110

Met Lys Lys Leu Asn Ala Ile Ala Glu Glu Arg Lys Asn Phe His Leu
        115                 120                 125

Gln Glu Lys Ile Ile Glu Arg Gln Ala Ala Thr Arg Glu Thr Gly Ser
    130                 135                 140

Val Leu Thr Glu Pro Gln Val Tyr Gly Arg Asp Lys Glu Asn Asp Glu
145                 150                 155                 160

Ile Val Lys Ile Leu Ile Asn Asn Ala Ser Asp Ala Gln Lys Leu Arg
                165                 170                 175

Val Leu Pro Ile Leu Gly Met Gly Gly Leu Gly Lys Thr Thr Leu Ser
            180                 185                 190

Gln Met Val Phe Asn Asp Gln Arg Val Thr Glu His Phe Tyr Pro Lys
        195                 200                 205

Leu Trp Ile Cys Val Ser Asn Asp Phe Asp Glu Lys Arg Leu Ile Lys
    210                 215                 220

Ala Ile Val Glu Ser Ile Glu Gly Lys Ser Leu Ser Asp Met Asp Leu
225                 230                 235                 240

Ala Pro Leu Gln Lys Lys Leu Gln Glu Leu Gln Asn Gly Lys Arg Tyr
                245                 250                 255

Leu Leu Val Leu Asp Asp Val Trp Asn Glu Asp Gln Gln Lys Trp Ala
            260                 265                 270

Asn Leu Arg Ala Val Leu Lys Val Gly Ala Ser Gly Ser Phe Val Leu
        275                 280                 285

Thr Thr Thr Arg Leu Glu Lys Val Gly Ser Ile Met Gly Thr Leu Gln
    290                 295                 300

Pro Tyr Glu Leu Ser Asn Leu Ser Pro Glu Asp Cys Trp Phe Leu Phe
305                 310                 315                 320

Ile Gln Arg Ala Phe Gly His Gln Glu Glu Ile Asn Pro Asn Leu Val
                325                 330                 335

Asp Ile Gly Lys Glu Ile Met Lys Lys Ser Gly Gly Val Pro Leu Ala
            340                 345                 350

Ala Lys Thr Leu Gly Gly Ile Leu Arg Phe Lys Arg Glu Glu Arg Glu
        355                 360                 365
```

-continued

```
Trp Glu His Val Arg Asp Ser Pro Ile Trp Asn Leu Pro Gln Asp Glu
            370                 375                 380

Ser Ser Ile Leu Pro Ala Leu Arg Leu Ser Tyr His His Leu Pro Leu
385                 390                 395                 400

Asp Leu Arg Gln Cys Phe Val Tyr Cys Ala Val Phe Pro Lys Asp Thr
                405                 410                 415

Lys Met Ala Lys Glu Asn Leu Ile Ala Phe Trp Met Ala His Gly Phe
            420                 425                 430

Leu Leu Ser Lys Gly Asn Leu Glu Leu Glu Asp Val Gly Asn Glu Val
            435                 440                 445

Trp Asn Glu Leu Tyr Leu Arg Ser Phe Phe Gln Glu Ile Glu Val Lys
            450                 455                 460

Asp Gly Lys Thr Tyr Phe Lys Met His Asp Leu Ile His Asp Leu Ala
465                 470                 475                 480

Thr Ser Leu Phe Ser Ala Asn Thr Ser Ser Asn Ile Arg Glu Ile
                485                 490                 495

Tyr Val Asn Tyr Asp Gly Tyr Met Met Ser Ile Gly Phe Ala Glu Val
                500                 505                 510

Val Ser Ser Tyr Ser Pro Ser Leu Leu Gln Lys Phe Val Ser Leu Arg
            515                 520                 525

Val Leu Asn Leu Arg Asn Ser Asp Leu Asn Gln Leu Pro Ser Ser Ile
530                 535                 540

Gly Asp Leu Val His Leu Arg Tyr Leu Asp Leu Ser Asp Asn Ile Arg
545                 550                 555                 560

Ile Arg Ser Leu Pro Lys Arg Leu Cys Lys Leu Gln Asn Leu Gln Thr
                565                 570                 575

Leu Asp Leu His Asn Cys Tyr Ser Leu Ser Cys Leu Pro Lys Gln Thr
            580                 585                 590

Ser Lys Leu Gly Ser Leu Arg Asn Leu Leu Asp Gly Cys Ser Leu
            595                 600                 605

Thr Ser Thr Pro Pro Arg Ile Gly Leu Leu Thr Cys Leu Lys Ser Leu
            610                 615                 620

Ser Cys Phe Val Ile Gly Lys Arg Lys Gly Tyr Gln Leu Gly Glu Leu
625                 630                 635                 640

Lys Asn Leu Asn Leu Tyr Gly Ser Ile Ser Ile Thr Lys Leu Glu Arg
                645                 650                 655

Val Lys Lys Gly Arg Asp Ala Lys Glu Ala Asn Ile Ser Val Lys Ala
                660                 665                 670

Asn Leu His Ser Leu Ser Leu Ser Trp Asp Phe Asp Gly Thr His Arg
            675                 680                 685

Tyr Glu Ser Glu Val Leu Glu Ala Leu Lys Pro His Ser Asn Leu Lys
            690                 695                 700

Tyr Leu Glu Ile Ile Gly Phe Arg Gly Ile Arg Leu Pro Asp Trp Met
705                 710                 715                 720

Asn Gln Ser Val Leu Lys Asn Val Val Ser Ile Thr Ile Arg Gly Cys
                725                 730                 735

Glu Asn Cys Ser Cys Leu Pro Pro Phe Gly Glu Leu Pro Ser Leu Glu
            740                 745                 750

Ser Leu Glu Leu His Thr Gly Ser Ala Glu Val Glu Tyr Val Glu Glu
            755                 760                 765

Asn Ala His Pro Gly Arg Phe Pro Ser Leu Arg Lys Leu Val Ile Cys
            770                 775                 780

Asp Phe Gly Asn Leu Lys Gly Leu Leu Lys Lys Glu Gly Glu Glu Gln
785                 790                 795                 800
```

-continued

```
Phe Pro Val Leu Glu Glu Met Thr Ile His Gly Cys Pro Met Phe Val
                805                 810                 815
Ile Pro Thr Leu Ser Ser Val Lys Thr Leu Lys Val Asp Val Thr Asp
            820                 825                 830
Ala Thr Val Leu Arg Ser Ile Ser Asn Leu Arg Ala Leu Thr Ser Leu
        835                 840                 845
Asp Ile Ser Ser Asn Tyr Glu Ala Thr Ser Leu Pro Glu Glu Met Phe
    850                 855                 860
Lys Asn Leu Ala Asp Leu Lys Asp Leu Thr Ile Ser Asp Phe Lys Asn
865                 870                 875                 880
Leu Lys Glu Leu Pro Thr Cys Leu Ala Ser Leu Asn Ala Leu Asn Ser
                885                 890                 895
Leu Gln Ile Glu Tyr Cys Asp Ala Leu Glu Ser Leu Pro Glu Glu Gly
            900                 905                 910
Val Lys Ser Leu Thr Ser Leu Thr Glu Leu Ser Val Ser Asn Cys Met
        915                 920                 925
Thr Leu Lys Cys Leu Pro Glu Gly Leu Gln His Leu Thr Ala Leu Thr
    930                 935                 940
Thr Leu Ile Ile Thr Gln Cys Pro Ile Val Ile Lys Arg Cys Glu Lys
945                 950                 955                 960
```

<210> SEQ ID NO 3
<211> LENGTH: 2880
<212> TYPE: DNA
<213> ORGANISM: Solanum verrucosum

<400> SEQUENCE: 3

```
atggctgaag ctttcattca agttctgcta gacaatctca cttctgtcct caaaggagaa      60
cttgtattgc ttttcggttt tcaagatgag ttccaaaggc tttcaagcat cttctctaca     120
atccaagctg tccttgaaga tgctcaggag aagcaactca acgacaagcc actagaaaat     180
tggttgcaaa aactcaatgc tgctacatat gaagtcgatg acatcttgga tgaatataaa     240
actgaggcca caagattctt gcagtctgaa tatggccgtt atcatccaaa ggcaatccct     300
ttccgtcaca aggttgggaa aaggatggac caagtgatga aaaaactgaa tgcaattgct     360
gaggaaagaa agaatttcca tttgcaagaa aagattatag agagacaagc tgctacacgg     420
gaaacaggtt ctgtgttaac tgaaccacaa gtttatggaa gggacaaaga aaatgatgag     480
atagtgaaaa tcctaataaa caatgctagt gatgcccaaa aactcagagt cctcccaata     540
cttggtatgg ggggactagg aaagacaact ctttcccaaa tggtcttcaa tgatcagaga     600
gtaactgaac atttctatcc caaactgtgg atttgtgtct ccaatgattt tgatgagaag     660
aggttgataa aggcaatagt agaatctatt gaagggaagt cactcagtga catggacttg     720
gctccacttc aaaagaagct tcaagagttg cagaatggaa aaagatactt gcttgtctta     780
gatgatgttt ggaatgaaga tcaacagaag tgggctaatt taagagcagt gttgaaggtt     840
ggagcaagtg gttcatttgt tctaactact actcgtcttg aaaaggttgg atcaattatg     900
ggaacattgc aaccatatga attgtcaaat ctgtctccag aggattgttg gtttttgttc     960
atacagcgtg catttggaca ccaagaagaa ataaatccaa accttgtgga tatcggaaag    1020
gagattatga aaaaaagtgg tggtgtgcct ctagcagcca agactcttgg aggtattttg    1080
cgcttcaaga gagaagaaag agaatgggaa catgtgagag acagtccgat ttggaatttg    1140
cctcaagatg aaagttctat tctgcctgcc ctgaggctta gttaccatca ccttccactt    1200
gatttgagac aatgctttgt gtattgtgcg gtattcccga aggacaccaa aatggcaaag    1260
```

-continued

```
gaaaatctaa tcgctttctg gatggcacac ggttttcttt tatcgaaagg aaatttggag    1320
ctagaggatg taggtaatga agtatggaat gaattatact tgaggtcttt cttccaagag    1380
attgaagtta aagatggtaa aacttatttc aagatgcatg atctcatcca tgatttggct    1440
acatctctgt tttcagcaaa cacatcaagc agcaacattc gtgaaatata tgttaattat    1500
gatggatata tgatgtcgat tggtttcgct gaagtggtgt cttcttactc tccttcactc    1560
ttgcaaaagt ttgtctcatt aagagtgctt aatctaagaa actcggacct aaatcaatta    1620
ccatcctcca ttggagatct agtacattta agatacctgg acttgtctga caatattaga    1680
attcgtagtc ttccaaagag attatgcaag cttcaaaatc tgcagactct tgatctacat    1740
aattgctact ctctttcttg tttgccaaaa caaacaagta aacttggtag tctccgaaat    1800
cttttacttg atggctgttc attgacgtca acgccaccaa ggataggatt gttgacatgc    1860
cttaagtctc taagttgctt tgttattggc aagagaaaag gttatcaact tggtgaacta    1920
aaaaacctaa atctctatgg ctcaatttca atcacaaaac ttgagagagt gaagaaagga    1980
agggatgcaa aagaagctaa tatatctgtt aaagcaaatc tgcactcttt aagcctgagt    2040
tgggattttg atggaacaca tagatatgaa tcagaagttc ttgaagccct caaaccacac    2100
tccaatctga atatttaga aatcattggc ttcagaggaa tccgtctccc agactggatg    2160
aatcaatcag ttttgaaaaa tgttgtctct attacaatta gaggttgtga aaactgctcg    2220
tgcttaccac cctttggtga gctgcctagt ctagaaagtc tagagttaca cacggggtct    2280
gcggaggtgg agtatgttga agagaatgct catcctggaa ggtttccatc cttgaggaaa    2340
cttgttattt gcgactttgg taatctgaaa ggattgctga aaaggaagg agaagagcaa     2400 tttcctgtgc ttgaagagat gacaattcac gggtgcccta tgtttgttat tccgaccctt    2460
tcttctgtca agacattgaa agttgatgtg acagatgcaa cagttttgag gtccatatct    2520
aatcttaggg ctcttacttc gctcgacatt agcagtaact atgaagctac ttcactccca    2580
gaagagatgt tcaaaaacct tgcagatctc aaagacttga ctatctctga cttcaagaat    2640
ctcaaagagc tgcctacctg cctggctagt ctcaatgctt tgaatagtct acaaattgaa    2700
tattgtgacg cactagagag tctcccagag gaaggggtta aaagtttaac ttcactcacc    2760
gagttgtctg tcagtaattg tatgacgcta aaatgtttac cggagggatt gcagcaccta    2820
acagccctaa caactttaat aattactcaa tgtccaatag tgatcaagcg gtgtgagaag    2880
```

<210> SEQ ID NO 4
<211> LENGTH: 24
<212> TYPE: DNA
<213> ORGANISM: Artificial
<220> FEATURE:
<223> OTHER INFORMATION: F1 primer

<400> SEQUENCE: 4
cttcccattt cattccaact agcc                                            24

<210> SEQ ID NO 5
<211> LENGTH: 22
<212> TYPE: DNA
<213> ORGANISM: Artificial
<220> FEATURE:
<223> OTHER INFORMATION: R14 primer

<400> SEQUENCE: 5
ccttctcaca ccgcttgatc ag                                              22

```
<210> SEQ ID NO 6
<211> LENGTH: 25
<212> TYPE: DNA
<213> ORGANISM: Artificial
<220> FEATURE:
<223> OTHER INFORMATION: F3 primer

<400> SEQUENCE: 6
tcaagccgtc cttgaagatg ctcag                                         25

<210> SEQ ID NO 7
<211> LENGTH: 24
<212> TYPE: DNA
<213> ORGANISM: Artificial
<220> FEATURE:
<223> OTHER INFORMATION: R3 primer

<400> SEQUENCE: 7
ggcgaaacca atggacatca tatg                                          24

<210> SEQ ID NO 8
<211> LENGTH: 20
<212> TYPE: DNA
<213> ORGANISM: Artificial
<220> FEATURE:
<223> OTHER INFORMATION: 35Sfor primer

<400> SEQUENCE: 8
gtaagggatg acgcacaatc                                               20

<210> SEQ ID NO 9
<211> LENGTH: 39
<212> TYPE: DNA
<213> ORGANISM: Artificial
<220> FEATURE:
<223> OTHER INFORMATION: RBver-SOErev primer

<400> SEQUENCE: 9
gccagtcttc tcctattccc ttctcacacc gcttgatca                          39

<210> SEQ ID NO 10
<211> LENGTH: 42
<212> TYPE: DNA
<213> ORGANISM: Artificial
<220> FEATURE:
<223> OTHER INFORMATION: RB-SOEfor primer

<400> SEQUENCE: 10
taattactca atgtccaata gtgatcaagc ggtgtgagaa gg                      42

<210> SEQ ID NO 11
<211> LENGTH: 20
<212> TYPE: DNA
<213> ORGANISM: Artificial
<220> FEATURE:
<223> OTHER INFORMATION: nosrev primer

<400> SEQUENCE: 11
cgtcatgcat tacatgttaa                                               20

<210> SEQ ID NO 12
<211> LENGTH: 22
<212> TYPE: DNA
<213> ORGANISM: Artificial
<220> FEATURE:
<223> OTHER INFORMATION: KanFor1 primer

<400> SEQUENCE: 12
```
cgcttgggtg gagaggctat tc 22

<210> SEQ ID NO 13
<211> LENGTH: 20
<212> TYPE: DNA
<213> ORGANISM: Artificial
<220> FEATURE:
<223> OTHER INFORMATION: KanRev1 primer

<400> SEQUENCE: 13
aggaagcggt cagcccattc 20

<210> SEQ ID NO 14
<211> LENGTH: 24
<212> TYPE: PRT
<213> ORGANISM: Artificial Sequence
<220> FEATURE:
<223> OTHER INFORMATION: Consensus sequence for alignment of LRR regions
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (17)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid

<400> SEQUENCE: 14

Leu Xaa Xaa Leu Xaa Xaa Leu Xaa Xaa Leu Xaa Leu Xaa Xaa Asn Cys
1 5 10 15

Xaa Xaa Leu Xaa Xaa Leu Xaa Xaa
20

<210> SEQ ID NO 15
<211> LENGTH: 520
<212> TYPE: PRT
<213> ORGANISM: Solanum verrucosum

<400> SEQUENCE: 15

Met Ala Glu Ala Phe Ile Gln Val Leu Leu Asp Asn Leu Thr Ser Val
1 5 10 15

Leu Lys Gly Glu Leu Val Leu Leu Phe Gly Phe Gln Asp Glu Phe Gln
20 25 30

Arg Leu Ser Ser Ile Phe Ser Thr Ile Gln Ala Val Leu Glu Asp Ala
35 40 45

```
Gln Glu Lys Gln Leu Asn Asp Lys Pro Leu Glu Asn Trp Leu Gln Lys
 50                  55                  60

Leu Asn Ala Ala Thr Tyr Glu Val Asp Ile Leu Asp Glu Tyr Lys
 65                  70                  75                  80

Thr Glu Ala Thr Arg Phe Leu Gln Ser Glu Tyr Gly Arg Tyr His Pro
                 85                  90                  95

Lys Ala Ile Pro Phe Arg His Lys Val Gly Lys Arg Met Asp Gln Val
                100                 105                 110

Met Lys Lys Leu Asn Ala Ile Ala Glu Glu Arg Lys Asn Phe His Leu
            115                 120                 125

Gln Glu Lys Ile Ile Glu Arg Gln Ala Ala Thr Arg Glu Thr Gly Ser
            130                 135                 140

Val Leu Thr Glu Pro Gln Val Tyr Gly Arg Asp Lys Glu Asn Asp Glu
145                 150                 155                 160

Ile Val Lys Ile Leu Ile Asn Asn Ala Ser Asp Ala Gln Lys Leu Arg
                165                 170                 175

Val Leu Pro Ile Leu Gly Met Gly Gly Leu Gly Lys Thr Thr Leu Ser
                180                 185                 190

Gln Met Val Phe Asn Asp Gln Arg Val Thr Glu His Phe Tyr Pro Lys
            195                 200                 205

Leu Trp Ile Cys Val Ser Asn Asp Phe Asp Glu Lys Arg Leu Ile Lys
            210                 215                 220

Ala Ile Val Glu Ser Ile Glu Gly Lys Ser Leu Ser Asp Met Asp Leu
225                 230                 235                 240

Ala Pro Leu Gln Lys Lys Leu Gln Glu Leu Gln Asn Gly Lys Arg Tyr
                245                 250                 255

Leu Leu Val Leu Asp Asp Val Trp Asn Glu Asp Gln Gln Lys Trp Ala
                260                 265                 270

Asn Leu Arg Ala Val Leu Lys Val Gly Ala Ser Gly Ser Phe Val Leu
            275                 280                 285

Thr Thr Thr Arg Leu Glu Lys Val Gly Ser Ile Met Gly Thr Leu Gln
            290                 295                 300

Pro Tyr Glu Leu Ser Asn Leu Ser Pro Glu Asp Cys Trp Phe Leu Phe
305                 310                 315                 320

Ile Gln Arg Ala Phe Gly His Gln Glu Ile Asn Pro Asn Leu Val
                325                 330                 335

Asp Ile Gly Lys Glu Ile Met Lys Lys Ser Gly Gly Val Pro Leu Ala
                340                 345                 350

Ala Lys Thr Leu Gly Gly Ile Leu Arg Phe Lys Arg Glu Glu Arg Glu
            355                 360                 365

Trp Glu His Val Arg Asp Ser Pro Ile Trp Asn Leu Pro Gln Asp Glu
            370                 375                 380

Ser Ser Ile Leu Pro Ala Leu Arg Leu Ser Tyr His His Leu Pro Leu
385                 390                 395                 400

Asp Leu Arg Gln Cys Phe Val Tyr Cys Ala Val Phe Pro Lys Asp Thr
                405                 410                 415

Lys Met Ala Lys Glu Asn Leu Ile Ala Phe Trp Met Ala His Gly Phe
            420                 425                 430

Leu Leu Ser Lys Gly Asn Leu Glu Leu Glu Asp Val Gly Asn Glu Val
            435                 440                 445

Trp Asn Glu Leu Tyr Leu Arg Ser Phe Phe Gln Glu Ile Glu Val Lys
            450                 455                 460

Asp Gly Lys Thr Tyr Phe Lys Met His Asp Leu Ile His Asp Leu Ala
465                 470                 475                 480
```

```
Thr Ser Leu Phe Ser Ala Asn Thr Ser Ser Ser Asn Ile Arg Glu Ile
                485                 490                 495

Tyr Val Asn Tyr Asp Gly Tyr Met Met Ser Ile Gly Phe Ala Glu Val
            500                 505                 510
Val Ser Ser Tyr Ser Pro Ser Leu
        515                 520

<210> SEQ ID NO 16
<211> LENGTH: 23
<212> TYPE: PRT
<213> ORGANISM: Solanum verrucosum

<400> SEQUENCE: 16

Leu Gln Lys Phe Val Ser Leu Arg Val Leu Asn Leu Arg Asn Ser Asp
1               5                   10                  15
Leu Asn Gln Leu Pro Ser Ser
            20

<210> SEQ ID NO 17
<211> LENGTH: 24
<212> TYPE: PRT
<213> ORGANISM: Solanum verrucosum

<400> SEQUENCE: 17

Ile Gly Asp Leu Val His Leu Arg Tyr Leu Asp Leu Ser Asp Asn Ile
1               5                   10                  15

Arg Ile Arg Ser Leu Pro Lys Arg
            20

<210> SEQ ID NO 18
<211> LENGTH: 24
<212> TYPE: PRT
<213> ORGANISM: Solanum verrucosum

<400> SEQUENCE: 18

Leu Cys Lys Leu Gln Asn Leu Gln Thr Leu Asp Leu His Asn Cys Tyr
1               5                   10                  15

Ser Leu Ser Cys Leu Pro Lys Gln
            20

<210> SEQ ID NO 19
<211> LENGTH: 26
<212> TYPE: PRT
<213> ORGANISM: Solanum verrucosum

<400> SEQUENCE: 19

Thr Ser Lys Leu Gly Ser Leu Arg Asn Leu Leu Leu Asp Gly Cys Ser
1               5                   10                  15

Leu Thr Ser Thr Pro Pro Arg Ile Gly Leu
            20                  25

<210> SEQ ID NO 20
<211> LENGTH: 16
<212> TYPE: PRT
<213> ORGANISM: Solanum verrucosum

<400> SEQUENCE: 20

Leu Thr Cys Leu Lys Ser Leu Ser Cys Phe Val Ile Gly Lys Arg Lys
1               5                   10                  15

<210> SEQ ID NO 21
<211> LENGTH: 14
```

```
<212> TYPE: PRT
<213> ORGANISM: Solanum verrucosum

<400> SEQUENCE: 21

Gly Tyr Gln Leu Gly Glu Leu Lys Asn Leu Asn Leu Tyr Gly
1               5                   10

<210> SEQ ID NO 22
<211> LENGTH: 20
<212> TYPE: PRT
<213> ORGANISM: Solanum verrucosum

<400> SEQUENCE: 22

Ser Ile Ser Ile Thr Lys Leu Glu Arg Val Lys Gly Arg Asp Ala
1               5                   10                  15

Lys Glu Ala Asn
            20

<210> SEQ ID NO 23
<211> LENGTH: 23
<212> TYPE: PRT
<213> ORGANISM: Solanum verrucosum

<400> SEQUENCE: 23

Ile Ser Val Lys Ala Asn Leu His Ser Leu Ser Leu Ser Trp Asp Phe
1               5                   10                  15

Asp Gly Thr His Arg Tyr Glu
            20

<210> SEQ ID NO 24
<211> LENGTH: 14
<212> TYPE: PRT
<213> ORGANISM: Solanum verrucosum

<400> SEQUENCE: 24

Ser Glu Val Leu Glu Ala Leu Lys Pro His Ser Asn Leu Lys
1               5                   10

<210> SEQ ID NO 25
<211> LENGTH: 17
<212> TYPE: PRT
<213> ORGANISM: Solanum verrucosum

<400> SEQUENCE: 25

Tyr Leu Glu Ile Ile Gly Phe Arg Gly Ile Arg Leu Pro Asp Trp Met
1               5                   10                  15

Asn

<210> SEQ ID NO 26
<211> LENGTH: 23
<212> TYPE: PRT
<213> ORGANISM: Solanum verrucosum

<400> SEQUENCE: 26

Gln Ser Val Leu Lys Asn Val Val Ser Ile Thr Ile Arg Gly Cys Glu
1               5                   10                  15

Asn Cys Ser Cys Leu Pro Pro
            20

<210> SEQ ID NO 27
<211> LENGTH: 15
<212> TYPE: PRT
<213> ORGANISM: Solanum verrucosum
```

-continued

```
<400> SEQUENCE: 27

Phe Gly Glu Leu Pro Ser Leu Glu Ser Leu Glu Leu His Thr Gly
1               5                   10                  15

<210> SEQ ID NO 28
<211> LENGTH: 12
<212> TYPE: PRT
<213> ORGANISM: Solanum verrucosum

<400> SEQUENCE: 28

Ser Ala Glu Val Glu Tyr Val Glu Glu Asn Ala His
1               5                   10

<210> SEQ ID NO 29
<211> LENGTH: 26
<212> TYPE: PRT
<213> ORGANISM: Solanum verrucosum

<400> SEQUENCE: 29

Pro Gly Arg Phe Pro Ser Leu Arg Lys Leu Val Ile Cys Asp Phe Gly
1               5                   10                  15

Asn Leu Lys Gly Leu Leu Lys Lys Glu Gly
            20                  25

<210> SEQ ID NO 30
<211> LENGTH: 19
<212> TYPE: PRT
<213> ORGANISM: Solanum verrucosum

<400> SEQUENCE: 30

Glu Glu Gln Phe Pro Val Leu Glu Glu Met Thr Ile His Gly Cys Pro
1               5                   10                  15

Met Phe Val

<210> SEQ ID NO 31
<211> LENGTH: 22
<212> TYPE: PRT
<213> ORGANISM: Solanum verrucosum

<400> SEQUENCE: 31

Ile Pro Thr Leu Ser Ser Val Lys Thr Leu Lys Val Asp Val Thr Asp
1               5                   10                  15

Ala Thr Val Leu Arg Ser
            20

<210> SEQ ID NO 32
<211> LENGTH: 25
<212> TYPE: PRT
<213> ORGANISM: Solanum verrucosum

<400> SEQUENCE: 32

Ile Ser Asn Leu Arg Ala Leu Thr Ser Leu Asp Ile Ser Ser Asn Tyr
1               5                   10                  15

Glu Ala Thr Ser Leu Pro Glu Glu Met
            20                  25

<210> SEQ ID NO 33
<211> LENGTH: 24
<212> TYPE: PRT
<213> ORGANISM: Solanum verrucosum

<400> SEQUENCE: 33

Phe Lys Asn Leu Ala Asp Leu Lys Asp Leu Thr Ile Ser Asp Phe Lys
```

```
                1               5                  10                 15
Asn Leu Lys Glu Leu Pro Thr Cys
                20

<210> SEQ ID NO 34
<211> LENGTH: 25
<212> TYPE: PRT
<213> ORGANISM: Solanum verrucosum

<400> SEQUENCE: 34

Leu Ala Ser Leu Asn Ala Leu Asn Ser Leu Gln Ile Glu Tyr Cys Asp
1               5                  10                 15

Ala Leu Glu Ser Leu Pro Glu Glu Gly
                20                 25

<210> SEQ ID NO 35
<211> LENGTH: 24
<212> TYPE: PRT
<213> ORGANISM: Solanum verrucosum

<400> SEQUENCE: 35

Val Lys Ser Leu Thr Ser Leu Thr Glu Leu Ser Val Ser Asn Cys Met
1               5                  10                 15

Thr Leu Lys Cys Leu

```
            130                 135                 140
Glu Ala Asn Leu Ser Ala Lys Gly Asn Leu His Ser Leu Ser Met Ser
145                 150                 155                 160

Trp Asn Asn Phe Gly Pro His Ile Tyr Glu Ser Glu Val Lys Val
                165                 170                 175

Leu Glu Ala Leu Lys Pro His Ser Asn Leu Thr Ser Leu Lys Ile Tyr
                180                 185                 190

Gly Phe Arg Gly Ile His Leu Pro Glu Trp Met Asn His Ser Val Leu
                195                 200                 205

Lys Asn Ile Val Ser Ile Leu Ile Ser Asn Phe Arg Asn Cys Ser Cys
210                 215                 220

Leu Pro Pro Phe Gly Asp Leu Pro Cys Leu Glu Ser Leu Glu Leu His
225                 230                 235                 240

Trp Gly Ser Ala Asp Val Glu Tyr Val Glu Val Asp Ile Asp Val
                245                 250                 255

His Ser Gly Phe Pro Thr Arg Ile Arg Phe Pro Ser Leu Arg Lys Leu
                260                 265                 270

Asp Ile Trp Asp Phe Gly Ser Leu Lys Gly Leu Leu Lys Lys Glu Gly
                275                 280                 285

Glu Glu Gln Phe Pro Val Leu Glu Glu Met Ile Ile His Glu Cys Pro
290                 295                 300

Phe Leu Thr Leu Ser Ser Asn Leu Arg Ala Leu Thr Ser Leu Arg Ile
305                 310                 315                 320

Cys Tyr Asn Lys Val Ala Thr Ser Phe Pro Glu Glu Met Phe Lys Asn
                325                 330                 335

Leu Ala Asn Leu Lys Tyr Leu Thr Ile Ser Arg Cys Asn Asn Leu Lys
                340                 345                 350

Glu Leu Pro Thr Ser Leu Ala Ser Leu Asn Ala Leu Lys Ser Leu Lys
                355                 360                 365

Ile Gln Leu Cys Cys Ala Leu Glu Ser Leu Pro Glu Glu Gly Leu Glu
                370                 375                 380

Gly Leu Ser Ser Leu Thr Glu Leu Phe Val Glu His Cys Asn Met Leu
385                 390                 395                 400

Lys Cys Leu Pro Glu Gly Leu Gln His Leu Thr Thr Leu Thr Ser Leu
                405                 410                 415

Lys Ile Arg Gly Cys Pro Gln Leu Ile Lys Arg Cys Lys Gly Ile
                420                 425                 430

Gly Glu Asp Trp His Lys Ile Ser His Ile Pro Asn Val Asn Ile Tyr
                435                 440                 445

Ile

<210> SEQ ID NO 38
<211> LENGTH: 441
<212> TYPE: PRT
<213> ORGANISM: Solanum verrucosum

<400> SEQUENCE: 38

Leu Gln Lys Phe Val Ser Leu Arg Val Leu Asn Leu Arg Asn Ser Asp
1               5                   10                  15

Leu Asn Gln Leu Pro Ser Ser Ile Gly Asp Leu Val His Leu Arg Tyr
                20                  25                  30

Leu Asp Leu Ser Asp Asn Ile Arg Ile Arg Ser Leu Pro Lys Arg Leu
        35                  40                  45

Cys Lys Leu Gln Asn Leu Gln Thr Leu Asp Leu His Asn Cys Tyr Ser
50                  55                  60
```

Leu Ser Cys Leu Pro Lys Gln Thr Ser Lys Leu Gly Ser Leu Arg Asn
65                  70                  75                  80

Leu Leu Leu Asp Gly Cys Ser Leu Thr Ser Thr Pro Pro Arg Ile Gly
            85                  90                  95

Leu Leu Thr Cys Leu Lys Ser Leu Ser Cys Phe Val Ile Gly Lys Arg
        100                 105                 110

Lys Gly Tyr Gln Leu Gly Glu Leu Lys Asn Leu Asn Leu Tyr Gly Ser
    115                 120                 125

Ile Ser Ile Thr Lys Leu Glu Arg Val Lys Gly Arg Asp Ala Lys
130                 135                 140

Glu Ala Asn Ile Phe Val Lys Ala Asn Leu His Ser Leu Ser Leu Ser
145                 150                 155                 160

Trp Asp Phe Asp Gly Thr His Arg Tyr Glu Ser Glu Val Leu Glu Ala
                165                 170                 175

Leu Lys Pro His Ser Asn Leu Lys Tyr Leu Glu Ile Ile Gly Phe Arg
            180                 185                 190

Gly Ile Arg Leu Pro Asp Trp Met Asn Gln Ser Val Leu Lys Asn Val
        195                 200                 205

Val Ser Ile Thr Ile Arg Gly Cys Glu Asn Cys Ser Cys Leu Pro Pro
210                 215                 220

Phe Gly Glu Leu Pro Ser Leu Glu Ser Leu His Thr Gly Ser
225                 230                 235                 240

Ala Glu Val Glu Tyr Val Glu Glu Asn Ala His Pro Gly Arg Phe Pro
                245                 250                 255

Ser Leu Arg Lys Leu Val Ile Cys Asp Phe Gly Asn Leu Lys Gly Leu
            260                 265                 270

Leu Lys Lys Glu Gly Glu Gln Val Pro Val Leu Glu Glu Met Thr
        275                 280                 285

Ile His Gly Cys Pro Met Phe Val Ile Pro Thr Leu Ser Ser Val Lys
290                 295                 300

Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asn Leu Lys Asp
            340                 345                 350

Leu Thr Ile Ser Asp Phe Lys Asn Leu Lys Glu Leu Pro Thr Cys Leu
        355                 360                 365

Ala Ser Leu Asn Ala Leu Asn Ser Leu Gln Ile Glu Tyr Cys Asp Ala
370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Thr Leu Ile Ile Thr Gln Cys Pro
            420                 425                 430

Ile Val Ile Lys Arg Cys Glu Lys Glu
        435                 440

<210> SEQ ID NO 39
<211> LENGTH: 441
<212> TYPE: PRT
<213> ORGANISM: Solanum verrucosum

<400> SEQUENCE: 39

-continued

```
Leu Gln Lys Phe Val Ser Leu Arg Val Leu Asn Leu Arg Asn Ser Asp
1               5                   10                  15
Leu Asn Gln Leu Pro Ser Ser Ile Gly Asp Val Val His Leu Arg Tyr
            20                  25                  30
Leu Asp Leu Ser Asp Asn Ile Arg Ile Arg Ser Leu Pro Lys Arg Leu
        35                  40                  45
Cys Lys Leu Gln Asn Leu Gln Thr Leu Asp Leu Arg Asn Cys Tyr Ser
50                  55                  60
Leu Ser Cys Leu Pro Lys Gln Thr Ser Lys Leu Gly Ser Leu Arg Asn
65                  70                  75                  80
Leu Leu Leu Asp Gly Cys Ser Leu Thr Ser Thr Pro Arg Ile Gly
                85                  90                  95
Leu Leu Thr Cys Leu Lys Ser Leu Ser Cys Phe Val Ile Gly Lys Arg
            100                 105                 110
Lys Gly Tyr Leu Leu Gly Glu Leu Arg Asn Leu Asn Leu Tyr Gly Ser
            115                 120                 125
Ile Ser Ile Thr Lys Leu Glu Arg Val Lys Lys Gly Arg Asp Ala Lys
130                 135                 140
Glu Ala Asn Ile Ser Val Lys Ala Asn Leu His Ser Leu Ser Leu Ser
145                 150                 155                 160
Trp Asp Phe Asp Gly Thr His Arg Tyr Glu Ser Glu Val Leu Glu Ala
                165                 170                 175
Leu Lys Pro His Ser Asn Leu Lys Tyr Leu Glu Ile Ile Gly Phe Arg
            180                 185                 190
Gly Ile His Leu Pro Asp Trp Met Asn Gln Ser Val Leu Lys Asn Val
            195                 200                 205
Val Ser Ile Thr Ile Arg Gly Cys Glu Asn Cys Ser Cys Leu Pro Pro
210                 215                 220
Phe Gly Glu Leu Pro Ser Leu Glu Ser Leu Glu Leu His Thr Gly Ser
225                 230                 235                 240
Ala Glu Val Glu Tyr Val Glu Glu Asn Ala His Pro Gly Arg Phe Pro
                245                 250                 255
Ser Leu Arg Lys Leu Val Ile Cys Asp Phe Gly Asn Leu Lys Gly Leu
            260                 265                 270
Leu Lys Lys Glu Gly Glu Gln Phe Pro Val Leu Glu Glu Met Thr
            275                 280                 285
Ile His Gly Cys Pro Met Phe Val Ile Pro Thr Leu Ser Ser Val Lys
290                 295                 300
Thr Leu Lys Val Asp Ala Thr Asp Ala Thr Val Leu Arg Ser Ile Ser
305                 310                 315                 320
Asn Leu Arg Ala Leu Thr Ser Leu Asp Ile Ser Ser Asn Tyr Glu Ala
                325                 330                 335
Thr Ser Leu Pro Glu Glu Met Phe Lys Asn Leu Ala Asn Leu Lys Asp
            340                 345                 350
Leu Thr Ile Ser Asp Phe Lys Asn Leu Lys Glu Leu Pro Thr Cys Leu
            355                 360                 365
Ala Ser Leu Asn Ala Leu Asn Ser Leu Gln Ile Glu Tyr Cys Asp Ala
370                 375                 380
Leu Glu Ser Leu Pro Glu Glu Gly Val Lys Ser Leu Thr Ser Leu Thr
385                 390                 395                 400
Glu Leu Ser Val Ser Asn Cys Met Thr Leu Lys Cys Leu Pro Glu Gly
                405                 410                 415
Leu Gln His Leu Thr Ala Leu Thr Thr Leu Ile Ile Thr Gln Cys Pro
```

```
                        420             425             430
Ile Val Ile Lys Arg Cys Glu Lys Glu
            435             440

<210> SEQ ID NO 40
<211> LENGTH: 441
<212> TYPE: PRT
<213> ORGANISM: Solanum verrucosum

<400> SEQUENCE: 40

Leu Gln Lys Phe Val Ser Leu Arg Val Leu Asn Leu Arg Asn Ser Asp
1               5                   10                  15

Leu Asn Gln Leu Pro Ser Ser Ile Gly Asp Leu Val His Leu Arg Tyr
            20                  25                  30

Leu Asp Leu Ser Asp Asn Ile Arg Ile Arg Ser Leu Pro Lys Arg Leu
        35                  40                  45

Cys Glu Leu Gln Asn Leu Gln Thr Leu Asp Leu His Asn Cys Tyr Ser
    50                  55                  60

Leu Ser Cys Leu Pro Lys Gln Thr Ser Lys Leu Gly Ser Leu Arg Asn
65                  70                  75                  80

Leu Leu Leu Asp Gly Cys Ser Leu Thr Ser Thr Pro Pro Arg Ile Gly
                85                  90                  95

Leu Leu Thr Cys Leu Lys Ser Leu Ser Cys Phe Val Ile Gly Lys Arg
            100                 105                 110

Lys Gly Tyr Gln Leu Gly Glu Leu Lys Asn Leu Asn Leu Tyr Gly Ser
        115                 120                 125

Ile Ser Ile Thr Lys Leu Glu Arg Val Lys Gly Arg Asp Ala Lys
    130                 135                 140

Glu Ala Asn Ile Ser Val Lys Ala Asn Leu His Ser Leu Ser Leu Ser
145                 150                 155                 160

Trp Asp Phe Asp Gly Thr His Arg Tyr Glu Ser Glu Val Leu Glu Ala
                165                 170                 175

Leu Lys Pro His Ser Asn Leu Lys Tyr Leu Glu Ile Ile Gly Phe Arg
            180                 185                 190

Gly Ile Arg Leu Pro Asp Trp Met Asn Gln Ser Val Leu Lys Asn Val
        195                 200                 205

Val Ser Ile Thr Ile Arg Gly Cys Glu Asn Cys Ser Cys Leu Pro Pro
    210                 215                 220

Phe Gly Glu Leu Pro Ser Leu Glu Ser Leu Glu Leu His Thr Gly Ser
225                 230                 235                 240

Ala Glu Val Glu Tyr Val Glu Asn Ala His Pro Gly Arg Phe Pro
                245                 250                 255

Ser Leu Arg Lys Leu Val Ile Cys Asp Phe Gly Asn Leu Lys Gly Leu
            260                 265                 270

Leu Lys Lys Glu Gly Glu Gln Phe Pro Val Leu Glu Glu Met Thr
        275                 280                 285

Ile His Gly Cys Pro Met Phe Val Ile Pro Thr Leu Ser Ser Val Lys
    290                 295                 300

Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asn Leu Lys Asp
            340                 345                 350

Leu Thr Ile Ser Asp Phe Lys Asn Leu Lys Glu Leu Pro Thr Cys Leu
```

```
                355                 360                 365
Ala Ser Leu Asn Ala Leu Asn Ser Leu Gln Ile Glu Tyr Cys Asp Ala
    370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Leu Ile Ile Thr Gln Cys Pro
                420                 425                 430

Ile Val Ile Lys Arg Cys Glu Lys Glu
                435                 440

<210> SEQ ID NO 41
<211> LENGTH: 441
<212> TYPE: PRT
<213> ORGANISM: Solanum verrucosum

<400> SEQUENCE: 41

Leu Gln Lys Phe Val Ser Leu Arg Val Leu Asn Leu Arg Asn Ser Asp
1               5                   10                  15

Leu Asn Gln Leu Pro Ser Ser Ile Gly Asp Val Val His Leu Arg Tyr
                20                  25                  30

Leu Asp Leu Ser Asp Asn Ile Arg Ile Arg Ser Leu Pro Lys Arg Leu
            35                  40                  45

Cys Lys Leu Gln Asn Leu Gln Thr Leu Asp Leu Arg Asn Cys Tyr Ser
        50                  55                  60

Leu Ser Cys Leu Pro Lys Gln Thr Ser Lys Leu Gly Ser Leu Arg Asn
65                  70                  75                  80

Leu Leu Leu Gly Gly Cys Ser Leu Ala Ser Thr Pro Pro Arg Ile Gly
                85                  90                  95

Leu Leu Thr Cys Leu Lys Ser Leu Ser Cys Phe Val Ile Gly Lys Arg
                100                 105                 110

Lys Gly Tyr Leu Leu Gly Glu Leu Arg Asn Leu Asn Leu Tyr Gly Ser
            115                 120                 125

Ile Ser Ile Thr Lys Leu Glu Arg Val Lys Lys Gly Arg Asp Ala Lys
        130                 135                 140

Glu Ala Asn Ile Ser Val Lys Ala Asn Leu His Ser Leu Ser Leu Ser
145                 150                 155                 160

Trp Asp Phe Asp Gly Thr His Arg Tyr Glu Ser Glu Val Leu Glu Ala
                165                 170                 175

Leu Lys Pro His Ser Asn Leu Lys Tyr Leu Glu Ile Ile Gly Phe Arg
                180                 185                 190

Gly Ile His Leu Pro Asp Trp Met Asn Gln Ser Val Leu Lys Asn Val
            195                 200                 205

Val Ser Ile Thr Ile Arg Gly Cys Glu Asn Cys Ser Cys Leu Pro Pro
        210                 215                 220

Phe Gly Glu Leu Pro Ser Leu Glu Ser Leu Glu Leu His Thr Gly Ser
225                 230                 235                 240

Ala Glu Val Glu Tyr Val Glu Glu Asn Ala His Pro Gly Arg Phe Pro
                245                 250                 255

Ser Leu Arg Lys Leu Val Ile Cys Asp Phe Gly Asn Leu Lys Gly Leu
                260                 265                 270

Leu Lys Lys Glu Gly Glu Glu Gln Phe Pro Val Leu Glu Glu Met Thr
            275                 280                 285

Ile His Gly Cys Pro Met Phe Val Ile Pro Thr Leu Ser Ser Val Lys
```

```
                    290                 295                 300
Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asn Leu Lys Asp
            340                 345                 350

Leu Thr Ile Ser Asp Phe Lys Asn Leu Lys Glu Leu Pro Thr Cys Leu
            355                 360                 365

Ala Ser Leu Asn Ala Leu Asn Ser Leu Gln Ile Glu Tyr Cys Asp Ala
            370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Thr Leu Ile Ile Ile Gln Cys Pro
            420                 425                 430

Ile Val Ile Lys Arg Cys Glu Lys Glu
            435                 440

<210> SEQ ID NO 42
<211> LENGTH: 441
<212> TYPE: PRT
<213> ORGANISM: Solanum verrucosum

<400> SEQUENCE: 42

Leu Gln Lys Phe Val Ser Leu Arg Val Leu Asn Leu Arg Asn Ser Asp
1               5                   10                  15

Leu Asn Gln Leu Pro Ser Ser Ile Gly Asp Leu Val His Leu Arg Tyr
            20                  25                  30

Leu Asp Leu Ser Asp Asn Ile Arg Ile Arg Ser Leu Pro Lys Arg Leu
        35                  40                  45

Cys Lys Leu Gln Asn Leu Gln Thr Leu Asp Leu His Asn Cys Tyr Ser
    50                  55                  60

Leu Ser Cys Leu Pro Lys Gln Thr Ser Lys Leu Gly Ser Leu Arg Asn
65                  70                  75                  80

Leu Leu Leu Asp Gly Cys Ser Leu Thr Ser Thr Pro Pro Arg Ile Gly
                85                  90                  95

Leu Leu Thr Cys Leu Lys Ser Leu Ser Cys Phe Val Ile Gly Lys Arg
            100                 105                 110

Lys Gly Tyr Gln Leu Gly Glu Leu Lys Asn Leu Asn Leu Tyr Gly Ser
        115                 120                 125

Ile Ser Ile Thr Lys Leu Glu Arg Val Lys Lys Gly Arg Asp Ala Lys
    130                 135                 140

Glu Ala Asn Ile Ser Val Lys Ala Asn Leu His Ser Leu Ser Leu Ser
145                 150                 155                 160

Trp Asp Phe Asp Gly Thr His Arg Tyr Glu Ser Glu Val Leu Glu Ala
                165                 170                 175

Leu Lys Pro His Ser Asn Leu Lys Tyr Leu Glu Ile Ile Gly Phe Arg
            180                 185                 190

Gly Ile Arg Leu Pro Asp Trp Met Asn Gln Ser Val Leu Lys Asn Val
        195                 200                 205

Val Ser Ile Thr Ile Arg Gly Cys Glu Asn Cys Ser Cys Leu Pro Pro
    210                 215                 220

Phe Gly Glu Leu Pro Ser Leu Glu Ser Leu Glu Leu His Thr Gly Ser
```

```
                225                 230                 235                 240
Ala Glu Val Glu Tyr Val Glu Asn Ala His Pro Gly Arg Phe Pro
                    245                 250                 255

Ser Leu Arg Lys Leu Val Ile Cys Asp Phe Gly Asn Leu Lys Gly Leu
                260                 265                 270

Leu Lys Lys Glu Gly Glu Gln Phe Pro Val Leu Glu Glu Met Thr
            275                 280                 285

Ile His Gly Cys Pro Met Phe Val Ile Pro Thr Leu Ser Ser Val Lys
        290                 295                 300

Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asp Leu Lys Asp
            340                 345                 350

Leu Thr Ile Ser Asp Phe Lys Asn Leu Lys Glu Leu Pro Thr Cys Leu
        355                 360                 365

Ala Ser Leu Asn Ala Leu Asn Ser Leu Gln Ile Glu Tyr Cys Asp Ala
    370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Thr Leu Ile Ile Thr Gln Cys Pro
            420                 425                 430

Ile Val Ile Lys Arg Cys Glu Lys Glu
        435                 440

<210> SEQ ID NO 43
<211> LENGTH: 441
<212> TYPE: PRT
<213> ORGANISM: Solanum verrucosum

<400> SEQUENCE: 43

Leu Gln Lys Phe Val Ser Leu Arg Val Leu Asn Leu Arg Asn Ser Asp
1               5                   10                  15

Leu Asn Gln Leu Pro Ser Ser Ile Gly Asp Val Val His Leu Arg Tyr
            20                  25                  30

Leu Asp Leu Ser Asp Asn Ile Arg Ile Arg Ser Leu Pro Lys Arg Leu
        35                  40                  45

Cys Lys Leu Gln Asn Leu Gln Thr Leu Asp Leu Arg Asn Cys Tyr Ser
    50                  55                  60

Leu Ser Cys Leu Pro Lys Gln Thr Ser Lys Leu Gly Ser Leu Arg Asn
65                  70                  75                  80

Leu Leu Leu Gly Gly Cys Ser Leu Thr Ser Thr Pro Pro Arg Ile Gly
                85                  90                  95

Leu Leu Thr Cys Leu Lys Ser Leu Ser Arg Phe Val Ile Gly Lys Arg
            100                 105                 110

Lys Gly Tyr Leu Leu Gly Glu Leu Arg Asn Leu Asn Leu Tyr Gly Ser
        115                 120                 125

Ile Ser Ile Thr Lys Leu Glu Arg Val Lys Lys Gly Arg Asp Ala Lys
    130                 135                 140

Glu Ala Asn Ile Ser Val Lys Ala Asn Leu His Ser Leu Ser Leu Ser
145                 150                 155                 160

Trp Asp Phe Asp Gly Thr His Arg Tyr Glu Ser Glu Val Leu Glu Ala
```

```
                      165                 170                 175
Leu Lys Pro His Ser Asn Leu Lys Tyr Leu Glu Ile Ile Gly Phe Arg
            180                 185                 190

Gly Ile His Leu Pro Asp Trp Met Asn Gln Ser Val Leu Lys Asn Val
        195                 200                 205

Val Ser Ile Thr Ile Arg Gly Cys Glu Asn Cys Ser Cys Leu Pro Pro
    210                 215                 220

Phe Gly Glu Leu Pro Ser Leu Glu Ser Leu Glu Leu His Thr Gly Ser
225                 230                 235                 240

Ala Glu Val Glu Tyr Val Glu Glu Asn Ala His Pro Gly Arg Phe Pro
                245                 250                 255

Ser Leu Arg Lys Leu Val Ile Cys Asp Phe Gly Asn Leu Lys Gly Leu
            260                 265                 270

Leu Lys Lys Glu Gly Glu Gln Phe Pro Val Leu Glu Glu Met Thr
        275                 280                 285

Ile His Gly Cys Pro Met Phe Val Ile Pro Thr Leu Ser Ser Val Lys
    290                 295                 300

Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asn Leu Lys Asp
            340                 345                 350

Leu Thr Ile Ser Asp Phe Lys Asn Leu Lys Glu Leu Pro Thr Cys Leu
        355                 360                 365

Ala Ser Leu Asn Ala Leu Asn Ser Leu Gln Ile Glu Tyr Cys Asp Ala
    370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Thr Leu Ile Ile Ile Gln Cys Pro
            420                 425                 430

Ile Val Ile Lys Arg Cys Glu Lys Glu
        435                 440

<210> SEQ ID NO 44
<211> LENGTH: 441
<212> TYPE: PRT
<213> ORGANISM: Solanum verrucosum

<400> SEQUENCE: 44

Leu Gln Lys Phe Val Ser Leu Arg Val Leu Asn Leu Arg Asn Ser Asp
1               5                  10                  15

Leu Asn Gln Leu Pro Ser Ser Ile Gly Asp Val Val His Leu Arg Tyr
            20                  25                  30

Leu Asp Leu Ser Asp Asn Ile Arg Ile Arg Ser Leu Pro Lys Arg Leu
        35                  40                  45

Cys Lys Le

```
                      100                 105                 110
Lys Gly Tyr Leu Leu Gly Glu Leu Arg Asn Leu Asn Leu Tyr Gly Ser
            115                 120                 125

Ile Ser Ile Thr Lys Leu Glu Arg Val Lys Gly Arg Asp Ala Lys
        130                 135                 140

Glu Ala Asn Ile Ser Val Lys Ala Asn Leu His Ser Leu Ser Leu Ser
145                 150                 155                 160

Trp Asp Phe Asp Gly Thr His Arg Tyr Glu Ser Glu Val Leu Glu Ala
                165                 170                 175

Leu Lys Pro His Ser Asn Leu Lys Tyr Leu Glu Ile Ile Gly Phe Arg
            180                 185                 190

Gly Ile His Leu Pro Asp Trp Met Asn Gln Ser Val Leu Lys Asn Val
        195                 200                 205

Val Ser Ile Thr Ile Arg Gly Cys Glu Asn Cys Ser Cys Leu Pro Pro
210                 215                 220

Phe Gly Glu Leu Pro Ser Leu Glu Ser Leu Glu Leu His Thr Gly Ser
225                 230                 235                 240

Ala Glu Val Glu Tyr Val Glu Glu Asn Ala His Pro Gly Arg Phe Pro
                245                 250                 255

Ser Leu Arg Lys Leu Val Ile Cys Asp Phe Gly Asn Leu Lys Gly Leu
            260                 265                 270

Leu Lys Lys Glu Gly Glu Gln Phe Pro Val Leu Glu Met Thr
        275                 280                 285

Ile His Gly Cys Pro Met Phe Val Ile Pro Thr Leu Ser Ser Val Lys
        290                 295                 300

Thr Leu Lys Val Asp Val Thr Asp Ala Thr Val Leu Arg Ser Ile Ser
305                 310                 315                 320

Asn Leu Arg Ala Leu Thr Ser Leu Asp Ile Ser Ser Asn Tyr Glu Ala
                325                 330                 335

Thr Ser Leu Pro Glu Glu Met Phe Lys Asn Leu Ala Asn Leu Lys Asp
            340                 345                 350

Leu Thr Ile Ser Asp Phe Lys Asn Leu Lys Glu Leu Pro Thr Cys Leu
        355                 360                 365

Ala Ser Leu Asn Ala Leu Asn Ser Leu Gln Ile Glu Tyr Cys Asp Ala
        370                 375                 380

Leu Glu Ser Leu Pro Glu Glu Gly Val Lys Ser Leu Thr Ser Leu Thr
385                 390                 395                 400

Glu Leu Ser Val Ser Asn Cys Met Thr Leu Lys Cys Leu Pro Glu Gly
                405                 410                 415

Leu Gln His Leu Thr Ala Leu Thr Thr Leu Ile Ile Ile Gln Cys Pro
            420                 425                 430

Ile Val Ile Lys Arg Cys Glu Lys Glu
        435                 440

<210> SEQ ID NO 45
<211> LENGTH: 441
<212> TYPE: PRT
<213> ORGANISM: Solanum verrucosum

<400> SEQUENCE: 45

Leu Gln Lys Phe Val Ser Leu Arg Val Leu Asn Leu Arg Asn Ser Asp
1               5                   10                  15

Leu Asn Gln Leu Pro Ser Ser Ile Gly Asp Val Val His Leu Arg Tyr
            20                  25                  30

Leu Asp Leu Ser Asp Asn Ile Arg Ile Arg Ser Leu Pro Lys Arg Leu
```

```
                35                  40                  45
Cys Lys Leu Gln Asn Leu Gln Thr Leu Asp Leu Arg Asn Cys Tyr Ser
         50                  55                  60
Leu Ser Cys Leu Pro Lys Gln Thr Ser Lys Leu Gly Ser Leu Arg Asn
 65                  70                  75                  80
Leu Leu Leu Asp Gly Cys Ser Leu Thr Ser Thr Pro Pro Arg Ile Gly
                 85                  90                  95
Leu Leu Thr Cys Leu Lys Ser Leu Ser Cys Phe Val Ile Gly Lys Arg
                100                 105                 110
Lys Gly Tyr Leu Leu Gly Glu Leu Arg Asn Leu Asn Leu Tyr Gly Ser
            115                 120                 125
Ile Ser Ile Thr Lys Leu Glu Arg Val Lys Gly Arg Asp Ala Lys
        130                 135                 140
Glu Ala Asn Ile Ser Val Lys Ala Asn Leu His Ser Leu Ser Leu Ser
145                 150                 155                 160
Trp Asp Phe Asp Gly Thr His Arg Tyr Glu Ser Glu Val Leu Glu Ala
                165                 170                 175
Leu Lys Pro His Ser Asn Leu Lys Tyr Leu Glu Ile Ile Gly Phe Arg
            180                 185                 190
Gly Ile His Leu Pro Asp Trp Met Asn Gln Ser Val Leu Lys Asn Val
        195                 200                 205
Val Ser Ile Thr Ile Arg Gly Cys Glu Asn Tyr Ser Cys Leu Pro Pro
    210                 215                 220
Phe Gly Glu Leu Pro Ser Leu Glu Ser Leu Glu Leu His Thr Gly Ser
225                 230                 235                 240
Ala Glu Val Glu Tyr Val Glu Glu Asn Ala His Pro Gly Arg Phe Pro
                245                 250                 255
Ser Leu Arg Lys Leu Val Ile Cys Asp Phe Gly Asn Leu Lys Gly Leu
            260                 265                 270
Leu Lys Lys Glu Gly Glu Gln Phe Pro Val Leu Glu Glu Met Ser
        275                 280                 285
Ile His Gly Cys Pro Met Phe Val Ile Pro Thr Leu Ser Ser Val Lys
    290                 295                 300
Thr Leu Lys Val Asp Val Ala Asp Ala Thr Val Leu Arg Ser Ile Ser
305                 310                 315                 320
Asn Leu Arg Ala Leu Thr Ser Leu Asp Ile Ser Ser Asn Tyr Glu Ala
                325                 330                 335
Thr Ser Leu Pro Glu Glu Met Phe Lys Asn Leu Ala Asn Leu Lys Asp
            340                 345                 350
Leu Thr Ile Ser Asp Phe Lys Asn Leu Lys Glu Leu Pro Thr Cys Leu
        355                 360                 365
Ala Ser Leu Asn Ala Leu Asn Ser Leu Gln Ile Glu Tyr Cys Asp Ala
    370                 375                 380
Leu Glu Ser Leu Pro Glu Glu Gly Val Lys Ser Leu Thr Ser Leu Thr
385                 390                 395                 400
Glu Leu Ser Val Ser Asn Cys Met Thr Leu Lys Cys Leu Pro Glu Gly
                405                 410                 415
Leu Gln His Leu Thr Ala Leu Thr Thr Leu Ile Ile Gln Cys Pro
            420                 425                 430
Ile Val Ile Lys Arg Cys Glu Lys Glu
        435                 440
```